(12) United States Patent
Zhuo et al.

(10) Patent No.: US 9,072,729 B2
(45) Date of Patent: Jul. 7, 2015

(54) METHOD FOR TREATING FIBROSIS AND CANCER WITH IMIDAZOLIUM AND IMIDAZOLINIUM COMPOUNDS

(75) Inventors: Lang Zhuo, Singapore (SG); Chunyan Zhang, Singapore (SG); Yugen Zhang, Singapore (SG); Jackie Y. Ying, Singapore (SG); Began Gopalan, Singapore (SG); Zhiyuan Ke, Singapore (SG); Zhaobing Ding, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 342 days.

(21) Appl. No.: 12/865,668

(22) PCT Filed: Jan. 30, 2009

(86) PCT No.: PCT/SG2009/000037
§ 371 (c)(1),
(2), (4) Date: Feb. 28, 2011

(87) PCT Pub. No.: WO2009/096905
PCT Pub. Date: Aug. 6, 2009

(65) Prior Publication Data
US 2011/0178040 A1    Jul. 21, 2011

Related U.S. Application Data

(60) Provisional application No. 61/006,769, filed on Jan. 30, 2008.

(51) Int. Cl.
| | |
|---|---|
| *A61K 31/69* | (2006.01) |
| *A01N 55/08* | (2006.01) |
| *A61K 31/415* | (2006.01) |
| *A61K 31/4184* | (2006.01) |
| *A61K 31/4188* | (2006.01) |
| *A61K 31/439* | (2006.01) |
| *A61K 31/4439* | (2006.01) |
| *C07D 233/58* | (2006.01) |
| *C07D 233/60* | (2006.01) |
| *C07D 233/61* | (2006.01) |
| *C07D 235/06* | (2006.01) |
| *C07D 401/04* | (2006.01) |
| *C07D 401/14* | (2006.01) |
| *C07D 403/04* | (2006.01) |
| *C07D 471/04* | (2006.01) |
| *C07D 487/04* | (2006.01) |
| *C07D 487/22* | (2006.01) |

(52) U.S. Cl.
CPC ......... *A61K 31/4184* (2013.01); *A61K 31/4188* (2013.01); *A61K 31/439* (2013.01); *A61K 31/4439* (2013.01); *C07D 233/58* (2013.01); *C07D 233/60* (2013.01); *C07D 233/61* (2013.01); *C07D 235/06* (2013.01); *C07D 401/04* (2013.01); *C07D 401/14* (2013.01); *C07D 403/04* (2013.01); *C07D 471/04* (2013.01); *C07D 487/04* (2013.01); *C07D 487/22* (2013.01)

(58) Field of Classification Search
USPC ............... 514/64, 394, 397, 396; 435/375
See application file for complete search history.

(56) References Cited

U.S. PATENT DOCUMENTS

| | | | |
|---|---|---|---|
| 3,849,557 A | 11/1974 | Jack et al. | |
| 4,483,835 A * | 11/1984 | Zones | 423/706 |
| 6,194,447 B1 | 2/2001 | Jensen et al. | |
| 7,501,552 B2 | 3/2009 | Lonberg et al. | |
| 7,758,890 B2 | 7/2010 | Anderson et al. | |
| 2002/0052374 A1 | 5/2002 | Rabelink et al. | |
| 2002/0068729 A1 | 6/2002 | Egan et al. | |
| 2003/0027820 A1 | 2/2003 | Gall | |
| 2003/0176426 A1 * | 9/2003 | Wagle et al. | 514/227.8 |
| 2004/0116403 A1 | 6/2004 | Klimko et al. | |
| 2005/0058702 A1 | 3/2005 | Ben-Sasson et al. | |
| 2005/0272936 A1 | 12/2005 | Axten et al. | |
| 2005/0282803 A1 | 12/2005 | Haley et al. | |
| 2006/0149074 A1 | 7/2006 | Maase et al. | |
| 2007/0043016 A1 | 2/2007 | Wagle et al. | |

FOREIGN PATENT DOCUMENTS

| | | | |
|---|---|---|---|
| WO | 0025793 A1 | 5/2000 |
| WO | 0177486 A1 | 10/2001 |
| WO | 2004110364 A2 | 12/2004 |
| WO | 2005019183 A1 | 3/2005 |
| WO | 2006119589 A2 | 11/2006 |
| WO | 2009123569 A1 | 10/2009 |

OTHER PUBLICATIONS

Science Daily (2007).*
Ali, S. and Mann, D.A., "Signal transduction via the NF-kappaB pathway: A targeted treatment modality for infection, inflammation and repair", Cell Biochemistry and Function, Mar.-Apr. 2004, pp. 67-79, vol. 22, Issue 2.
Bachem, M.G. et al., "Activation of Rat Liver Perisinusoidal Lipocytes by Transforming Growth Factors Derived from Myofibroblastlike Cells. A Potential Mechanism of Self Perpetuation in Liver Fibrogenesis", The Journal of Clinical Investigation, Jan. 1, 1992, pp. 19-27, vol. 89, Issue 1.
Baker, M.V. et al., "Cationic, linear Au(I) N-heterocyclic carbene complexes: synthesis, structure and anti-mitochondrial activity", Dalton Transactions, 2006, pp. 3708-3715, Issue 30.

(Continued)

*Primary Examiner* — Shirley V Gembeh
(74) *Attorney, Agent, or Firm* — Klarquist Sparkman, LLP

(57) ABSTRACT

There is presently provided methods for delivering an anti-fibrotic or anti-cancer agent to a cell. The methods comprise contacting a cell with an effective amount of imidazolium and imidazolinium compounds as described herein, including imidazolium and imidazolinium salts.

10 Claims, 59 Drawing Sheets

(56) References Cited

OTHER PUBLICATIONS

Barnard, P.J. et al., "Mitochondrial permeability transition induced by dinuclear gold(I)-carbene complexes: Potential new antimitochondrial antitumour agents", Journal of Inorganic Biochemistry, Oct. 2004, pp. 1642-1647, vol. 98, Issue 10.
Baur, J.A. et al., "Resveratrol improves health and survival of mice on a high-calorie diet", Nature, Nov. 16, 2006, pp. 337-342, vol. 444, No. 7117.
Bourissou, D. et al., "Stable Carbenes", Chemical Reviews, Jan. 2000, pp. 39-91, vol. 100, Issue 1.
Britton, R.S. and Bacon, B.R., "Role of free radicals in liver diseases and hepatic fibrosis", Hepato-Gastroenterology, Aug. 1994, 343-348, vol. 41, Issue 4.
Cao, X.G. et al. "Responses of Human Lens Epithelial Cells to Quercetin and DMSO", Investigative Ophthalmology & Visual Science, Aug. 2007, pp. 3714-3718, vol. 48, Issue 8.
Casanovas, A. et al., "Induction of reactive astrocytosis and prevention of motoneuron cell death by the I2-imidazoline receptor ligand LSL 60101", British Journal of Pharmacology, Aug. 2000, pp. 1767-1776, vol. 130, Issue 8.
Casini, A. et al. "Neutrophil-Derived Superoxide Anion Induces Lip Peroxidation and Stimulates Collagen Synthesis in Human Hepatic Stellate Cells: Role of Nitric Oxide", Hepatology, Feb. 1997, pp. 361-367, vol. 25, Issue 2.
Chavez, E. et al., "Resveratrol prevents fibrosis, NF-kappaB activation and TGF-beta increases induces by chronic CCl4 treatment in rats", Journal of Applied Toxicology, Jan. 2008, pp. 35-43, vol. 28, Issue 1.
Chen, A. et al., "The antioxidant (−)-epigallocatechin-3-gallate inhibits activated hepatic stellate cell growth and suppresses acetaldehyde-induced gene expression", Biochemical Journal, Dec. 15, 2002, pp. 695-704, vol. 368, Part 3.
De Bleser, P.J. et al., "Glutathione Levels Discriminate Between Oxidative Stress and Transforming Growth Factor-beta Signaling in Activated Rat Hepatic Stellate Cells", The Journal of Biological Chemistry, Nov. 26, 1999, pp. 3381-3387, vol. 274, Issue 48.
Dröge, W., "Free radicals in the physiological control of cell function", Physiology Reviews, Jan. 1, 2002, pp. 47-95, vol. 82, Issue 1.
Elsharkawy, A.M. and Mann, D.A., "Nuclear Factor-kappaB and the Hepatic Inflammation-Fibrosis-Cancer Axis", Hepatology, Aug. 2007, pp. 590-597, vol. 46, Issue 2.
Floyd, R.A., "Nitrones as therapeutics in age-related diseases", Aging Cell, Feb. 2006, pp. 51-57, vol. 5, Issue 1.
Frei, B. and Higdon, J.V., "Antioxidant Activity of Tea Polyphenols In Vivo: Evidence from Animal Studies", Journal of Nutrition, Oct. 1, 2003, pp. 3275S-3284S, vol. 133, Issue 10.
Friedman, S.L., "Liver fibrosis—from bench to bedside", Journal of Hepatology, 2003, pp. S38-S53, vol. 38, Supplement 1.
Yumei, F. et al., "The antifibrogenic effect of (−)-epigallocatechin gallate results from the induction of de novo synthesis of glutathione in passaged rat hepatic stellate cells", Laboratory Investigation, Jul. 2006, pp. 697-709, vol. 86, Issue 7.
Galli, A. et al., "Oxidative Stress Stimulates Proliferation and Invasiveness of Hepatic Stellate Cells via a MMP2Mmediated Mechanism", Hepatology, May 2005, pp. 1074-1084, vol. 41, Issue 5.
Harrison, S.A. et al., "Vitamin E and vitamin C treatment improves fibrosis in patients with non-alcoholic steatohepatitis Vitamin Treatment in patients with NASH.", The American Journal of Gastroenterology, Nov. 2003, pp. 2485-2490, vol. 98, Issue 11.
Halliwell, B. and Whiteman, M., "Measuring reactive species and oxidative damage in vivo and in cell culture: how should you do it and what do the results mean?", British Journal of Pharmacology, May 2004, pp. 231-255, vol. 142, Issue 2.
Harlow, K.J. et al., "Convenient and General Synthesis of Symmetric N,N'-Disubstituted Imidazolium Halides", Synthesis, Jun. 1996, pp. 697-698, Issue 6.
Hou, Z. et al., "Mechanism of Action of ( )-Epigallocatechin-3-Gallate: Auto-oxidation-Dependent Inactivation of Epidermal Growth Factor Receptor and Direct Effects on Growth Inhibition in Human Esophageal Cancer KYSE 150 Cells", Cancer Research, Sep. 1, 2005, pp. 8049-8056, vol. 65, Issue 17.
Kawada, N. et al., "Effect of Antioxidants, Resveratrol, Quercetin, and N-Acetylcysteine, on the Functions of Cultured Rat Hepatic Stellate Cells and Kupffer Cells", Hepatology, May 1998, pp. 1265-1274, vol. 27, Issue 5.
Keum, Y.-S. et al., "3-Morpholinoproply isothiocyanate (3MP-ITC) is a novel synthetic isothiocyanate that strongly induces the antioxidant response element (ARE)-dependent Nrf2-mediated detoxifying/antioxidant enzymes in vitro and in vivo", Carcinogenesis, 2008, pp. 594-599, vol. 29, Issue 3.
Lin, L.-C. et al., "Determination of (−)-epigallocatechin gallate in rat blood by microdialysis coupled with liquid chromatography", Journal of Chromatography A, Apr. 2, 2004, pp. 125-128, vol. 1032, Issues 1-2.
Liu, S.-L. et al., "Vitamin E therapy of acute CCl4-induced hepatic injury in mice is associated with inhibition of nuclear factor-kappaB binding", Hepatology, Nov. 1995, pp. 1474-1481, vol. 22, Issue 5.
Lu, G. et al., "Interferon-alpha enhances biological defense activities against oxidative stress in cultured rat hepatocytes and hepatic stellate cells", The Journal of Medical Investigation, Aug. 2002, pp. 172-181, vol. 49, Issues 3-4.
Maples, K.R. et al., "Nitrone-Related Therapeutics: Potential of NXY-059 for the Treatment of Acute Ischaemic Stroke", CNS Drugs, 2004, pp. 1071-1084, vol. 18, Issue 15.
Maubach, G. et al., "GFAP promoter directs lacZ expression specifically in a rat hepatic stellate cell line", World Journal of Gastroenterology, Feb. 7, 2006, pp. 723-730, vol. 12, Issue 5.
Meurer, S.K. et al., "N-Acetyl-L-cysteine suppresses TGF-beta signaling at distinct molecular steps: The biochemical and biological efficacy of a multifunctional, antifibrotic drug", Biochemical Pharmacology, Oct. 1, 2005, pp. 1026-1034, vol. 70, Issue 7.
Nakamuta, M. et al., "Epigallocatechin-3-gallate, a polyphenol component of green tea, suppresses both collagen production and collagenase activity in hepatic stellate cells", International Journal of Molecular Medicine, Oct. 2005, pp. 677-681, vol. 16, No. 4.
Naugler, W.E. et al., "Gender Disparity in Liver Cancer Due to Sex Differences in MyD88-dependent IL-6 production", Science, Jul. 6, 2007, pp. 121-124, vol. 317, No. 5834.
Olmos, G. et al., "Protection by imidazol(ine) drugs and agmatine of glutamate-induced neurotoxicity in cultured cerebellar granule cells through blockade of NMDA receptor", British Journal of Pharmacology, Jul. 1999, pp. 1317-1326, vol. 127, Issue 6.
Orr, J.G. et al., "Mechanism of action of the antifibrogenic compound gliotoxin in rat liver cells", Hepatology, Jul. 2004, pp. 232-242, vol. 40, Issue 1.
Padillo, F.J. et al., "Melatonin prevents oxidative stress and hepatocyte cell death induced by experimental cholestasis", Free Radical Research, Jul. 2004, pp. 697-704, vol. 38, Issue 7.
Parola, M. et al., "Induction of procollagen type I gene expression and synthesis in human hepatic stellate cells by 4-hydroxy-2,3-nonenal and other 4-hydroxy-2,3-alkenals is related to their molecular structure", Biochemical and Biophysical Research Communications, May 15, 1996, pp. 261-264, vol. 222, Issue 2.
Peng, J. et al., "Superoxide Dismutase/Catalase Mimetics are Neuroprotective against Selective Paraquat-mediated Dopaminergic Neuron Death in the Substantial Nigra: Implications for Parkinson disease", The Journal of Biological Chemistry, Aug. 12, 2005, pp. 29194-29198, vol. 280, Issue 32.
Smart, D.E. et al., "JunD Regulates Transcription of the Tissue Inhibitor of Metalloproteinases-1 and Interleukin-6 Genes in Activated Hepatic Stellate Cells", The Journal of Biological Chemistry, Jun. 29, 2001, pp. 24414-24421, vol. 276, Issue 26.
Tsukamoto, H. et al., "Roles of oxidative stress in activation of Kupffer and Ito cells", Journal of Gastroenterology and Hepatology, Sep. 1995, pp. S50-S53, vol. 10, Issue S1.
Tsukamoto, H., "Cytokine Regulation of Hepatic Stellate Cell in Liver Fibrosis", Alcoholism: Clinical and Experimental Research, May 1999, pp. 911-916, vol. 23, Issue 5.
Vasiliou, V. et al., "Involvement of p65 in the Regulation of NF-kappaB in Rat Hepatic Stellate Cells during Cirrhosis", Biochemical and Biophysical Research Communications, Jul. 5, 2000, pp. 546-550, vol. 273, Issue 2.

(56) References Cited

OTHER PUBLICATIONS

Weiskirchen, R. and Gressner, A.M., "Isolation and Culture of Hepatic Stellate Cells", Methods in Molecular Medicine—Fibrosis Research: Methods and Protocols, 2005, pp. 99-113, vol. 117.

Whalen, R. et al., "Activation of Rat Hepatic Stellate Cells Leads to Loss of Glutathione S-Transferases and Their Enzymatic Activity Against Products of Oxidative Stress", Hepatology, Oct. 1999, pp. 927-933, vol. 30, Issue 4.

Zhang, C.Y. and Zhuo, L., "Epigallocatechin gallate and genistein attenuate glial fibrillary acidic protein elevation induced by fibrogenic cytokines in hepatic stellate cells", International Journal of Molecular Medicine, Dec. 2006, pp. 1141-1151, vol. 18, No. 6.

Agarwal, M.L. et al., "The p53 network", The Journal of Biological Chemistry, Jan. 2, 1998, pp. 1-4, vol. 273, Issue 1.

Arnoult, D. et al., "Mitochondrial release of AIF and EndoG requires caspase activation downstream of Bax/Bak-mediated permeabilization", The EMBO Journal, Sep. 1, 2003, pp. 4385-4399, vol. 22, Issue 17.

Anderson, C.W. and Appella, E., "Signaling to the p53 tumor suppressor through pathways activated by genotoxic and non-genotoxic stresses", in: RA Bradshaw, E.A. Dennis (Eds.), Handbook of cell signaling, vol. 3 Academic Press, New York, 2003.

Appella, E. and Anderson, C.W., "Post-translational modifications and activation of p53 by genotoxic stresses", European Journal of Biochemistry, May 2001, pp. 2764-2772, vol. 268, Issue 10.

Ariizumi, S. et al., "Histopathologic differentiation of the main nodule determines outcome after hepatic resection for synchronous multi-centric hepatocellular carcinomas", Hepato-Gastroenterology, Mar.-Apr. 2004, pp. 500-504, vol. 51, Issue 56.

Avila, M.A. et al., "New therapies for hepatocellular carcinoma", Oncogene, Jun. 2006, pp. 3866-3884, vol. 25, Issue 27.

Banin, S. et al., "Enhanced phosphorylation of p53 by ATN in response to DNA damage", Science, Sep. 11, 1998, pp. 1674-1677, vol. 281, No. 5383.

Bataller, R. and Brenner, D.A., "Liver fibrosis", The Journal of Clinical Investigation, Feb. 1, 2005, pp. 209-218, vol. 115, Issue 2.

Bergamo, A. and Sava, G., "Ruthenium complexes can target determinants of tumour malignancy", Dalton Transactions, 2007, pp. 1267-1272, Issue 13.

Boydston, A.J. et al., "A Modular Approach to Main-Chain Organometallic Polymers", Journal of the American Chemical Society, Sep. 14, 2005, pp. 12496-12496, vol. 127, Issue 36.

Bykov, V.J.N. et al., "Restoration of the tumor suppressor function to mutant p53 by a low- molecular-weight compound", Nature Medicine, Mar. 2002, pp. 282-288, vol. 8, Issue 3.

Canman, C.E. et al. "Activation of the ATM kinase by ionizing radiation and phosphorylation of p53", Science, Sep. 11, 1998, pp. 1677-1679, vol. 281, No. 5383.

Caron de Fromentel, C. et al., "Restoration of transcriptional activity of p53 mutants in human tumor cells by intracellular expression of anti-p53 single chain Fv fragments", Oncogene, Jan. 1999, pp. 551-557, vol. 18, Issue 2.

Chan, D.W. et al., "Purification and Characterization of ATM from Human Placenta", The Journal of Biological Chemistry, Mar. 17, 2000, pp. 7803-7810, vol. 275, Issue 11.

Chianese, A.R. and Crabtree, R.J., "Axially Chiral Bidentate N-Heterocyclic Carbene Ligands Derived from BINAM: Rhodium and Iridium Complexes in Asymmetric Ketone", Organometallics, Aug. 29, 2005, pp. 4432-4436, vol. 24, Issue 18.

Das, A. et al. "Garlic Compounds Generate Reactive Oxygen Species Leading to Activation of Stress Kinases and Cysteine Proteases for Apoptosis in Human Glioblastoma T98G and U87MG Cells", Cancer, Sep. 1, 2007, pp. 1083-1095, vol. 110, Issue 5.

Deuffic, S. et al., "Trends in primary liver cancer", The Lancet, Jan. 17, 1998, pp. 214-215, vol. 351, Issue 9097.

Dominianni, S.J. and Yen, T.T., "Oral hypoglycemic agents. Discovery and structure-activity relationships of phenacylimidazolium halides", Journal of Medicinal Chemistry, Oct. 1989, pp. 2301-2306, vol. 32, Issue 10.

El-Serag, H.B. et al., "The Continuing Increase in the Incidence of Hepatocellular Carcinoma in the United States: An Update", Annals of Internal Medicine, Nov. 18, 2003, pp. 817-823, vol. 139, Issue 10.

El-Serag, H.B. and Mason, A.C., "Rising incidence of hepatocellular carcinoma in the United States", The New England Journal of Medicine, Mar. 11, 1999, pp. 745-750, vol. 340, No. 10.

Fei, P. and El-Diery, W.S., "P53 and radiation responses", Oncogene, Sep. 2003, pp. 5774-5783, vol. 22, Issue 37.

Friedler, A. et al., "A peptide that binds and stabilizes p53 core domain: Chaperone strategy for rescue of oncogenic mutants", Proceedings of the National Academy of Sciences of the United States of America, Jan. 22, 2002, pp. 937-942, vol. 99, Issue 2.

Friedman, S.L., "Hepatic Stellate Cells: Protean, Multifunctional, and Enigmatic Cells of the Liver", Physiological Reviews, Jan. 1, 2008, pp. 125-172, vol. 88, Issue 1.

Friedman, S.L., "Mechanisms of Hepatic Fibrogenesis", Gastroenterology, May 2008, pp. 1655-1669, vol. 134, Issue 6.

Giaccia, A.J. and Kastan, M.B., "The complexity of p53 modulation: emerging patterns from divergent signals", Genes & Development, Oct. 1, 1998, pp. 2973-2983, vol. 12, Issue 19.

Hofseth, L.J. et al., "Nitric oxide—induces cellular stress and p53 activation in chronic inflammation", Proceedings of the National Academy of Sciences of the United States of America, Jan. 7, 2003, pp. 143-148, vol. 100, Issue 1.

Hollstein, M. et al., "p53 mutations in human cancers", Science, Jul. 5, 1991, pp. 49-53, vol. 253, No. 5015.

Huang, M. and Liu, G.T., "The study of innate drug resistance of human hepatocellular carcinoma Be17402 cell line", Cancer Letters, Dec. 11, 1998, p. 97-105, vol. 135, Issue 1.

Hupp, T.R. et al., "Small Peptides Activate the Latent Sequence-Specific DNA Binding Function of p53", Cell, Oct. 20, 1995, pp. 237-245, vol. 83, Issue 2.

Hussain, S.P. et al., "Radical causes of cancer", Nature Reviews Cancer, Apr. 2003, pp. 276-285, vol. 3, Issue 4.

Iredale, J.P., "Models of liver fibrosis: exploring the dynamic nature of inflammation and repair in a solid organ", The Journal of Clinical Investigation, Mar. 1, 2007, pp. 539-548, vol. 117, Issue 3.

Iredale, J.P., "Cirrhosis: new research provides a basis for rational and targeted treatments", BMJ, Jul. 19, 2003, pp. 143-147, vol. 327, No. 7407.

Jakubikova, J. and Sedlák, J., "Garlic-derived organosufides induce cytotocity, apoptosis, cell cycle arrest and oxidative stress in human colon carcinoma cell line", Neoplasma, 2006, pp. 191-199, vol. 53, Issue 3.

Kato, A. et al., "Multidrug resistance gene (MDR-1) expression as a useful prognostic factor in patients with human hepatocellular carcinoma after surgical resection", Journal of Surgical Oncology, Oct. 2001, pp. 110-115, vol. 78, Issue 2.

Katzenellenbogen, M. et al., "Molecular mechanisms of the chemopreventive effect on hepatocellular carcinoma development in Mdr2 knockout mice", Molecular Cancer Therapeutics, Apr. 2007, pp. 1283-1291, vol. 6, Issue 4.

Kluck, R.M. et al., "The release of cytochrome c from mitochondria: A primary site for Bcl-2 regulation of apoptosis", Science, Feb. 21, 1997, pp. 1132-1136, vol. 275, No. 5303.

Ko, L.J. and Prives, C., "p53: puzzle and paradigm", Genes & Development, May 1, 1996, pp. 1054-1072, vol. 10, Issue 9.

Llovet, J.M. et al., "Hepatocellular carcinoma", The Lancet, Dec. 6, 2003, pp. 1907-1917, vol. 362, Issue 9399.

Lorenzo, H.K. and Susin, S.A., "Therapeutic potential of AIF-mediated caspase-independent programmed cell death", Drug Resistance Updates, Dec. 2007, pp. 235-255, vol. 10, Issue 6.

Mignotte, B. and Vayssiere, J.-L., "Mitochondria and apoptosis", European Journal of Biochemistry, currently known as FEBS Journal, 1998, pp. 1-15, vol. 252, Issue 1.

Moon, W.S. and Tarnawski, A.S., "Nuclear translocation of survivin in hepatocellular carcinoma: a key to cancer cell growth?", Human Pathology, Nov. 2003, pp. 1119-1126, vol. 34, Issue 11.

Nishikawa, T. et al., "A green tea polyphenol, epigalocatechin-3-gallate, induces apoptosis of human hepatocellular carcinoma, possible through inhibition of Bcl-2 family protein", Journal of Hepatology, Jun. 2006, pp. 1074-1082, vol. 44, Issue 6.

(56) References Cited

OTHER PUBLICATIONS

Foster, B.A. et al., "Pharmacological Rescue of Mutant p53 Conformation and Function", Science, Dec. 24, 1999, pp. 2507-2510, vol. 286, No. 5449.
Parkin, D.M. et al., "Estimating the world cancer burden: Globocan 2000", International Journal of Cancer, Oct. 15, 2001, pp. 153-156, vol. 94, Issue 2.
Pilch, D.R. et al., "Charecteristics of γ-H2AX foci at DNA double stranded break sites", Biochemistry and Cell Biology, Jun. 2003, pp. 123-129, vol. 81, No. 3.
Rakoff-Nahoum, S., "Why Cancer and Inflammation?", Yale Journal of Biology and Medicine, Dec. 2006, pp. 123-130, vol. 79, Issues 304.
Saito, S. et al., "Phosphorylation Site Interdependence of Human p53 Post-translational Modifications in Response to Stress", The Journal of Biological Chemistry, Sep. 26, 2003, pp. 37536-37544, vol. 278, Issue 39.
Saito, S. et al., "ATM Mediates Phosphorylation at Multiple p53 Sites, Including ser46, in Response to Ionizing Radiation", The Journal of Biological Chemistry, Apr. 12, 2002, pp. 12491-12494, vol. 277, Issue 15.
Selivanova, G. et al., "Restoration of the growth suppression function of mutant p53 by a synthetic peptide derived from the p53 C-terminal domain", Nature Medicine, Jun. 1997, pp. 632-638, vol. 3, Issue 6.
Shieh, S.Y. et al., "DNA Damage-Induced Phosphorylation of p53 Alleviates Inhibition by MDM2", Cell, Oct. 31, 1997, pp. 325-334, vol. 91, Issue 3.
Siliciano, J.D. et al., "DNA damage induces phosporylation of aminoterminus of p53", Genes & Development, Dec. 15, 1997, pp. 3471-3481, vol. 11, Issue 24.
Smith, G.C.M. et al., "Purification of DNA binding properties of ataxia-telangiectasia gene product ATM", Proceedings of the National Academy of Sciences of the United States of America, Sep. 28, 1999, pp. 11134-11139, vol. 96, Issue 20.
Taylor-Robinson, S.D. et al., "Increase in primary liver cancer in the UK, 1979-1994", The Lancet, Oct. 18, 1997, pp. 1142-1143, vol. 350, Issue 9085.
Thomas, M.B. and Zhu, A.X., "Hepatocellular Carcinoma: The Need for Progress", Journal of Clinical Oncology, May 1, 2005, pp. 2892-2899, vol. 23, No. 13.
Thorgeirsson, S.S. and Grisham, J.W., "Molecular pathogenesis of human heptocellular carcinoma", Nature Genetics, Aug. 2002, pp. 339-346, vol. 31, No. 4.
Tonini, G. et al., "Nuclear and cytoplasmic expression of suvivin in 67 surgically resected pancreatic cancer patients", British Journal of Cancer, Jun. 2005, pp. 2225-2232, vol. 92, Issue 12.
Váli, L. et al., "Oxidative stress with altered element content and decreased ATP level of erythrocytes in hepatocellular carcinoma and colorectal liver metastases", European Journal of Gastroenterology & Hepatology, May 2008, pp. 393-398, vol. 20, Issue 5.
Valko, M. et al., "Role of oxygen radical in DNA damage and cancer incidence", Molecular and Cellular Biochemistry, Nov. 2004, pp. 37-56, vol. 266, Issues 1-2.
Vogelstein, B. et al., "Surfing the p53 network", Nature, Nov. 16, 2000, pp. 307-310, vol. 408, No. 6810.
Wahl, G.M. and Carr, A.M., "The evolution of diverse biological responses, to DNA damage: insights from yeast and p53", Nature Cell Biology, Dec. 2001, pp. E277-E286, vol. 3, Issue 12.
Wie, M.C. et al., "Proapoptotic BAX and BAK: A Requisite Gateway to Mitochondrial Dysfunction and Death", Science, Apr. 27, 2001, pp. 727-730, vol. 292, No. 5517.
Zhang, Y. et al., "The First N-Heterocyclic Carbene-Based Nickel Catalyst for C-S Coupling", Organic Letters, Aug. 30, 2007, pp. 3495-3498, vol. 9, Issue 18.
Zhao, L. et al., "Imidazolium Salts: A Mild Reducing and Antioxidative Reagent", Journal of the American Chemical Society, Sep. 24, 2008, pp. 12586-12587, vol. 130, Issue 38.
Beyaz, A. et al., "Synthesis and CMC studies of 1-methyl-3-(pentaflourophenyl) imidazolium quaternary salts", Colloids and Surfaces B: Biointerfaces, Jul. 15, 2004, pp. 71-74, vol. 36, Issue 2.
Galanakis, D. et al., "Synthesis and Structure—Activity Relationships of Dequalinium Analogues as K+ Channel Blockers. Investigations of the Role of the Charged Heterocycle", Journal of Medicinal Chemistry, Feb. 1995, pp. 595-606, vol. 38, Issue 4.
Ionic Liquids Database—(IL Thermo) http//ilthermo.boulder.nist.gov/ILThermo/ionall.uix.do?event=goto&source=ionasalIV.htm. Sep. 29, 2006.
io-li-tec (Ionic Liquids Technologies) http//www.iolitec.de/ionic_e.htm. Oct. 10, 2007.
International Preliminary Report on Patentability issued in PCT Application No. PCT-SG2009-000037 dated Jan. 8, 2010.
International Search Report and Written Opinion issued in PCT-SG2009-000037 (date of mailing May 4, 2009).
International Search Report and Written Opinion issued in PCT-SG2009-000112 (date of mailing Jul. 6, 2009).
International Preliminary Report on Patentability issued in PCT Application No. PCT-SG2009-000112 dated Jul. 5, 2010.
Response to Written Opinion & Demand filed Nov. 30, 2009 in PCT Application No. PCT-SG2009-000037.
Second Written Opinion issued in PCT-SG2009-000112 (date of mailing Feb. 26, 2010).
Extended European Search Report issued in EP Application No. 09706910.8 dated Nov. 18, 2011.
Gong, X. et al., "Large substituent containing porphyrin derivative, its preparation and application as small molecular antioxidant", HCAPLUS, Oct. 22, 2003, XP002627466.
Frade, R.F.M. et al., "Effect of ionic liquids on human colon carcinoma HT-29 and CaCo-2 cell lines", Green Chemistry, Jan. 1, 2007, pp. 873-877, vol. 9, Issue 8.
Hindi, K.M. et al., "Synthesis, Stability, and Antimicrobial Studies of Electronically Tuned Silver Acetate N-Heterocyclic Carbenes", Journal of Medicinal Chemistry, Mar. 1, 2008, pp. 1577-1583, vol. 51, Issue 6.
1st Office Action issued in Chinese Patent Application No. 200980112080.7 dated Feb. 16, 2012.
2nd Office Action issued in corresponding Chinese Patent Application No. 200980112080.7 dated Dec. 26, 2012.
Notice of Reasons for Rejection dated Jun. 25, 2013 issued in corresponding JP Application No. 2010-544928.
Frade, et al., "Effect of Ionic Liquids on Human Colon Carcinoma HT-29 and CaCo-2 Cell Lines," Green Chem., 2007, 9, p. 873-877.
Notice of Reasons for Rejection dated Dec. 10, 2013 issued in corresponding JP Application No. 2010-544928.

* cited by examiner a
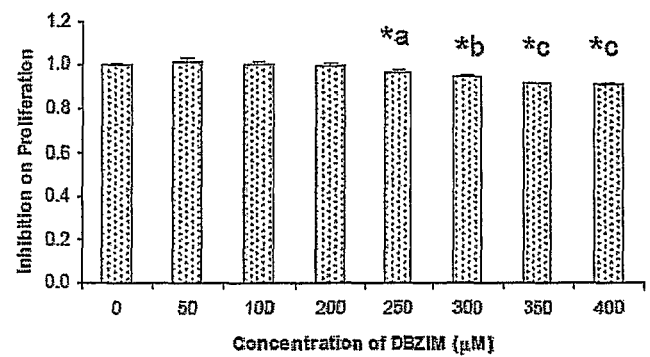
b
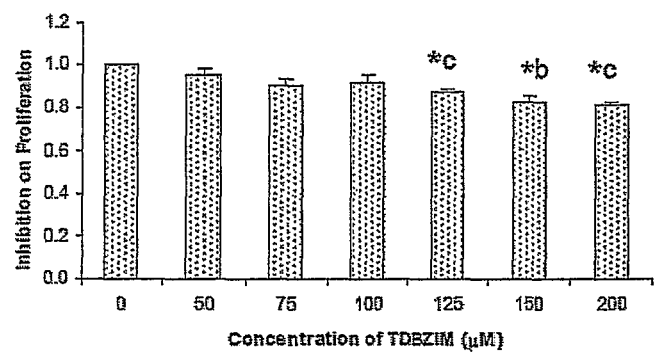
FIGURE 1 a
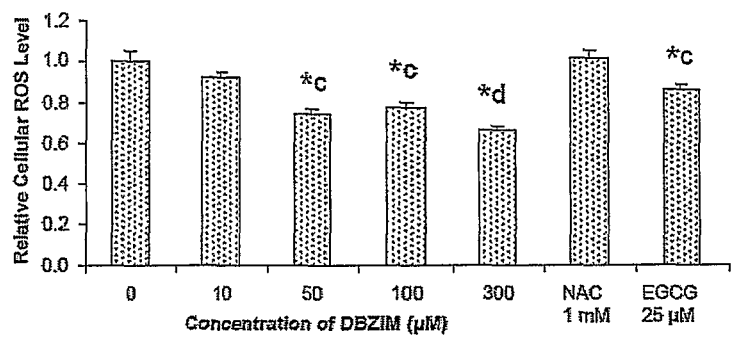
b
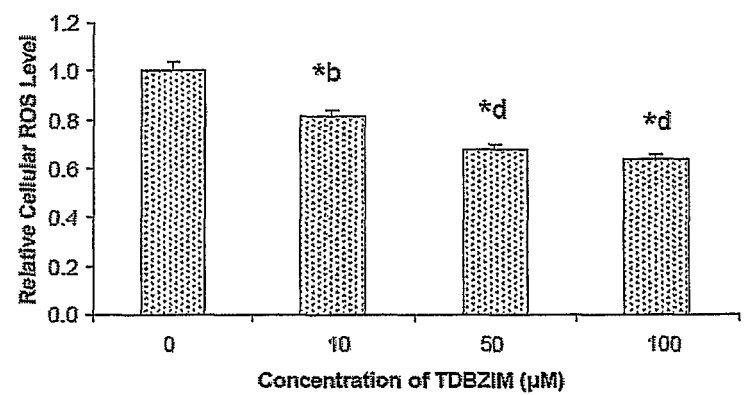
FIGURE 2 a
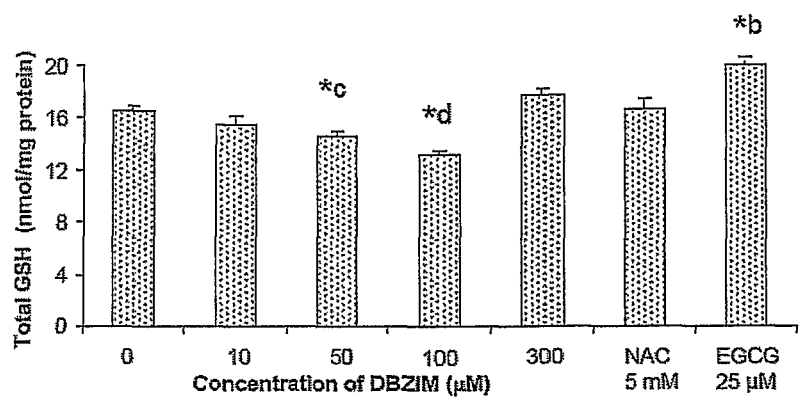
b
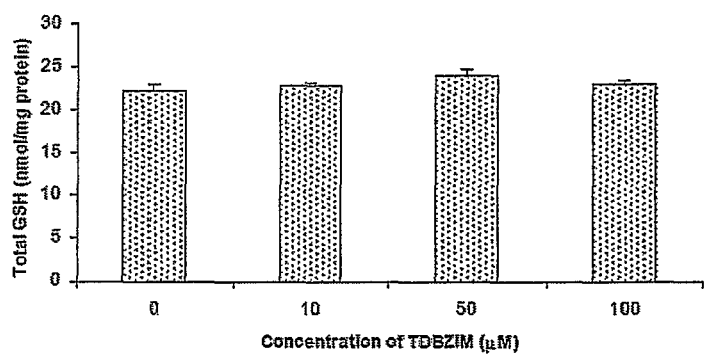
FIGURE 3 c
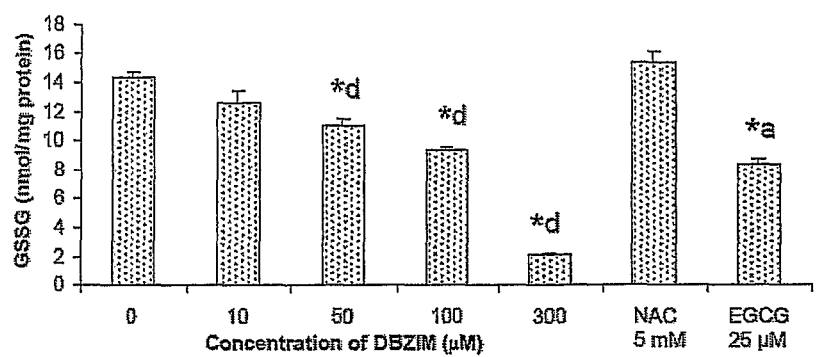
d
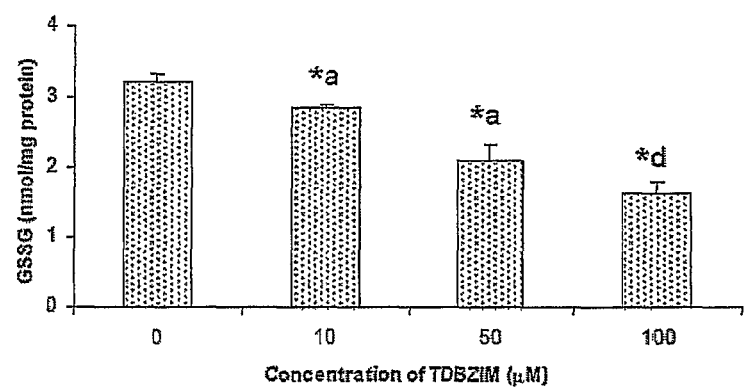
FIGURE 3 Continued e
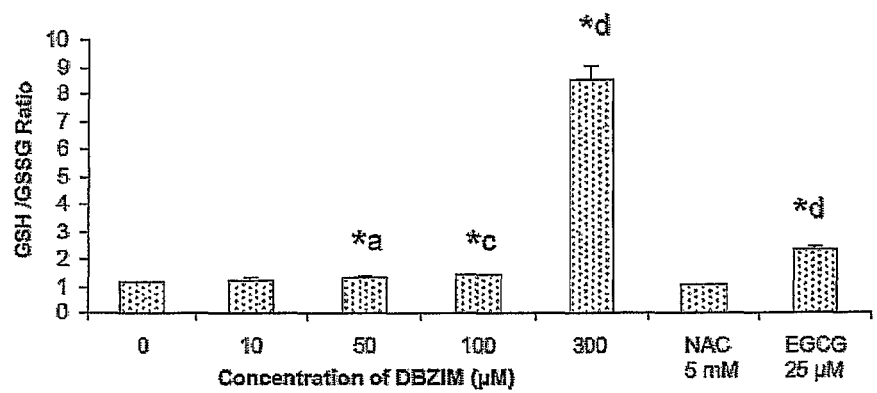
f
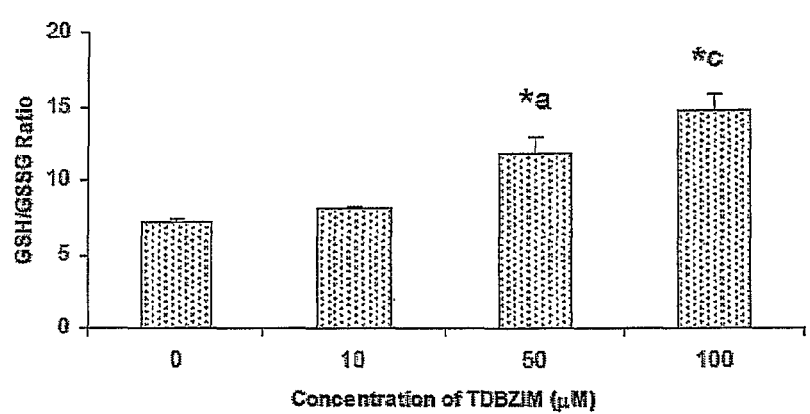
FIGURE 3 Continued

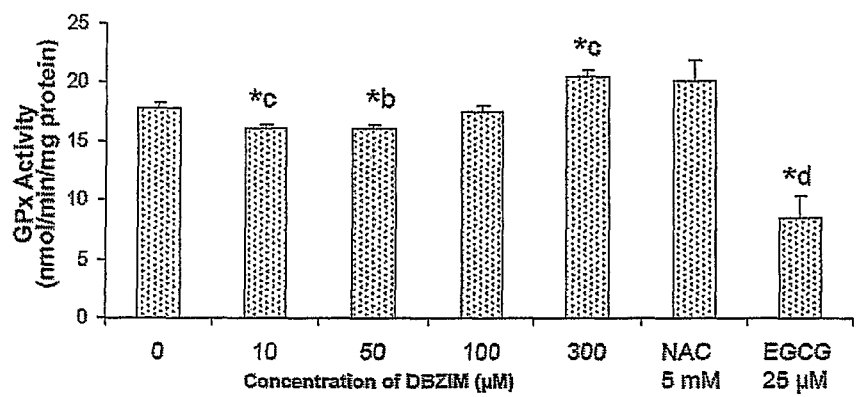
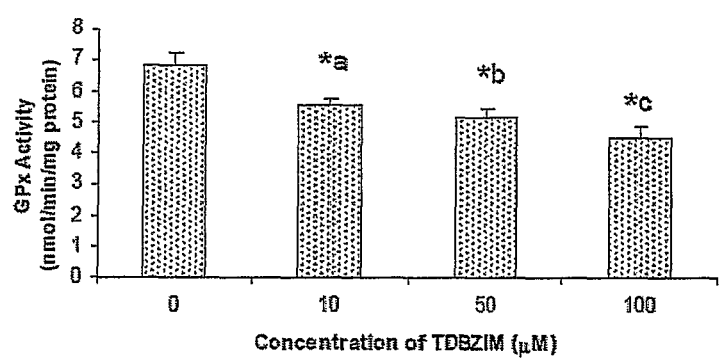
FIGURE 4 c
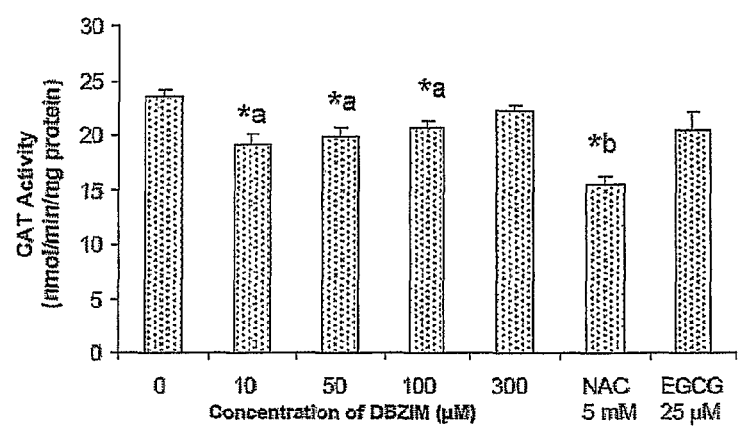
d
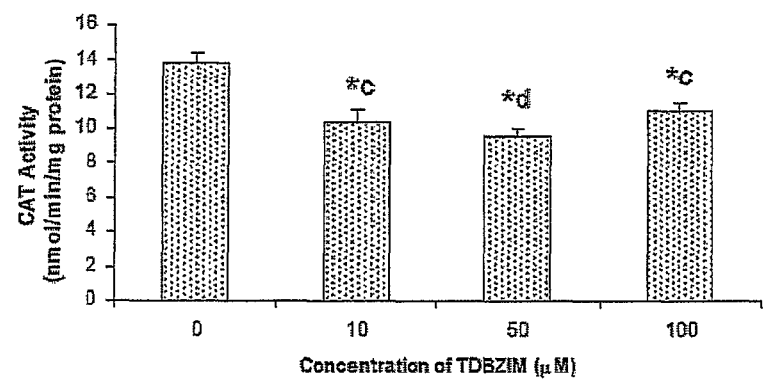
FIGURE 4 Continued

E
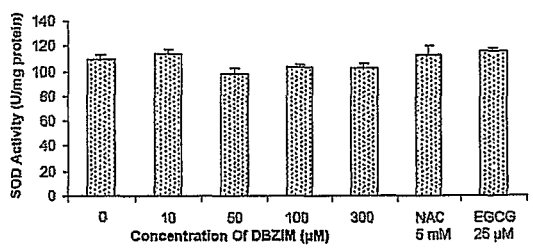
F
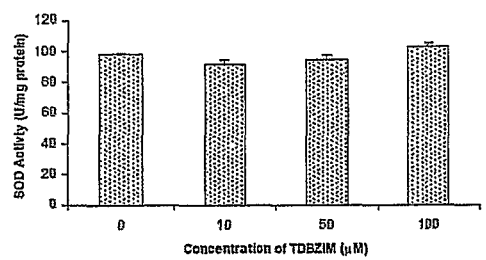
G
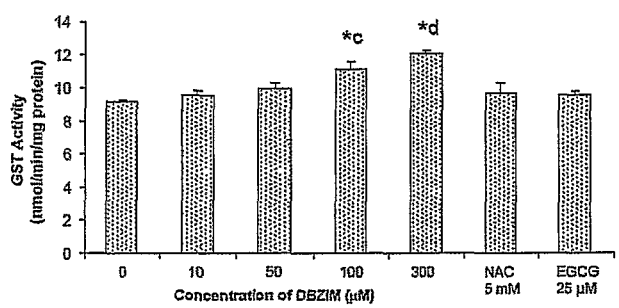
FIGURE 4 Continued

A

Fig. 7a
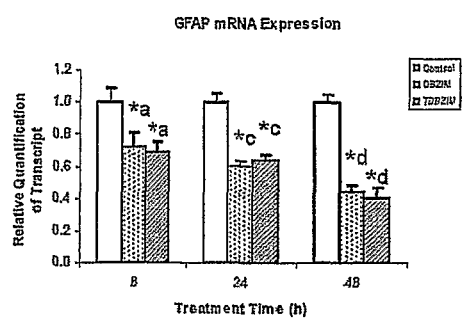
Fig. 7b
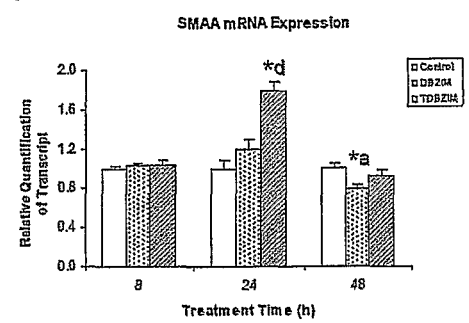
Fig. 7c
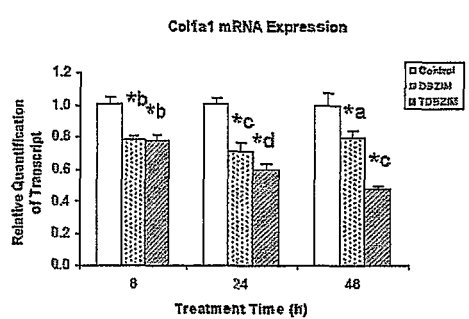
Fig. 7d
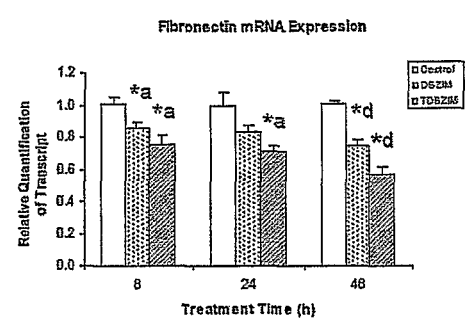
FIGURE 7

Fig. 9a
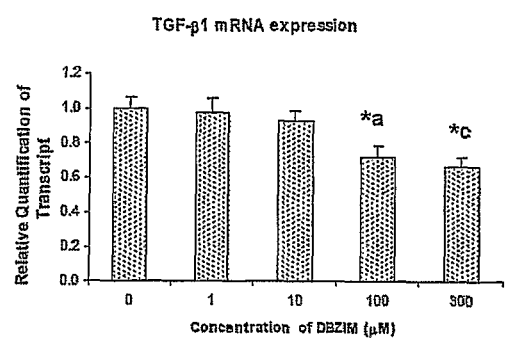
Fig. 9b
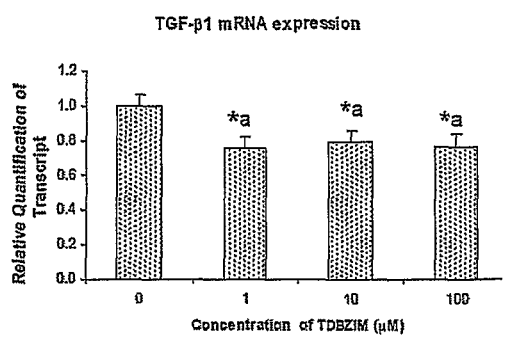
Fig. 9c
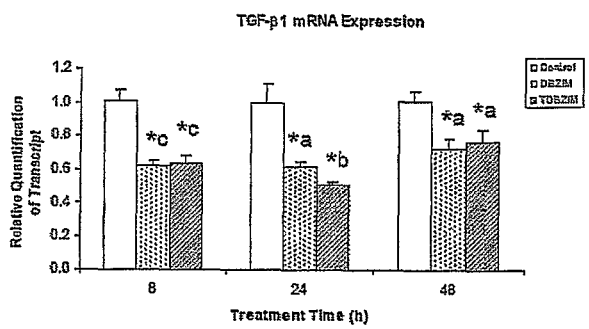
FIGURE 9

Fig. 10a
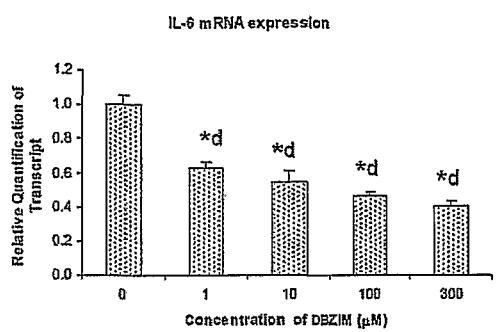
Fig. 10b
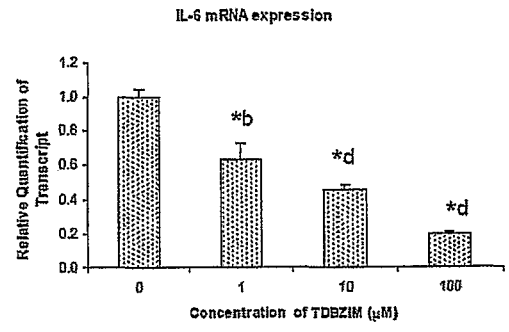
Fig. 10c
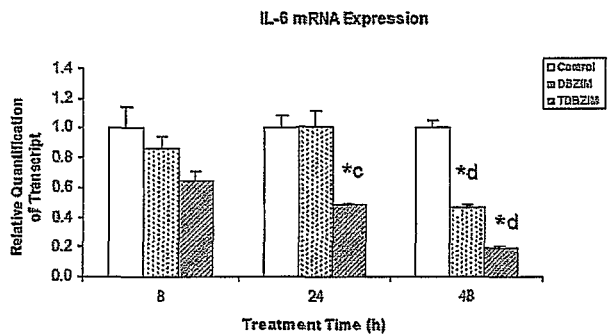
FIGURE 10

Fig. 14a
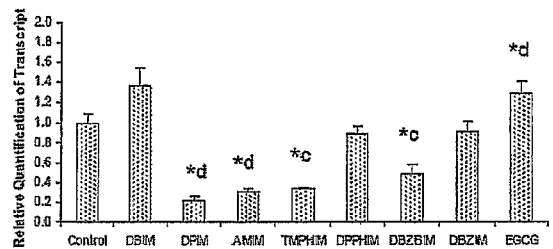
Fig. 14b
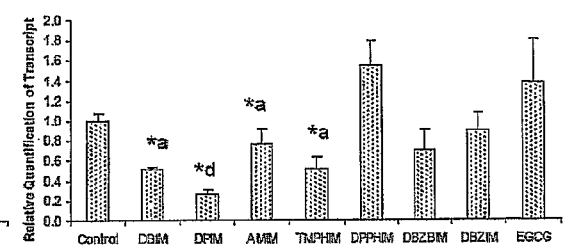
Fig. 14c
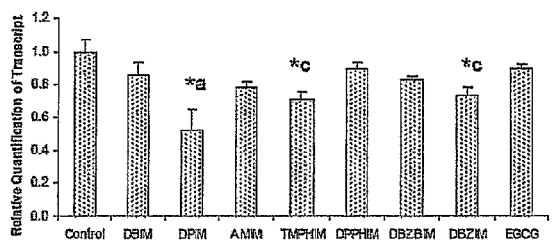
Fig. 14d
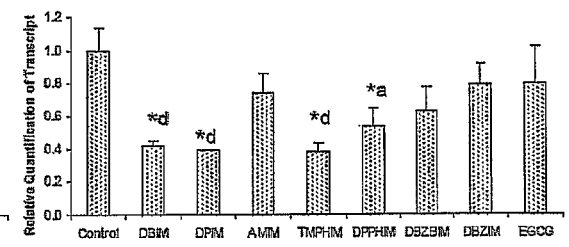
FIGURE 14

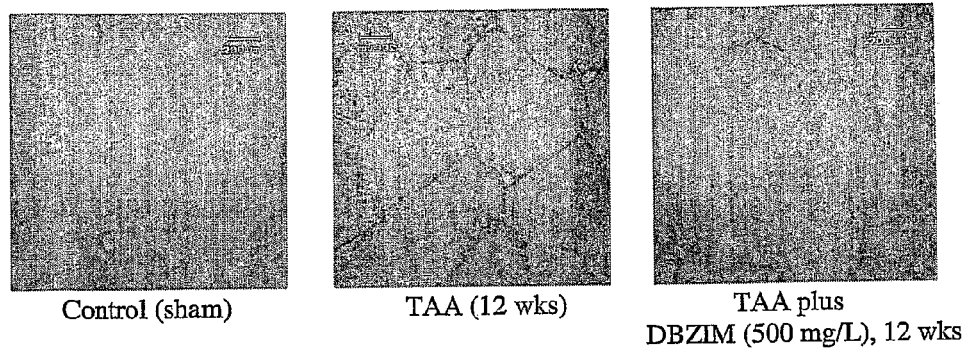
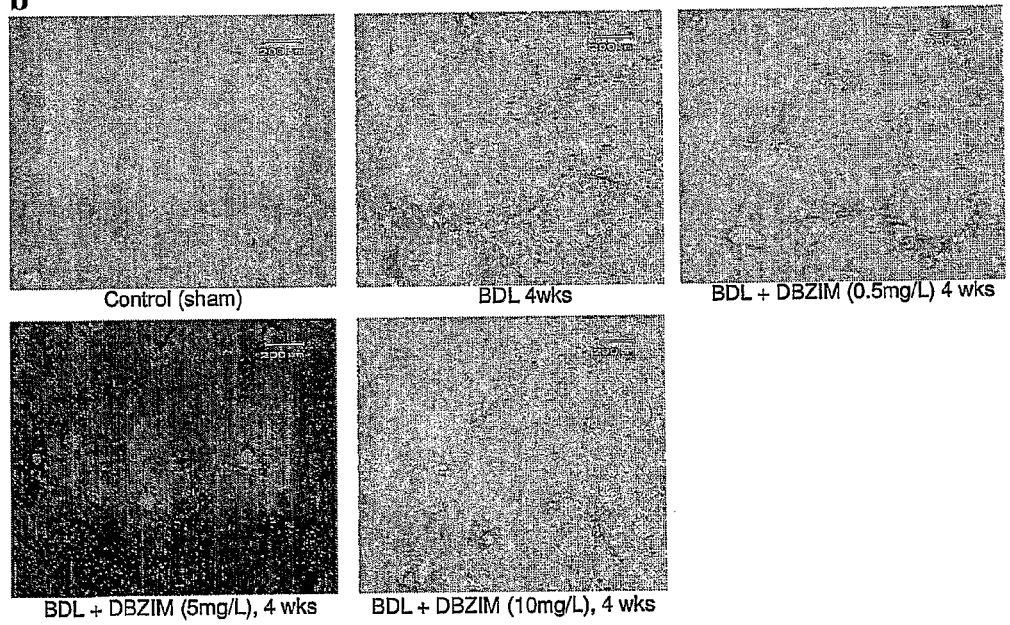
FIGURE 15 c

Control (sham)　　　BDL 4 wks　　　BDL + DPIM (1g/L), 4 wks

A
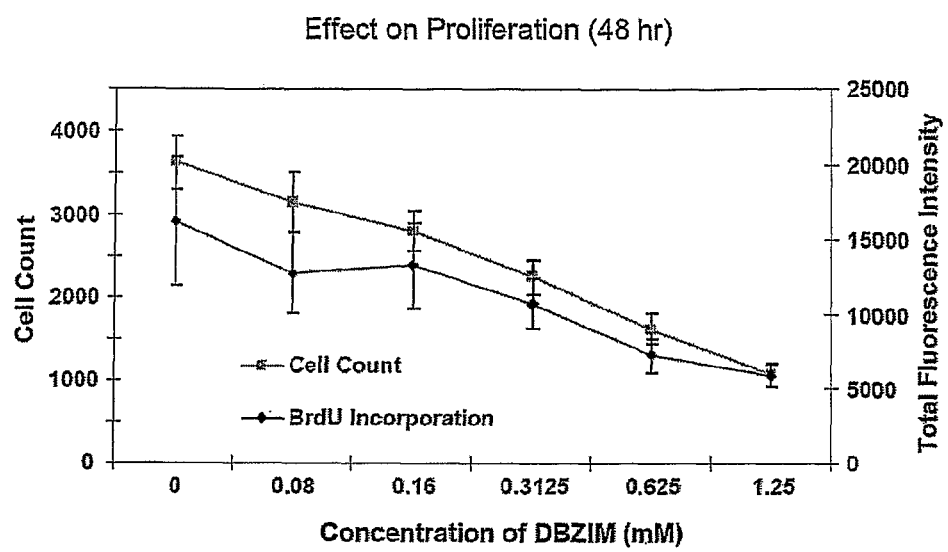
B
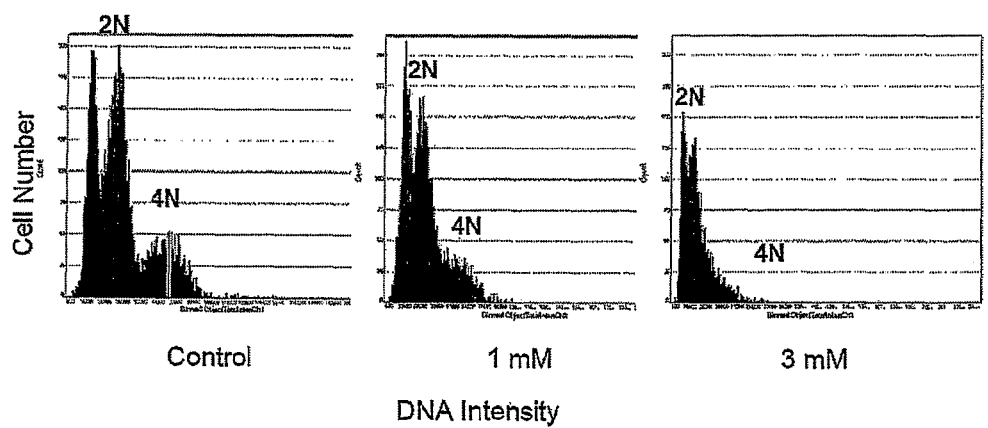
FIGURE 21

A
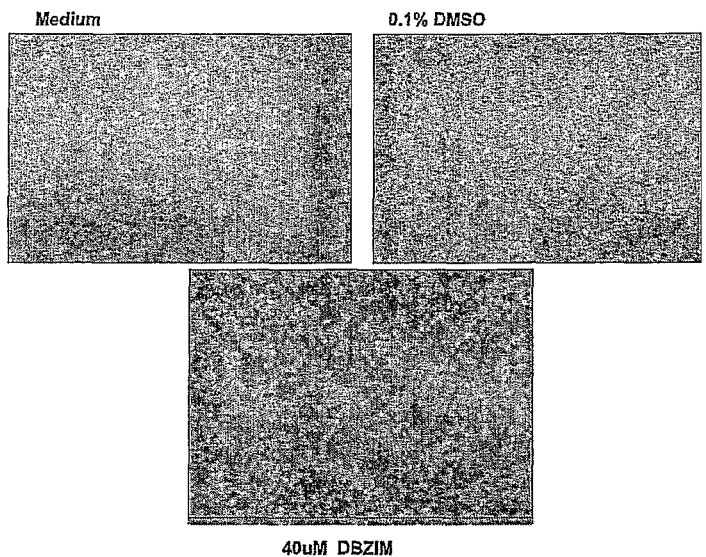
B
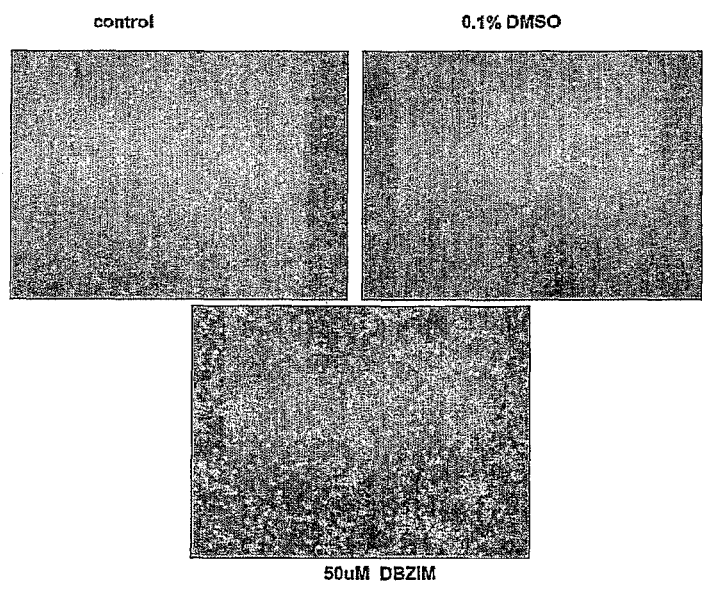
FIGURE 29

A
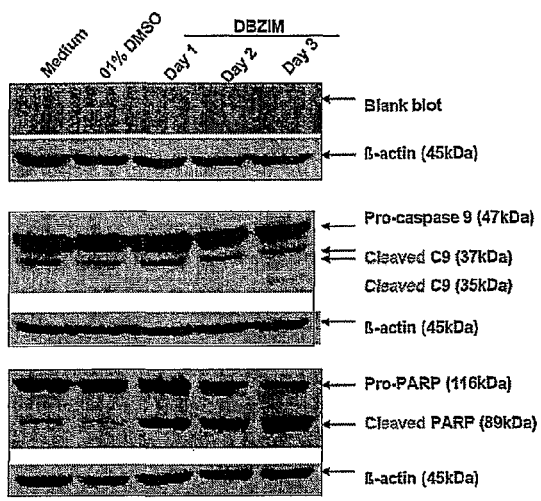
B
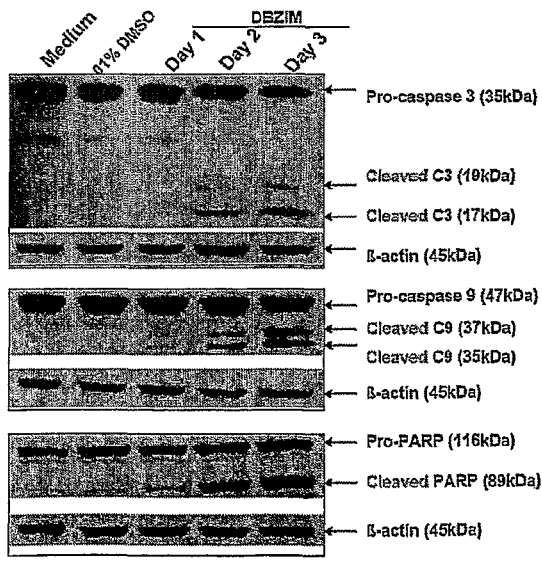
FIGURE 31

A
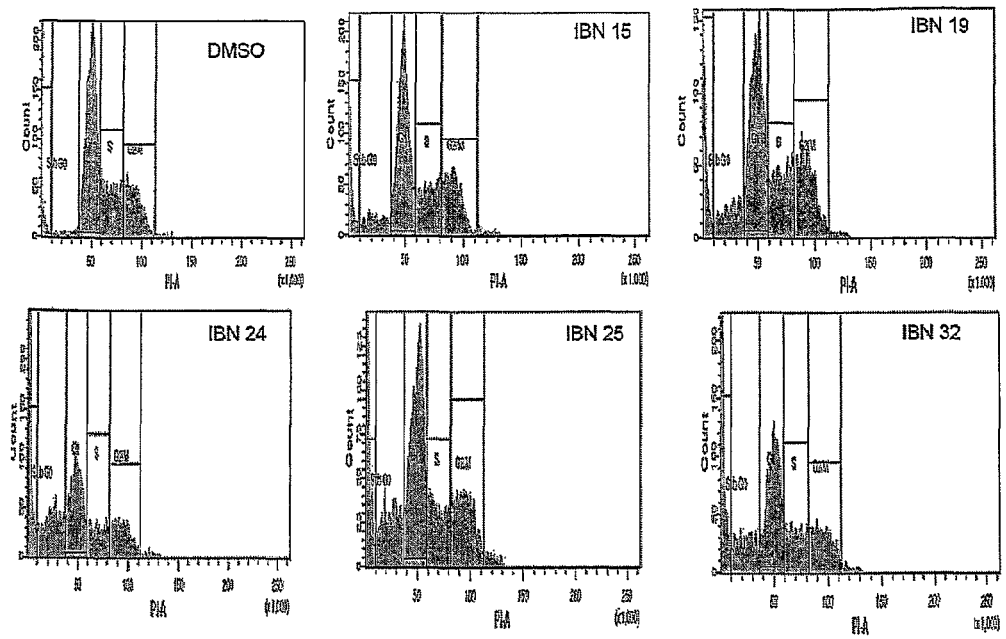
B
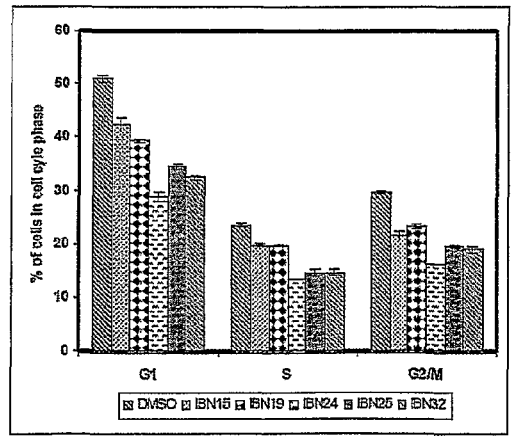
C
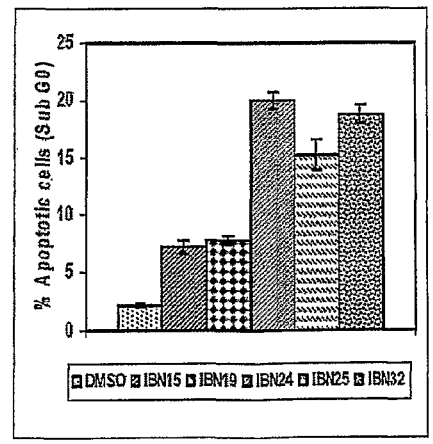
FIGURE 37

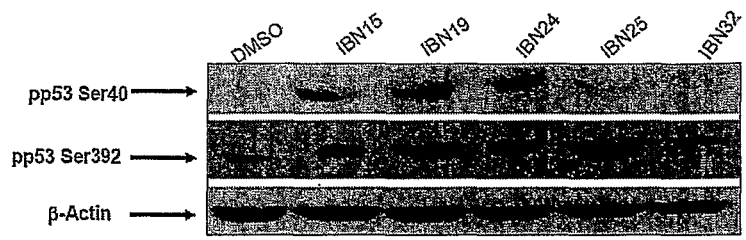
FIGURE 40
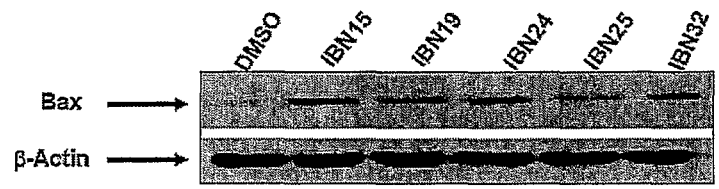
FIGURE 41

A
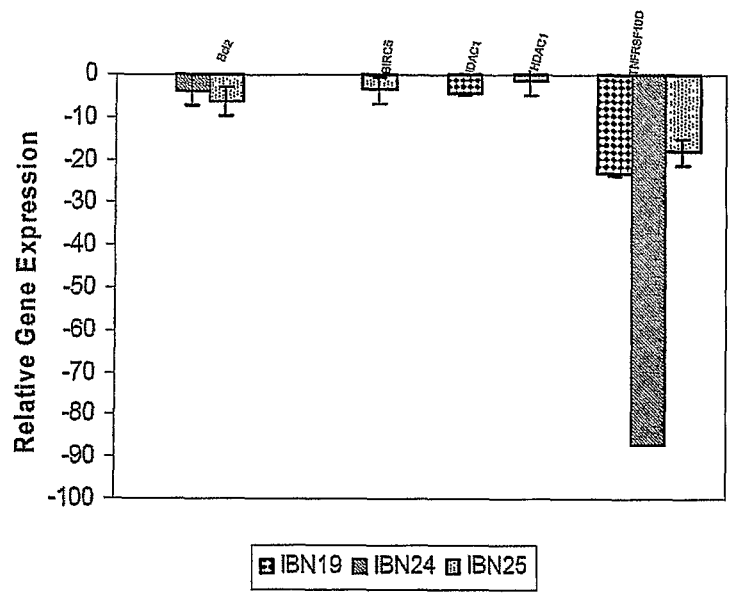
B
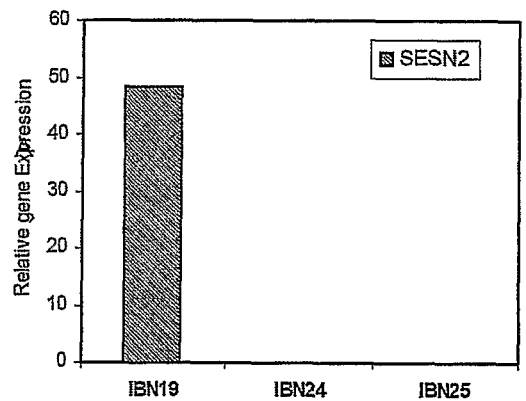
FIGURE 42

C
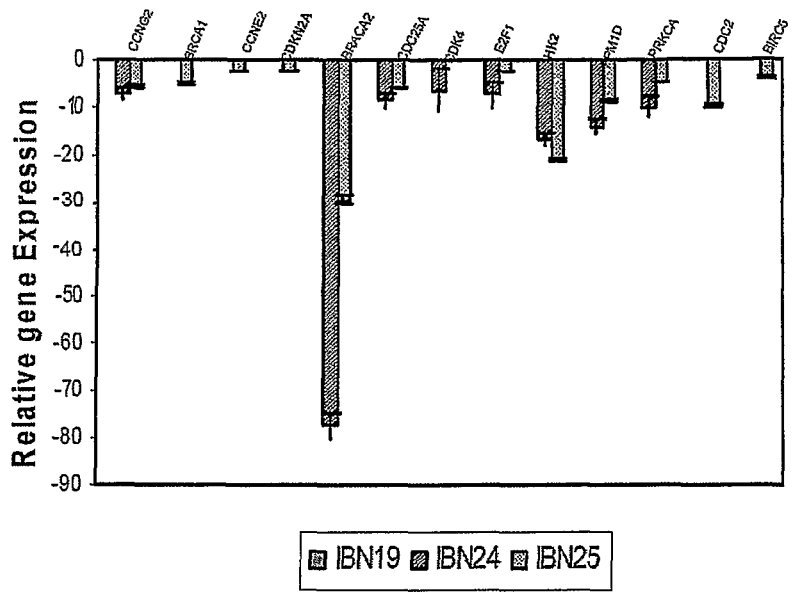
D
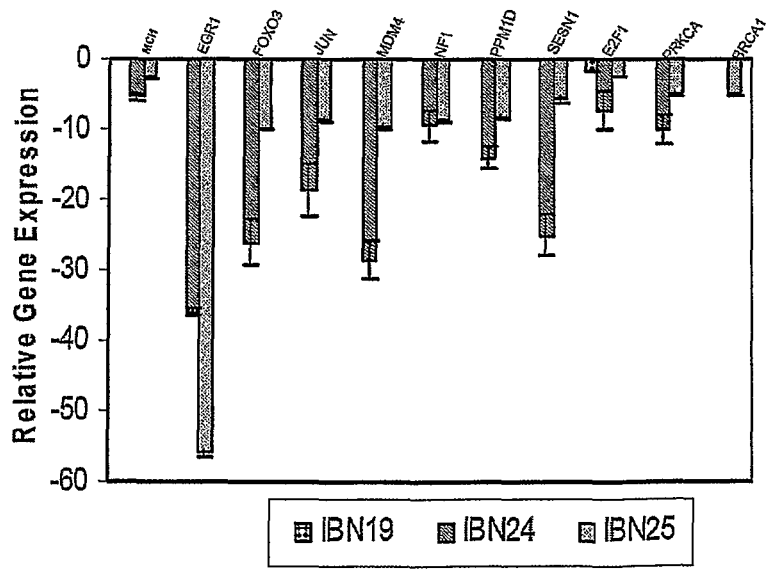
FIGURE 42 Continued

Table 1. Names and Structures of Particular IMSs

| Compound number | Chemical Name | Structure |
|---|---|---|
| DBZIM | 1,3-Dibenzylimidazolium bromide | 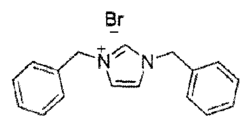 |
| DBZBIM | 1,3-Dibenzylbenzimidazolium bromide | 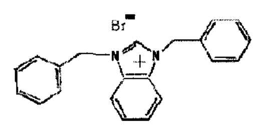 |
| TDBZIM | 1,3,5-tris(4-methyl-imidazolium)-linked cyclophane·3Br | 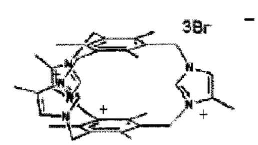 |
| DBZMIM | 1,3-Dibenzyl-2-methylimidazolium bromide | 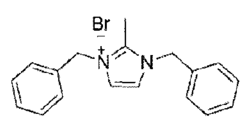 |
| DBIM | 1,3-Di-tert-butylimidazolinium tetrafluoroborate | 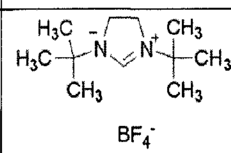 |
| AMIM | $N,N'$-(Adamantyl)imidazolium tetrafluoroborate | 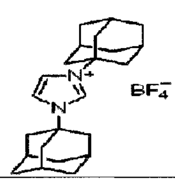 |
| DPPHIM | 1,3-Bis-(2,6-diisopropylphenyl)imidazolinium chloride | 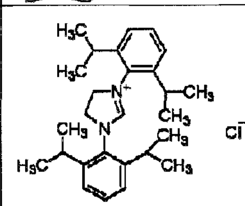 |

FIGURE 45

Table 1 Continued

| | | |
|---|---|---|
| DPIM | 1,3-Diisopropylimidazolium tetrafluoroborate | |
| Compound D (IBN-13) | 1,3-Diallylimidazolium bromide | |
| Compound E (IBN-12) | 1-benzyl-3-methylimidazolium bromide | |
| Compound G | 1-Butyl-3-methylimidazolium chloride | |
| Compound H | 1,3-Dibenzyl-2-(1,3-dibenzyl-1H-imidazol-2(3H)-ylidene)-2,3-dihydro-1H-imidazole | |
| Compound 2 (IBN-2) | 1-methyl-3-(2-hydroxylethyl)-imidazolium bromide | |
| Compound 3 (IBN-3) | 1-methyl-3-(4-isocynatobenzyl)-imidazolium chloride | |
| Compound 4 (IBN-4) | 1-methyl-3-(4-carboxylbenzyl)-imidazolium bromide | |
| Compound 6 (IBN-6) | 1-methyl-3-(4-acetate-benzyl)-imidazolium chloride | |

FIGURE 45 CONTINUED

Table 1 Continued

| | | |
|---|---|---|
| Compound 8 (IBN-8) | 1-methyl-3-(2,2-dimethoxylethyl)-imidazolium bromide | |
| Compound 9 (IBN-9) | 1-(2,4,6-trimethylphenyl)-3-(4-acetate-benzyl)-imidazolium chloride | |
| IBN-11 | 1-ethyl-3-methylimidazolium bromide | |
| IBN-12 | 1-methyl-3-benzylimidazolium bromide | |
| IBN-13 | 1,3-bisallylimidazolium bromide | |
| IBN-15 | 1,3-Dibenzyl-5-phenylimidazolium bromide | |
| IBN-17 | 1-benzyl-3-(4-carboxylbenzyl)-2-methylimidazolium chloride | |
| IBN-18 | 1-benzyl-3-(3,4,5-trimethoxylbenzyl)-2-methylimidazolium chloride | |
| IBN-19 | 1-benzyl-3-(4-acetate-benzyl)-2-methyl-imidazolium chloride | |

FIGURE 45 CONTINUED

Table 1 Continued

| IBN-20 | 1-benzyl-3-(4-methylcarboxylatebenzyl)-2-methyl-imidazolium chloride | |
| --- | --- | --- |
| IBN-21 | 1-benzyl-3-(2,2-dimethoxylethyl)-2-methyl-imidazolium bromide | |
| IBN-22 | 2,6-di-(3-benzyl-imidazolium bromide)-pyridine | |
| IBN-23 | 2,2'-di-(3-benzyl-imidazolium bromide)-1,1'-binaphthalene | |
| IBN-24 | 1-benzyl-3-(4-methylbenzyl)-imidazolium chloride | |
| IBN-25 | 1-benzyl-3-(2-trifluoromethylbenzyl)-2-methylimidazolium chloride | |
| IBN-26 | 1-benzyl-3-(4-methylcarboxylatebenzyl)-5-phenyl-imidazolium bromide | |
| IBN-27 | 1-benzyl-3-(4-acetatebenzyl)-5-phenyl-imidazolium bromide | |

FIGURE 45 CONTINUED

Table 1 Continued

| IBN-28 | 1-benzyl-3-(4-methylbenzyl)-5-phenylimidazolium chloride | |
| --- | --- | --- |
| IBN-29 | Benzo(1,2-4,5-diimidazolium)-N,N',N'',N'''-tetrabenzyl-,di-bromide | |
| IBN-30 | 1-benzyl-3-(2-propyn-1-yl)-imidazolium bromide | |
| IBN-31 | 1-benzyl-3-(3-hydroxyl-propyl)-imidazolium bromide | |
| IBN-32 | 1,3-di(2-phenylethyl)-imidazolium bromide | |
| IBN-33 | 1-benzyl-3-(4-acetatebenzyl)-imidazolium chloride | |
| IBN-34 | 1-benzyl-3-(pyridin-2-yl)-imidazolium bromide | |
| S1 | 1-(1-Adamantyl)-3-(2,4,6-trimethylphenyl)-4,5-dihydroimidazolium chloride | |

FIGURE 45 CONTINUED

Table 1 Continued

| S2 | 2-Benzylimidazo[1,5-*a*]quinolinium chloride | |
| --- | --- | --- |
| S3 | 1,3-Bis(1-adamanthyl)benzimidazolium chloride | |
| S4 | 1,3-Bis(2,6-diisopropylphenyl)imidazolium chloride | |
| S5 | 1,3-Di-*tert*-butylimidazolium tetrafluoroborate | |
| S6 | 1,3-Dicyclohexylbenzimidazolium chloride | |
| S7 | 1,3-Diisopropylimidazolinium tetrafluoroborate | |

FIGURE 45 CONTINUED

Table 1 Continued

| S8 | 1,3-Diisopropylimidazolium chloride | |
|---|---|---|
| S9 | 2-(2,6-Diisopropylphenyl)-5-methylimidazo[1,5-a]pyridinium hexafluorophosphate | |
| S10 | 1-(2,6-Diisopropylphenyl)-3-(2,4,6-trimethylphenyl)-imidazolinium chloride | |
| S11 | 2-Mesityl-5-methylimidazo[1,5-a]pyridinium chloride | |
| S12 | 2-Mesityl-2,5,6,7-tetrahydropyrrolo[2,1-c][1,2,4]triazol-4-ium chloride | |
| S13 | 1,3-Bis(1-adamantyl)imidazolinium tetrafluoroborate | |

FIGURE 45 CONTINUED

Table 1 Continued

| S14 | 1-Butyl-3-(2-pyridinylmethyl)-1H-imidazolium hexafluorophosphate | |
| --- | --- | --- |
| S15 | 6,7-Dihydro-2-pentafluorophenyl-5H-pyrrolo[2,1-c]-1,2,4-triazolium tetrafluoroborate | |
| TMPHIM | 1,3-Bis (2,4,6,-trimethylphenyl)-imidazolinium chloride | |

FIGURE 45 CONTINUED

Table 2. IC50 values of IMSs.

| Generic Name | Chemical Name | Structure | Molecular Weight | IC50 | Source |
|---|---|---|---|---|---|
| DPIM | 1,3-Diisopropylimida-zolium tetrafluoroborate | 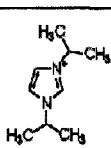 | 240.05 | 1.7 mM | Sigma |
| AMIM | 1,3-Bis(1-adamantyl)imida-zolium tetrafluoroborate | 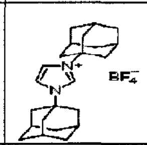 | 424.33 | 166 µM | Sigma |
| TMPHIM | 1,3-Bis(2,4,6-trimethylphenyl)imidaz olinium chloride | 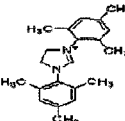 | 342.91 | 110 µM | Sigma |
| DPPHIM | 1,3-Bis-(2,6-diisopropylphenyl)imid azolinium chloride | 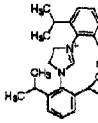 | 427.06 | 34 µM | Sigma |
| TDBZIM | 1,3,5-tris(4-methyl-imidazolium)-linked cyclophane·3Br | 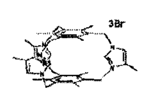 | 804.52 | 50-500 µM | IBN |
| DBIM | 1,3-Di-*tert*-butylimidazolium tetrafluoroborate | 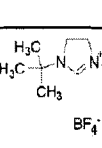 | 265.8 | 2 - 3mM | IBN |
| DBZMIN (C) | 1,3-Dibenzyl-2-methylimidazolium bromide | 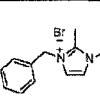 | 343.26 | 2 - 3mM | IBN |

FIGURE 46

Table 2. Continued

| | | | | | |
|---|---|---|---|---|---|
| IBN - 1 (DBZIM) or A | 1,3-Dibenzylimidazolium bromide | | 329.23 | 2 - 4mM | IBN |
| IBN - 2 (DBZBIM) or B | 1,3-Bisbenzyl-benzimida-zolium bromide | | 378.29 | 310 µM | IBN |
| IBN-3 | 1-methyl-3-(4-isocynatobenzyl)-imidazolium chloride | | 237.60 | 0.4mM | IBN |
| IBN-4 | 1-methyl-3-(4-carboxylbenzyl)-imidazolium bromide | | 285.05 | >10mM | IBN |
| IBN-6 | 1-methyl-3-(4-acetate-benzyl)-imidazolium chloride | | 239.59 | >10mM | IBN |
| IBN-8 | 1-methyl-3-(2,2-dimethoxyethyl)-imidazolium bromide | | 236.00 | >10mM | IBN |
| IBN-9 | 1-(2,4,6-trimethylphenyl)-3-(4-acetate-benzyl)-imidazolium chloride | | 335.68 | 0.2mM | IBN |
| IBN - 10 (H) | 1,3-Dibenzyl-2-(1,3-dibenzyl-1H-imidazol-2(3H)-ylidene)-2,3-dihydro-1H-imidazole | | 460.39 | 0.2 mM | IBN |

FIGURE 46 CONTINUED

Table 2. Continued

| | | | | | |
|---|---|---|---|---|---|
| IBN-11 | 1-ethyl-3-methylimidazolium bromide | 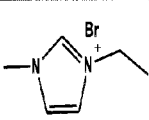 | 174.67 | >10mM | IBN |
| IBN-12 | 1-methyl-3-benzylimidazolium bromide | 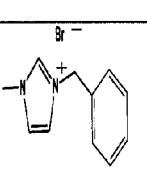 | 231.048 | 8mM | IBN |
| IBN-13 | 1,3-bisallylimidazolium bromide | 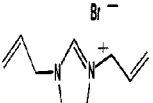 | 204.003 | ~8mM | IBN |
| IBN-15 | 1,3-Dibenzyl-5-phenylimidazolium bromide | 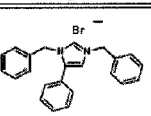 | 405.33 | ~8mM | IBN |
| IBN-17 | 1-benzyl-3-(4-carboxylbenzyl)-2-methylimidazolium chloride | 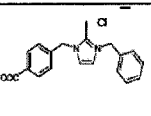 | 387.27 | ~9mM | IBN |
| IBN-18 | 1-benzyl-3-(3,4,5-trimethoxylbenzyl)-2-methyl imidazolium chloride | 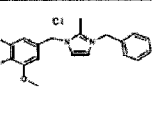 | 388.89 | ~6mM | IBN |
| IBN-19 | 1-benzyl-3-(4-acetate-benzyl)-2-methyl-imidazolium chloride | 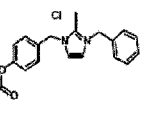 | 356.85 | ~80 μM | IBN |

FIGURE 46 CONTINUED

Table 2. Continued

| | | | | | |
|---|---|---|---|---|---|
| IBN-21 | 1-benzyl-3-(2,2-dimethoxylethyl)-2-methyl-imidazolium bromide | 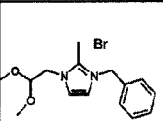 | 341.24 | ~1.4mM | IBN |
| IBN-22 | 2,6-di-(3-benzyl-imidazolium bromide)-pyridine | 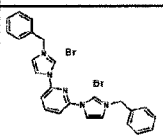 | 533.29 | ~ 0.76mM | IBN |
| IBN-23 | 2,2'-di-(3-benzyl-imidazolium bromide)-1,1'-binaphthalene | 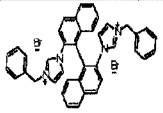 | 728.52 | ~ 1.5mM | IBN |
| IBN 24 | 1-benzyl-3-(4-methylbenzyl)-imidazolium chloride | 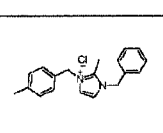 | 312.84 | 0.2mM | IBN |
| IBN-25 | 1-benzyl-3-(2-trifluoromethyl benzyl)-2-methylimidazolium chloride | 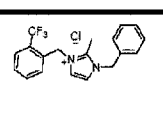 | 366.81 | 0.2mM | IBN |
| IBN-32 | 1,3-di(2-phenylethyl)-imidazolium bromide | 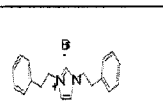 | 357.29 | 1.5mM | IBN |
| E | 1-Benzyl-3-methylimidazolium bromide | 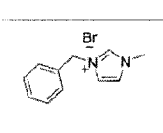 | 253.14 | ~ 8mM | IBN |
| F | 1,3-Di-tert-butylimidazolium tetrafluoroborate | 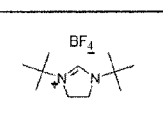 | 270.12 | 2 – 3mM | IBN |
| G | 1-Butyl-3-methylimidazolium chloride | 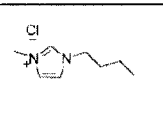 | 174.67 | 3-4mM | IBN |

FIGURE 46 CONTINUED

Table 2. Continued

| | | | | | |
|---|---|---|---|---|---|
| S1 | 1-(1-Adamantyl)-3-(2,4,6-trimethylphenyl)-4,5-dihydroimidazolium chloride | | 358.95 | ~ 50 µM | Sigma |
| S2 | 2-Benzylimidazo[1,5-a]quinolinium chloride | | 294.78 | ~ 0.3 mM | Sigma |
| S3 | 1,3-Bis(1-adamanthyl)benzimidazolium chloride | | 423.03 | ~ 1 µM | Sigma |
| S4 | 1,3-Bis(2,6-diisopropylphenyl)imidazolium chloride | | 425.05 | ~ 20 µM | Sigma |
| S5 | 1,3-Di-*tert*-butylimidazolium tetrafluoroborate | | 268.10 | ~ 4.6 mM | Sigma |
| S6 | 1,3-Dicyclohexylbenzimidazolium chloride | | 318.88 | ~ 80 µM | Sigma |
| S7 | 1,3-Diisopropylimidazolinium tetrafluoroborate | | 242.07 | >10 mM | Sigma |
| S8 | 1,3-Diisopropylimidazolium chloride | | 188.70 | >10 mM | Sigma |

FIGURE 46 CONTINUED

Table 2. Continued

| | | | | | |
|---|---|---|---|---|---|
| S9 | 2-(2,6-Diisopropylphenyl)-5-methylimidazo[1,5-a]pyridinium hexafluorophosphate | | 438.39 | ~ 0.13 mM | Sigma |
| S10 | 1-(2,6-Diisopropylphenyl)-3-(2,4,6-trimethylphenyl)-imidazolinium chloride | | 384.99 | ~30 µM | Sigma |
| S11 | 2-Mesityl-5-methylimidazo[1,5-a]pyridinium chloride | | 286.80 | ~ 0.2mM | Sigma |
| S12 | 2-Mesityl-2,5,6,7-tetrahydropyrrolo[2,1-c][1,2,4]triazol-4-ium chloride | | 263.77 | ~ 4.8mM | Sigma |
| S13 | 1,3-Bis(1-adamantyl)imidazolinium tetrafluoroborate | | 426.34 | ~ 40 µM | Sigma |
| S14 | 1-Butyl-3-(2-pyridinylmethyl)-1H-imidazolium hexafluorophosphate | | 361.27 | >10mM | Sigma |
| S15 | 6,7-Dihydro-2-pentafluorophenyl-5H-pyrrolo[2,1-c]-1,2,4-triazolium tetrafluoroborate | | 362.99 | >10mM | Sigma |

FIGURE 46 CONTINUED

Table 3. IC50 values of DBZIM in various cancer cell lines.

IC50 determined at day 3

| IBN # | Name of the Cell line | Chemical Name | Chemical Structure | IC-50 (Day 3) |
|---|---|---|---|---|
| 1 | Lung Cancer Cell line H1299 | 1, 3- Dibenzylimidazolium bromide, ( DBZIM) Mw = 329.23 | | 50 µM |
| 1 | Breast Cancer Cell line MCF-7 | 1, 3- Dibenzylimidazolium bromide, ( DBZIM) Mw = 329.23 | | 50 µM |
| 1 | Gastric Cancer Cell line AGS | 1, 3- Dibenzylimidazolium bromide, ( DBZIM) Mw = 329.23 | | 40 µM |
| 1 | Normal Lung cells IMR90 | 1, 3- Dibenzylimidazolium bromide, ( DBZIM) Mw = 329.23 | | NIL |

FIGURE 47

Table 4. IC50 values of IBN-15, 19, 24, 25 and 32 in HLE cells.

| IBN # | Molecular weight | Chemical Structure | Day 3 IC-50 | Day 5 IC-50 |
|---|---|---|---|---|
| IBN-15 | 405.33 | 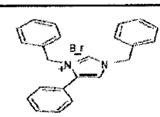 | 60 µm | 20 µm |
| IBN-19 | 356.85 | 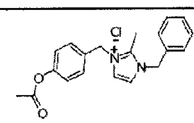 | 90 µm | 28 µm |
| IBN-24 | 312.84 | 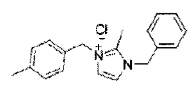 | 90 µm | 30 µm |
| IBN-25 | 366.81 | 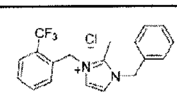 | 30 µm | 35 µm |
| IBN-32 | 357.29 | 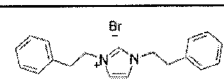 | 20 µm | 20 µm |

FIGURE 48

Table 5. IC50 values of DBZMIM in gastric cancer cells.

| IBN # or Name | Cell line | Chemical name | Chemical structure | IC-50 (Day 5) |
|---|---|---|---|---|
| Compound C or DBZMIN | Gastric cancer cell line MKN 28 (p53 Mutant) | 1,3-Dibenzyl-2-methylimidazolium bromide, MW: 343.26 | 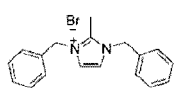 | 35 µM |
| Compound 9 or MABZIM | Gastric cancer cell line MKN 28 (p53 Mutant) | 1-Mesityl-3-(4-acetate-benzyl)-imidazolium chloride MW: 370.87 | 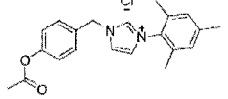 | 10 µM |
| | Gastric cancer cell line MKN 28 (p53 Mutant) | 5-Fluorouracil | 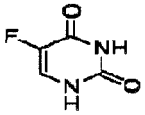 | 20 µM |

FIGURE 49

Table 6. IC50 values of DBZMIM in breast cancer cells

| IBN # or name | Name of the Cell line | Chemical Nme | Chemical Structure | IC-50 (Day 3) |
|---|---|---|---|---|
| Compound C or DBZMIM | Breast cancer cell line MDAMB231 (p53 Mutant) | 1,3-Dibenzyl-2-methylimidazolium bromide MW: 343.26 | 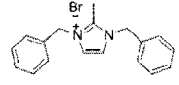 | 35 µM |
| Compound 9 or MABZIM | Breast cancer cell line MDAMB231 (p53 Mutant) | 1-Mesityl-3-(4-acetate-benzyl)-imidazolium chloride MW: 370.87 | 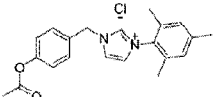 | 20 µM |
| | Breast cancer cell line MDAMB231 (p53 Mutant) | 5-Flurouracil | 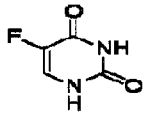 | 15 µM |

FIGURE 50

Table 7. IC50 values of DBZMIM and Compound 9 in normal breast cells.
| IBN # or name | Name of the Cell line | Chemical Name | Chemical Structure | IC-50 (Day 5) |
|---|---|---|---|---|
| Compound C, or DBZMIM | Normal Breast cells (MCF-10A) | 1,3-Dibenzyl-2-methylimidazolium bromide<br>MW: 343.26 | 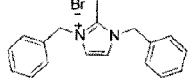 | N/A |
| Compound 9 or MABZIM | Normal Breast cells (MCF-10A) | 1-Mesityl-3-(4-acetate-benzyl)-imidazolium chloride<br>MW: 370.87 | 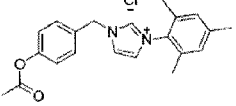 | N/A |
FIGURE 51

METHOD FOR TREATING FIBROSIS AND CANCER WITH IMIDAZOLIUM AND IMIDAZOLINIUM COMPOUNDS

CROSS-REFERENCE TO RELATED APPLICATION

This application claims benefit of, and priority from, U.S. provisional patent application No. 61/006,769 filed on Jan. 30, 2008, the contents of which are fully incorporated herein by reference.

FIELD OF THE INVENTION

The present invention relates to methods for delivering an anti-fibrotic or an anti-cancer agent to a cell, including methods for treating fibrotic disease or cancer.

BACKGROUND OF THE INVENTION

Hepatic stellate cells (HSCs) play a pivotal role in hepatic fibrogenesis and are considered a major cellular target for therapeutic intervention. However, no approved anti-fibrotic drug is currently on the market.

Hepatic fibrogenesis may be incurred as a result of insults arising from oxidative stress, chemical toxicity or viral infection. Thus fibrotic disease, including cell and tissue fibrosis, is among the physiological disorders that have been associated with oxidative stress. For example, oxidative stress resulting from the metabolic generation of ROS has been linked to HSC activation and liver fibrosis (Britton et al. 1994, Tsukamoto et al. 1995, GAB et al. 2005). It has been shown that products of lipid peroxidation lead to increased collagen synthesis by HSCs (Casini et al. 1997 and Parola et al. 1996).

Reactive oxygen species (ROS) are oxygen derivatives that include free radicals and non-radical reactive molecules such as peroxides and oxygen derivatives. Oxidative stress occurs when there is an excess amount of ROS due to an imbalance between the generation and the elimination or neutralization of these molecules. Excess amounts of ROS may damage cell lipids, proteins and DNA resulting in the inhibition of normal cell function or the development of abnormal cellular behaviour which can in turn lead to a variety of diseases and conditions, depending on the cells affected. ROS have been implicated in many physiological disorders and in the onset and development of a number of diseases.

Some anti-oxidants have been explored as potential inhibitors of hepatic fibrosis (Kawada et al. 1998). (−)-Epigallocatechin gallate (EGCG), a major active component of tea catechin, has been shown to inhibit HSC activation in vitro via transforming growth factor-beta (TGF-β) signalling (Chen et al. 2002, Nakanuta et al. 2005, Fu et al. 2006). In clinical studies, a combination of vitamins E and C was shown to decrease the fibrosis score in non-alcoholic steatohepatitis patients, but did not affect hepatic inflammation (Harrison et al. 2003). N-acetyl-L-cysteine (NAC), a synthetic precursor of glutathione (GSH) that has been clinically used as an antioxidant, showed anti-fibrogenic properties through the suppression of TGF-β signalling transduction as well (Meurer et al. 2005).

Oxidative stress has also been associated with the onset and progression of cancer. It has been reported that oxidative stress as indicated by reduced anti-oxidant enzyme activities is associated with the development of primary carcinogenesis and metastasis in clinical patients (Vali et al. 2008). ROS have been found to cause DNA damage increasing the risk of DNA mutation and thus the development of cancer (Hussain et al. 2005). Tea polyphenols are anti-oxidants and have been shown to inhibit carcinogen-induced DNA damage in animal models of skin, lung, colon, liver and pancreatic cancers (Frei et al. 2003). In addition, anti-oxidants PBN and NXY-059 have demonstrated anti-cancer activity in hepatocellular carcinoma. (Floyd 2006). However, the effectiveness of the anti-oxidants investigated remains unclear (Valko et al, 2004).

The inflammatory response is the immune system's response to infection or injury and involves the activation of cells of the immune system which produce mediators, such as cytokines, that further activate other cells, leading to a cascade of immune reactions that fight off the infection or repair the injury. Like oxidative stress, inflammatory stresses have been associated with fibrotic disease and cancer (Rakoff-Nahoum 2006; Tsukamoto et al. 1999; Bachem et al. 1992; Vasiliou et al. 2000). For example, in the development of liver fibrosis, HSCs play a critical role. Responding to liver injury, HSCs undergo a process called "activation" and trans-differentiate to myofibroblast-like cells. This process is characterized by phenotypic changes including cell proliferation, over-expression of smooth muscle actin-α (SMAA), and deposition of extracellular matrix (ECM) proteins, including collagen type αI (I) (col1a1) and fibronectin.

Inflammatory cytokines represent major mediators for HSC activation. Among them, transforming growth factor-beta I (TGF-β1) and interleukin 6 (IL-6) have been categorized as profibrogenic cytokines mainly responsible for the induction of ECM proteins (Tsukamoto 1999). HSCs respond to TGF-β1 secreted from Kupffer cells and endothelial cells during liver injury, and themselves via autocrine action, resulting in HSC activation and liver fibrosis (Bachem et al. 1992). In addition, the activation of HSCs can also be attributed to chronic hepatic inflammation through the secretion of proinflammatory cytokine IL-6, leading to cirrhosis (Vasiliou et al. 2000) and hepatocellular carcinoma (Naugler et al, 2007). Transcription factor nuclear factor kappa B (NF-κB) is an important regulator for the secretion of inflammatory cytokines, and its subunit NF-κB p65 was reported to mediate liver fibrosis (Vasiliou et al. 2000).

Beyond sharing a common association with fibrotic diseases and cancer, the production and regulation of oxidative and inflammatory stress appear to be interconnected, as an inflammatory response can trigger oxidative stress and vice versa.

For example, in hepatic fibrogenesis, both ROS and pro-inflammatory cytokines have been shown to be involved in the activation of HSCs, the central event in the development of liver fibrogenesis. TGF-β is a major mediator for HSC activation and TGF-β signalling is affected by both oxidative stress and the induction of an inflammatory response (Tsukamoto et al. 1999, Bachem et al. 1992, Chen et al. 2002, Nakanuta et al. 2005, Fu et al. 2006, Meurer et al. 2005). Another key molecule in the development of fibrosis, is NF-κB which is an important regulator of the secretion of inflammatory cytokines but is also known to be sensitive to oxidative stress. Most agents activating NF-κB are either modulated by ROS or oxidant themselves. It has been reported that treatment with anti-oxidant resveratrol (Chavez et al. 2007) or vitamin E (Liu et al. 1995) attenuated NF-κB elevation induced in carbon tetrachloride experimental fibrotic rodents.

Oxidative stress and inflammatory response have also been found to be interrelated in the pathogenesis of cancer. Oxidative stress can cause DNA mutations, some of which will result in the formation of cancer cells. However other mutations will result in cell death, stimulating an inflammatory response. In turn, an inflammatory response will not only provide survival and proliferative signals to cancer cells but may also induce the production of ROS (Rakoff-Nahoum 2006).

Dietary anti-oxidants have been widely used as a general approach to ameliorate excessive oxidative stress both in animal models and humans. For example, resveratrol has been shown to extend the lifespan of various species, and to be effective at improving the health and survival of mice on a high-calorie diet (Baur et al. 2006).

To date, the development of effective treatments for oxidative stress and certain diseases associated with oxidative stress using natural or synthetic anti-oxidants has been problematic. Stringent scientific proof for the efficacy of natural anti-oxidants has not been established (Droge et al. 2001). Some of the notable limitations for using natural anti-oxidants as therapeutics include low potency and fast turnover during metabolism. In contrast, the development of synthetic anti-oxidants has been inhibited by safety concerns. Nevertheless, some progress has been made in this direction. Modification of a natural anti-oxidant has been performed to enhance its potency (Keum et al. 2007). In addition, synthetic mimics of superoxide dismutase (SOD) and catalase have been shown to be effective in rodent models of ischemia and Parkinson's disease (Peng et al. 2005). Even more encouragingly, a class of nitron-free radical trap agents, alpha-phenyl-N-tert-butyl-nitron (PBN) and disodium 2,4-disulfophenyl-N-tert-butylnitrone (NXY-059), have been shown to be Potent neuroprotective agent (Maples et al. 2004), and have demonstrated anti-cancer activity in hepatocellular carcinoma through its anti-inflammatory property (Floyd 2006).

SUMMARY OF THE INVENTION

There is presently provided methods for delivering an anti-fibrotic or anti-cancer agent to a cell, the method comprising contacting a cell with an effective amount of imidazolium and imidazolinium compounds, including imidazolium and imidazolinium salts, as described herein.

In one aspect, there is provided a method for delivering an anti-fibrotic or anti-cancer agent to a cell, the method comprising contacting the cell with an effective amount of a compound of general formula I or an oligomer or polymer thereof:

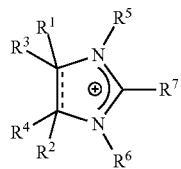

(I)

wherein:
the dashed line is absent or is present as a bond to form a second bond between the carbon to which $R^1$ and $R^3$ are attached and the carbon to which $R^2$ and $R^4$ are attached;
$R^1$ and $R^2$:
  (i) are each independently H, straight or branched $C_1$-$C_6$ alkyl, straight or branched $C_2$-$C_6$ alkenyl, straight or branched $C_2$-$C_6$ alkynyl, $C_6$-$C_{10}$ aryl;
  (ii) together with their ring atoms form a 6- to 10-membered fused saturated, unsaturated or aromatic ring system;
  (iii) $R^1$ and $R^5$ together with their ring atoms, or $R^2$ and $R^6$ together with their ring atoms, form a 5- to 10-membered fused saturated, unsaturated or aromatic ring system and the other of $R^1$ and $R^2$ is as defined above in (i); or
  (iv) $R^1$ and $R^5$ together with their ring atoms and $R^2$ and $R^6$ together with their ring atoms each form a 5- to 10-membered fused saturated, unsaturated or aromatic ring system;
$R^3$ and $R^4$ are both H, or, when $R^1$ and $R^2$ together with their ring atoms form a 6- to 10-membered fused aromatic ring system or when the dashed line is present as a bond, $R^3$ and $R^4$ are absent;
$R^5$ or $R^6$:
  (i) are as defined above for $R^1$ and $R^2$; or
  (ii) are each independently straight or branched $C_1$-$C_6$ alkyl, straight or branched $C_2$-$C_6$ alkenyl, straight or branched $C_2$-$C_6$ alkynyl, $C_3$-$C_{18}$ cycloalkyl including fused cycloalkyl ring systems, $C_6$-$C_{10}$ aryl, $C_6$-$C_{10}$ aryl-$C_1$-$C_6$ alkyl, $C_6$-$C_{10}$ aryl-$C_2$-$C_6$ alkenyl, or $C_6$-$C_{10}$ aryl-$C_2$-$C_6$ alkynyl, $C_1$-$C_6$ alkyl-$C_6$-$C_{10}$ aryl, $C_2$-$C_6$ alkenyl-$C_6$-$C_{10}$ aryl, or $C_2$-$C_6$ alkynyl-$C_6$-$C_{10}$ aryl;
$R^7$ is H, $C_1$-$C_6$ alkyl, phenyl, substituted $C_1$-$C_6$ alkyl or halo;
in which any of $R^1$ to $R^7$, where applicable, optionally has one or more carbon atoms replaced with a heteroatom selected from N, O, S and P and is optionally substituted with one or more of straight or branched $C_1$-$C_6$ alkyl, straight or branched $C_2$-$C_6$ alkenyl, straight or branched $C_2$-$C_6$ alkynyl, $C_3$-$C_{18}$ cycloalkyl including fused cycloalkyl ring systems, $C_6$-$C_{10}$ aryl, fluoro, tri-fluoro-methyl, cyanato, isocyanato, carboxyl, $C_1$-$C_6$ acyloxy, $C_1$-$C_6$ acyl, carbonyl, amino, acetyl, acetoxy, oxo, nitro, hydroxyl, $C_1$-$C_6$ alkylcarboxy, $C_1$-$C_6$ alkoxy, $C_2$-$C_6$ alkenoxy, $C_2$-$C_6$ alkynoxy; and
and in which one of the ring carbon atom to which $R^1$ and $R^5$ are attached and the ring carbon to $R^2$ and $R^6$ are attached is optionally replaced with a nitrogen atom;
or a pharmaceutically acceptable salt thereof.

In one embodiment, the compound is an imidazolium or an imidazolium. In another embodiment, the compound is an imidazolinium or an imidazolinium salt.

In one embodiment, $R^5$ is the same as $R^6$. In another embodiment $R^5$ and $R^6$ are hydrocarbons.

In certain embodiments, the pharmaceutically acceptable salt of general formula I may be a chloride, bromide, tetrafluoroborate or hexafluorophosphate salt.

In various embodiments, the compound may be 1-ethyl-3-methylimidazolium, 1,3-bisbenzylimidazolium, 1,3-diisopropylimidazolium, 1,3-di-tert-butylimidazolinium, 1,3-bis(1-adamantyl)imidazolium, 1,3-bis(2,4,6-trimethylphenyl)-imidazolinium, 1,3-bis(2,6-diisopropylphenyl)-imidazolinium, 1,3-diallylimidazolium, 1-benzyl-3-methylimidazolium, 1-butyl-3-methylimidazolium, 1-(1-adamantyl)-3-(2,4,6-trimethylphenyl)-4,5-dihydroimidazolium, 2-benzylimidazo[1,5-a]quinolinium, 1,3-bis(1-adamantyl)-benzimidazolium, 1,3-dicyclohexyl-benzimidazolium, 1,3-diisopropylimidazolinium tetrafluoroborate, 1,3-diisopropylimidazolium, 2-(2,6-diisopropylphenyl)-5-methylimidazo[1,5-a]pyridinium, 1-(2,6-diisopropylphenyl)-3-(2,4,6-trimethylphenyl)-imidazolinium, 2-mesityl-5-methylimidazo[1,5-a]pyridinium, 2-mesityl-2,5,6,7-tetrahydropyrrolo[2,1-c][1,2,4]triazol-4-ium, 1,3-bis(1-adamantyl)imidazolinium, 1-butyl-3-(2-pyridinylmethyl)-1H-imidazolium, 6,7-dihydro-2-pentafluorophenyl-5H-pyrrolo[2,1-c]-1,2,4-trizolium, 1-methyl-3-(2-hydroxylethyl)-imidazolium, 1-methyl-3-(4-isocynatobenzyl)-imidazolium, 1-methyl-3-(4-carboxylbenzyl)-imidazolium, 1-methyl-3-(4-acetate-benzyl)-imidazolium, 1-methyl-3-(2,2-dimethoxylethyl)-imidazolium, 1-(2,4,6-trimethylphenyl)-3-(4-acetate-benzyl)-imidazolium, 1,3-Dibenzyl-5-phenylimidazolium, 1-benzyl-3-(4-carboxylbenzyl)-2-methylimidazolium, 1-benzyl-3-(3,4,5-trimethoxylbenzyl)-2-methylimidazolium, 1-benzyl-3-(4-acetate-benzyl)-2-methyl-imidazolium, 1-benzyl-3-(4-methylcarboxylatebenzyl)-2-methyl-imidazolium, 1-benzyl-3-(2,2-dimethoxylethyl)-2-methyl-imidazolium, 2,6-di-(3-benzyl-imidazolium)-pyridine, 2,2'-di-(3-benzyl-imidazolium)-1,1'-binaphthalene, 1-benzyl-3-(4-methylbenzyl)-imidazolium, 1-benzyl-3-(2-trifluoromethylbenzyl)-2-methylimidazolium, 1-benzyl-3-(4-methylcarboxylatebenzyl)-5-phenyl-imidazolium, 1-benzyl-3-(4-acetatebenzyl)-5-phenyl-imidazolium, 1-benzyl-3-(4-methylbenzyl)-5-phenylimidazolium, (1,2-4,5-diimidazolium)-N,N',N'',N'''-tetrabenzyl-benzene, 1-benzyl-3-(2-propyn-1-yl)-imidazolium, 1-benzyl-3-(3-hydroxylpropyl)-imidazolium, 1,3-di(2-phenylethyl)-imidazolium, 1-benzyl-3-(4-acetatebenzyl)-imidazolium, 1-benzyl-3-(pyridin-2-yl)-imidazolium, 1,3,5-tris-(4-methylimidazolium)-linked cyclophane, 1,3-dibenzyl-2-(1,3-dibenzyl-1H-imidazol-2(3H)-ylidene)-2,3-dihydro-1H-imidazole, 1-benzyl-3-methyl-imidazolium, 1-(4-cyanatobenzyl)-3-methylimidazolium, 1-(4-carboxybenzyl)-3-methyl-imidazolium, 1-methyl-3-(4-acetate-benzyl)-imidazolium, 1-methyl-3-(2,2-dimethoxyethyl)-imidazolium, or 1-(2,4,6-trimethylphenyl)-3-(4-acetate-benzyl)-imidazolium, or a pharmaceutically acceptable salt thereof.

In one embodiment, the compound is a dimer of a compound having a structure of general formula I. For example, the compound may be 1,3-dibenzyl-2-(1,3-dibenzyl-1H-imidazol-2(3H)-ylidene)-2,3-dihydro-1H-imidazole, (1,2-4,5-diimidazolium)-N,N',N'',N'''-tetrabenzyl-benzene, 2,6-di-(3-benzyl-imidazolium)-pyridine or 2,2'-di-(3-benzyl-imidazolium)-1,1'-binaphthalene, or a pharmaceutically acceptable salt thereof.

In another embodiment, the compound is a trimer of a compound having a structure of general formula I. For example, the compound is 1,3,5-tris(4-methyl-imidazolium)-linked cyclophane or a pharmaceutically acceptable salt thereof.

In one embodiment of the present methods, the cell may be in vitro.

In another embodiment, the cell may be in vivo. For example, the method may comprise administering the agent to a subject for the treatment of fibrotic disease or the treatment of cancer. In one particular embodiment, the fibrotic disease may be hepatic fibrosis amd the compound may be for example, 3-diisopropylimidazolium or a pharmaceutically acceptable salt thereof. In other embodiments, the cancer may be hepatocellular carcinoma, lung cancer, breast cancer, stomach cancer or glioma or the compound may be for example, 3-Bisbenzylimidazolium, 3-dibenzyl-2-methylimidazolium, 1-(2,4,6-trimethylphenyl)-3-(4-acetate-benzyl)-imidazolium, 1-benzyl-3-(4-acetate-benzyl)-2-methyl-imidazolium, 1-benzyl-3-(4-methylbenzyl)-imidazolium, 1-benzyl-3-(2-trifluoromethylbenzyl)-2-methylimidazolium or 1,3-di(2-phenylethyl)-imidazolium, or a pharmaceutically acceptable salt thereof.

In another aspect, there is provided use of a compound having a structure of general formula I, or an oligomer or polymer thereof, for delivering an anti-fibrotic or anti-cancer agent to a cell in vivo:

In another aspect, there is provided use of a compound having a structure of general formula I, or an oligomer or polymer thereof, in the manufacture of a medicament for delivering an anti-fibrotic or anti-cancer agent to a cell in vivo.

In one embodiment of the uses described herein, the compound is an imidazolium or an imidazolium salt. In another embodiment, the compound is an imidazolinium or an imidazolinium salt.

In other embodiments, $R^5$ is the same as $R^6$. In another embodiment $R^5$ and $R^6$ are hydrocarbon.

In certain embodiments, the pharmaceutically acceptable salt of general formula I may be a chloride, bromide, tetrafluoroborate or hexafluorophosphate salt.

In various embodiments of the present uses, the compound may be 1-ethyl-3-methylimidazolium, 1,3-bisbenzylimidazolium, 1,3-diisopropylimidazolium, 1,3-di-tert-butylimidazolinium, 1,3-bis(1-adamantyl)imidazolium, 1,3-bis(2,4,6-trimethylphenyl)-imidazolinium, 1,3-bis(2,6-diisopropylphenyl)-imidazolinium, 1,3-diallylimidazolium, 1-benzyl-3-methylimidazolium, 1-butyl-3-methylimidazolium, 1-(1-adamantyl)-3-(2,4,6-trimethylphenyl)-4,5-dihydroimidazolium, 2-benzylimidazo[1,5-a]quinolinium, 1,3-bis(1-adamantyl)-benzimidazolium, 1,3-dicyclohexyl-benzimidazolium, 1,3-diisopropylimidazolinium tetrafluoroborate, 1,3-diisopropylimidazolium, 2-(2,6-diisopropylphenyl)-5-methylimidazo[1,5-a]pyridinium, diisopropylphenyl)-3-(2,4,6-trimethylphenyl)-imidazolinium, 2-mesityl-5-methylimidazo[1,5-a]pyridinium, 2-mesityl-2,5,6,7-tetrahydropyrrolo[2,1-c][1,2,4]triazol-4-ium, 1,3-bis(1-adamantyl)imidazolinium, 1-butyl-3-(2-pyridinylmethyl)-1H-imidazolium, 6,7-dihydro-2-pentafluorophenyl-5H-pyrrolo[2,1-c]-1,2,4-trizolium, 1-methyl-3-(2-hydroxylethyl)-imidazolium, 1-methyl-3-(4-isocynatobenzyl)-imidazolium, 1-methyl-3-(4-carboxylbenzyl)-imidazolium, 1-methyl-3-(4-acetate-benzyl)-imidazolium, 1-methyl-3-(2,2-dimethoxylethyl)-imidazolium, 1-(2,4,6-trimethylphenyl)-3-(4-acetate-benzyl)-imidazolium, 1,3-Dibenzyl-5-phenylimidazolium, 1-benzyl-3-(4-carboxylbenzyl)-2-methylimidazolium, 1-benzyl-3-(3,4,5-trimethoxylbenzyl)-2-methylimidazolium, 1-benzyl-3-(4-acetate-benzyl)-2-methyl-imidazolium, 1-benzyl-3-(4-methylcarboxylatebenzyl)-2-methyl-imidazolium, 1-benzyl-3-(2,2-dimethoxylethyl)-2-methyl-imidazolium, 2,6-di-(3-benzyl-imidazolium)-pyridine, 2,2'-di-(3-benzyl-imidazolium)-1,1'-binaphthalene, 1-benzyl-3-(4-methylbenzyl)-imidazolium, 1-benzyl-3-(2-trifluoromethylbenzyl)-2-methylimidazolium, 1-benzyl-3-(4-methylcarboxylatebenzyl)-5-phenyl-imidazolium, 1-benzyl-3-(4-acetatebenzyl)-5-phenyl-imidazolium, 1-benzyl-3-(4-methylbenzyl)-5-phenylimidazolium, (1,2-4,5-diimidazolium)-N,N',N'',N'''-tetrabenzyl-benzene, 1-benzyl-3-(2-propyn-1-yl)-imidazolium, 1-benzyl-3-(3-hydroxylpropyl)-imidazolium, 1,3-di(2-phenylethyl)-imidazolium, 1-benzyl-3-(4-acetatebenzyl)-imidazolium, 1-benzyl-3-(pyridin-2-yl)-imidazolium, 1,3,5-tris-(4-methylimidazolium)-linked cyclophane, 1,3-dibenzyl-2-(1,3-dibenzyl-1H-imidazol-2(3H)-ylidene)-2,3-dihydro-1H-imidazole, 1-benzyl-3-methyl-imidazolium, 1-(4-cyanatobenzyl)-3-methylimidazolium, 1-(4-carboxybenzyl)-3-methyl-imidazolium, 1-methyl-3-(4-acetate-benzyl)-imidazolium, 1-methyl-3-(2,2-dimethoxyethyl)-imidazolium, or 1-(2,4,6-trimethylphenyl)-3-(4-acetate-benzyl)-imidazolium, or a pharmaceutically acceptable salt thereof.

In one embodiment, the compound is a dimer of a compound having a structure of general formula I. For example, the compound may be 1,3-dibenzyl-2-(1,3-dibenzyl-1H-imidazol-2(3H)-ylidene)-2,3-dihydro-1H-imidazole, (1,2-4,5-diimidazolium-N,N',N'',N'''-tetrabenzyl-benzene, 2,6-di-(3-benzyl-imidazolium)-pyridine or 2,2'-di-(3-benzyl-imidazolium)-1,1'-binaphthalene, or a pharmaceutically acceptable salt thereof.

In another embodiment, the compound is a trimer of a compound having a structure of general formula I. For example, the compound is 1,3,5-tris(4-methyl-imidazolium)-linked cyclophane or a pharmaceutically acceptable salt thereof.

In one embodiment of the present uses, the anti-fibrotic agent is delivered for the treatment of fibrotic disease. In a particular embodiment, the fibrotic disease may be hepatic fibrosis and the compound may be for example, 3-diisopropylimidazolium or a pharmaceutically acceptable salt thereof.

In another embodiment of the present uses, the anti-cancer agent is delivered for the treatment of cancer. In various embodiments the cancer s hepatocellular carcinoma, lung cancer, breast cancer, stomach cancer or glioma and the compounds may be, for example, 3-Bisbenzylimidazolium, 3-Dibenzyl-2-methylimidazolium, 1-(2,4,6-trimethylphenyl)-3-(4-acetate-benzyl)-imidazolium, 1-benzyl-3-(4-acetate-benzyl)-2-methyl-imidazolium, 1-benzyl-3-(4-methylbenzyl)-imidazolium, 1-benzyl-3-(2-trifluoromethylbenzyl)-2-methylimidazolium or 1,3-di(2-phenylethyl)-imidazolium, or a pharmaceutically acceptable salt thereof.

In another aspect there is provided, a compound that is an imidazolium or imidazolinium that is 1-ethyl-3-methylimidazolium, 1-methyl-3-(2-hydroxyethyl)-imidazolium, 1-methyl-3-(4-isocynatobenzyl)-imidazolium, 1-methyl-3-(4-carboxylbenzyl)-imidazolium, 1-methyl-3-(4-acetate-benzyl)-imidazolium, 1-methyl-3-(2,2-dimethoxylethyl)-imidazolium, 1-(2,4,6-trimethylphenyl)-3-(4-acetate-benzyl)-imidazolium, 1,3-Dibenzyl-5-phenylimidazolium, 1-benzyl-3-(4-carboxylbenzyl)-2-methylimidazolium, 1-benzyl-3-(3,4,5-trimethoxylbenzyl)-2-methylimidazolium, 1-benzyl-3-(4-acetate-benzyl)-2-methyl-imidazolium, 1-benzyl-3-(4-methylcarboxylatebenzyl)-2-methyl-imidazolium, 1-benzyl-3-(2,2-dimethoxylethyl)-2-methyl-imidazolium, 2,6-di-(3-benzyl-imidazolium)-pyridine, 2,2'-di-(3-benzyl-imidazolium)-1,1'-binaphthalene, 1-benzyl-3-(4-methylbenzyl)-imidazolium, 1-benzyl-3-(2-trifluoromethylbenzyl)-2-methylimidazolium, 1-benzyl-3-(4-methylcarboxylatebenzyl)-5-phenyl-imidazolium, 1-benzyl-3-(4-acetatebenzyl)-5-phenyl-imidazolium, 1-benzyl-3-(4-methylbenzyl)-5-phenylimidazolium, (1,2-4,5-diimidazolium)-N,N',N'',N'''-tetrabenzyl-benzene, 1-benzyl-3-(2-propyn-1-yl)-imidazolium, 1-benzyl-3-(3-hydroxylpropyl)-imidazolium, 1,3-di(2-phenylethyl)-imidazolium, 1-benzyl-3-(4-acetatebenzyl)-imidazolium, 1-benzyl-3-(pyridin-2-yl)-imidazolium, 1,3,5-tris-(4-methylimidazolium)-linked cyclophane, 1,3-dibenzyl-2-(1,3-dibenzyl-1H-imidazol-2(3H)-ylidene)-2,3-dihydro-1H-imidazole, 1-benzyl-3-methyl-imidazolium, 1-(4-cyanatobenzyl)-3-methyl-imidazolium, 1-(4-carboxybenzyl)-3-methyl-imidazolium, 1-methyl-3-(4-acetate-benzyl)-imidazolium, 1-methyl-3-(2,2-dimethoxyethyl)-imidazolium, or 1-(2,4,6-trimethylphenyl)-3-(4-acetate-benzyl)-imidazolium, or a pharmaceutically acceptable salt thereof.

Other aspects and features of the present invention will become apparent to those of ordinary skill in the art upon review of the following description of specific embodiments of the invention in conjunction with the accompanying figures.

BRIEF DESCRIPTION OF THE DRAWINGS

In the figures, which illustrate, by way of example only, embodiments of the present invention:

FIG. 1. Cytotoxicity of (a) DBZIM and (b) TDBZIM. HSC T6 cells were seeded at a density of 5000 cells/well in 96-well plate, and cultured for 18-24 h in 10% PBS DMEM before the addition of various compounds (0-400 μM) in 10% FBS DMEM for 48 h of proliferation before assaying. The signal was normalized against a vehicle control treatment (0 μM of compound). The data were obtained from four independent experiments, and presented as mean and standard error or mean (SEM), *$^a$P<0.05, *$^b$P<0.01 and *$^c$P<0.005.

FIG. 2. (a) DBZIM and (b) TDBZIM attenuated cellular ROS level. HSC T6 cells were incubated with DBZIM (10, 50, 100 and 300 μM), TDBZIM (10, 50 and 100 μM), NAC (1 mM) and EGCG (25 μM) for 48 h before assaying for cellular ROS levels. The data were presented as relative values after normalizing against a vehicle control. The data were presented as mean and SEM, N=6, *$^b$P<0.01, *$^c$P<0.005, and *$^d$P<0.0005 when compared to the vehicle, control.

FIG. 3. Effect of DBZIM and TDBZIM on amount of GSH (a) DBZIM attenuated total cellular GSH amount, and (b) TDBZIM did not change the total GSH. (c) DBZIM and (d) TDBZIM both suppressed cellular GSSG (the oxidation product of GSH). (e) DBZIM and (f) TDBZIM both enhanced the GSH/GSSG ratio. HSC-T6 cells were incubated with compounds of various concentrations for 48 h, and assayed for the total GSH and GSSG amounts. The GSH/GSSG ratio was calculated as (GSH−GSSG)/GSSG. The GSH and GSSG amounts were normalized against the total protein. Note that DBZIM was dissolved in DMSO, and TDBZIM was dissolved in $H_2O$. The data were presented as mean and SEM, N=6, *$^a$P<0.05, *$^b$P<0.01, *$^c$P<0.005, and *$^d$P<0.0005, when compared to the vehicle control.

FIG. 4. Effect of DBZIM and TDBZIM on GPx, CAT, SOD and GST. DBZIM affected (a) GPx activity and (c) CAT activity in a dosage-dependent manner. TDBZIM suppressed (b) GPx activity and (d) CAT activity. (e) DBZIM and (f) TDBZIM had little effect on SOD activity. (g) DBZIM induced GST activity. HSC T6 cells were treated with compounds of various concentrations for 48 h, and homogenized by sonication (60% frequency for 30 s) in PBS (pH 7.4, 1 mM of EDTA) for GPx, GST and CAT assays, or in 20 mM of HEPES buffer containing 1 mM of EGTA, 210 mM of mannitol and 70 mM of sucrose (pH 7.2) for SOD assay. Enzyme activity was normalized against total protein. DBZIM was dissolved in DMSO, and TDBZIM was dissolved in $H_2O$. The data were presented as mean and SEM, N=6, *$^a$P<0.05, *$^b$P<0.01, *$^c$P<0.005, and *$^d$P<0.0005, when compared to the vehicle control.

FIG. 7. DBZIM (100 μM) and TDBZIM (100 μM) suppressed (a) GFAP, (b) SMAA, (c) col1a1 and (d) fibronectin mRNA expression in a time-dependent manner. HSC T6 cells were treated with DBZIM and TDBZIM, and assayed after 8, 24 and 48 h. A transient elevation of SMAA expression was observed for TDBZIM at 24 h. The mRNA expression was calculated using the ΔΔCt method by normalizing to β-actin house-keeping gene and vehicle control sample, and presented as relative quantification data with mean and SEM, N=6, *$^a$P<0.05, *$^b$P<0.01, *$^c$P<0.005, and *$^d$P<0.0005, when compared to the vehicle control.

FIG. 9. DBZIM and TDBZIM suppressed TGF-β1 mRNA. HSC T6 cells were incubated with (a) DBZIM (1, 10, 100 and 300 μM) and (b) TDBZIM (1, 10 and 100 μM) for 48 h for the dosage-dependent study, and (c) with DBZIM (100 μM) and TDBZIM (100 μM) for 8, 24 and 48 h for the time-dependent study. The expression level of TGF-β1 mRNA was quantified with real-time RT-PCR. The data were presented as mean and SEM, N=6, *$^a$P<0.05, *$^b$P<0.01, *$^c$P<0.005, when compared to vehicle control.

FIG. 10. DBZIM and TDBZIM suppressed IL-6 mRNA. HSC T6 cells were incubated with DBZIM (1, 10, 100 and 300 μM) and (b) TDBZIM (1, 10 and 100 μM) for 48 h for the dosage-dependent study, and (c) with DBZIM (100 μM) and TDBZIM (100 μM) for 8, 24 and 48 h for the time-dependent study. The expression level of IL-6 mRNA was quantified with real-time RT-PCR. The data were presented as mean and SEM, N=6, *$^b$P<0.01, *$^c$P<0.005, and *$^d$P<0.0005, when compared to the vehicle control.

FIG. 14. Real-time PCR quantification of (a) GFAP, (b) SMAA, (c) fibronectin and (d) col1a1 mRNA expressions in HSC T6 cells treated with various IMSs for 48 h. DBIM (1 mM), AMIM (50 μM), TMPHIM (50 μM), DPPHIM (10 μM) and DBZBIM (100 μM) were dissolved in DMSO with a final DMSO concentration of 0.2% (v/v). DPIM (2 mM), EGCG (25 μM) and DBZIM (100 μM) were dissolved in H$_2$O. β-actin was used as the normalization gene; its expression was constant under the experimental conditions. Relative quantification was normalized against the respective vehicle control. The data were presented as mean and SEM, N=6, *$^a$P<0.05, *$^c$P<0.005, and *$^d$P<0.0005, when compared to the vehicle control.

FIG. 21. DBZIM inhibited cell proliferation and disrupted cell cycle in HLE cells (A). DBZIM inhibited HCC cell proliferation. HLE cells were seeded at a density of 5000 cells/well in 96-well plate, and cultured for 18-24 h in 10% PBS DMEM before the addition of various compounds (0-1.25 mM) in 10% FBS DMEM for 48 h of proliferation before assaying. Cell count was calculated based on Hoechst dye staining and BrdU incorporation was based on the total fluorescence intensity of antibody staining. (B). DBZIM arrested HCC cells at G0/G1 phase. HLE cells were incubated with DBZIM (0, 1, 3 mM) for 24 hr before fixation and DAPI staining for DNA content (2N vs. 4N) determination.

FIG. 29. DMZIM induced apoptosis. Pictures from phase-contrast microscopy show the apoptotic morphology of gastric cancer cell AGS (A) and lung cancer cell H1299 (B) after exposure to DBZIM for 72 h, respectively. Extending the length of exposure caused increased loss of confluence with apoptotic cells in cell cultures.

FIG. 31. DBZIM induces cleavage of caspase-3, caspase-9 and PARP as indication of apoptosis. Western blot analysis for the effect of DBZIM, on the cleavage of caspase-3, Caspase-9 and PARP A) in p53 wild type gastric cancer cell AGS and B) in p53 wild type breast cancer cell line MCF-7. Western blot analysis conducted on cells after 72 h exposure to 50 µM of DBZIM.

FIG. 37. IMSs arrest Hepatocarcinoma cells. Cells were treated with vehicle and IBN 15, IBN 19, IBN 24, IBN 25 and IBN 32 for 72 h, and cell cycle distribution was assessed by flow cytometry. A) Example FACS profiles of propidium iodide-stained control cells, and cells treated with IMSs respectively. B) % of cells in cell cycle phase C) % of cells in subG0 population. Each value is the mean±S.D. of three determinations.

FIG. 40. IMSs-induced accumulation of p53 and p53 phosphorylation on serines 15, 20, 46, and 392 in p53 mutant HLE cells. (A) Hepatocarcinoma cancer cell HLE were treated with indicated concentration of IBN 15, IBN 19, IBN 24, IBM 25 and IBN 32 for 72 h. The levels of phosphorylation of p53 protein and Ser-15, Ser-20, Ser-46 and Ser-392 were determined by Western blotting. β-actin was used as a loading control.

FIG. 41. IMSs-induced apoptosis through the initiation of the mitochondrial pathway. Cells were treated with various IMSs and the levels of Bcl-2 and BAX were assessed by Western blot assay.

Figure 5B:
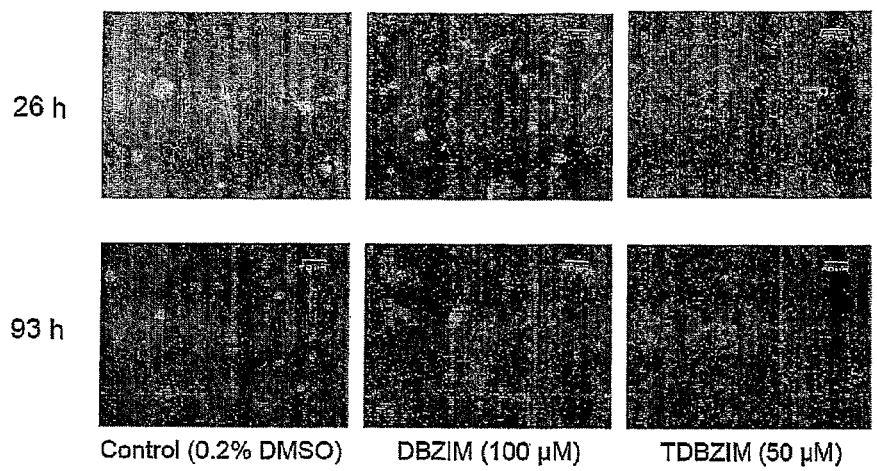
FIG. 5. DBZIM and TDBZIM protected primary HSC cells against oxidative stress induced by 0.2% (v/v) of DMSO. (a) Optical images of cells treated with IMSs for 26 and 93 h. Scale bar=60 μm. 0.2% (v/v) of DMSO induced oxidative stress by depleting the total GSH level (b), inducing the GSSG level (c), reducing the GSH/GSSG ratio (d), and inducing GPX (e), CAT (f) and SOD (g) activity levels. The data were presented as mean and SEM, N=6, *$^c$P<0.005, and *$^d$P<0.0005; when compared to the untreated sample.
Figure 5C:
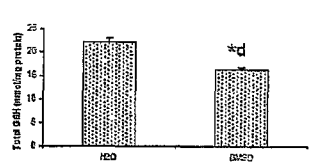
Figure 5D:
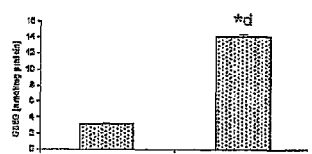
Figure 5E:
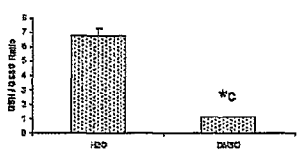
Figure 5F:
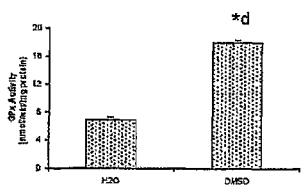

Table 1. Names and Structures of IMSs.
Table 2. IC50 values of IMSs.
Table 3. IC50 values of DBZIM in various cancer cell lines.
Table 4. IC50 values of IBN-15, 19, 24, 25 and 32 in HEX cells.
Table 5. IC50 values of DBZMIM and Compound 9 in gastric cancer cells.
Table 6. IC50 values of DBZMIM and Compound 9 in breast cancer cells.
Table 7. IC50 values of DBZMIM and Compound 9 in normal breast cells.

DETAILED DESCRIPTION

The methods described herein relate to the discovery that the imidazolium and imidazolinium compounds (collectively "IMSs") as described herein, including in the form of imidazolium and imidazolinium salts, may be used as anti-fibrotic and anti-cancer agents or to treat fibrotic disease or cancer. The inventors have synthesized novel IMSs that may be used in the methods described herein.

Both imidazolium and imidazoliniums are based on an imidazole ring and both are N,N'-substituted; imidazoliums are N,N'-substituted imidazoles, while imidazoliniums are N,N'-substituted imidazolines and do not have the carbon-carbon double bond between positions C4 and C5 that is present in imidazole. Imidazole itself is incorporated in many biological molecules, and synthetic C-substituted imidazoles have become an important part of many pharmaceuticals (Olmos et al. 1999) (Casanovas et al. 2000).

One attractive feature of using IMSs in synthetic chemistry is the structural versatility they provide. The electronic structure and stability, and thus the therapeutic safety and efficacy of IMSs, can be fine-tuned by varying the N-substituents (substituents on the nitrogen atoms of the central ring) and the central ring of the molecule. It will be understood that the "central ring" of IMSs refers to the five membered ring containing 2 nitrogen atoms (either the imidazole or imidazoline ring) to which various substituents may be bound to create different IMS molecules. IMSs provide inexpensive and chemically tunable building blocks for the development of novel therapeutics.

Some IMSs are precursors of N-heterocyclic carbenes (NHCs). NHCs can be easily generated from IMSs having a hydrogen atom at the C2 position of the central ring and substituents on both nitrogen atoms of the central ring i.e. two N-substituents. NHCs are generated from these IMSs by the deprotonation of the IMS under the appropriate conditions. Deprotonation of IMSs may be carried out under basic conditions or in a diluted solution under neutral conditions.

It is difficult to generate NHCs from IMSs with substituents other than a hydrogen atom at the C2 position of the central ring. However radical species may be formed from these IMSs by cleaving the N-substituents.

The inventors have discovered that the IMSs as described herein may be used as anti-fibrotic or anti-cancer agents or to treat fibrotic disease or cancer. Without being limited to any particular theory, the IMSs as described herein may exhibit anti-oxidative and properties. Both fibrotic disease and cancer have been linked to oxidative stress response. In turn, in both fibrotic disease and cancer, oxidative stress has been shown to be closely linked with inflammatory response.

IMSs that may be used as anti-fibrotic agents or as anti-cancer agents are compounds having a structure of the general formula I:

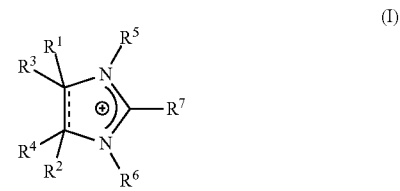

(I)

In formula I, the dashed line is absent or is present as a bond to form a second bond between the carbon to which $R^1$ and $R^3$ are attached and the carbon to which $R^2$ and $R^4$ are attached. Thus, the carbon to which $R^1$ and $R^3$ are attached and the carbon to which $R^2$ and $R^4$ are attached may be connected by either a single bond or a double bond.

$R^1$ and $R^2$ (i) are each independently H, straight or branched $C_1$-$C_6$ alkyl, straight or branched $C_2$-$C_6$ alkenyl, straight or branched $C_2$-$C_6$ alkynyl, $C_6$-$C_{10}$ aryl; or (ii) together with their ring atoms form a 6- to 10-membered fused saturated, unsaturated or aromatic ring system; or (iii) $R^1$ and $R^5$ together with their ring atoms or $R^2$ and $R^6$ together with their ring atoms, form a 5- to 10-membered fused saturated, unsaturated or aromatic ring system and the other of $R^1$ and $R^2$ is as defined above in (i); or (iv) $R^1$ and $R^5$ together with their ring atoms and $R^2$ and $R^6$ together with their ring atoms form 5- to 10-membered fused saturated, unsaturated or aromatic ring system.

$R^3$ and $R^4$ are both H, or, when $R^1$ and $R^2$ together with their ring atoms form a 6- to 10-membered fused aromatic ring system or when the dashed line is present as a bond, $R^3$ and $R^4$ are absent.

When $R^5$ or $R^6$ is not fused together with $R^1$ or $R^2$, respectively, as set out above, $R^5$ and $R^6$ are each independently straight or branched $C_1$-$C_6$ alkyl, straight or branched $C_2$-$C_6$ alkenyl, straight or branched $C_2$-$C_6$ alkynyl, $C_3$-$C_{18}$ cycloalkyl including fused cycloalkyl ring systems, $C_6$-$C_{10}$ aryl, $C_6$-$C_{10}$ aryl-$C_1$-$C_6$ alkyl, $C_6$-$C_{10}$ aryl-$C_2$-$C_6$ alkenyl, or $C_6$-$C_{10}$ aryl-$C_2$-$C_6$ alkynyl, $C_1$-$C_6$ alkyl-$C_6$-$C_{10}$ aryl, $C_2$-$C_6$ alkenyl-$C_6$-$C_{10}$ aryl, or $C_2$-$C_6$ alkynyl-$C_6$-$C_{10}$ aryl.

$R^7$ may be H, $C_1$-$C_6$ alkyl, phenyl, substituted $C_1$-$C_6$ alkyl or halo.

Any of the above substituents $R^1$ to $R^7$, where applicable, may optionally have one or more carbon atoms replaced with a heteroatom selected from N, O, S and P. As well, any of the above substituents $R^1$ to $R^7$, where applicable, may optionally be substituted with one or more of straight or branched $C_1$-$C_6$ alkyl, straight or branched $C_2$-$C_6$ alkenyl, straight or branched $C_2$-$C_6$ alkynyl, $C_3$-$C_{18}$ cycloalkyl including fused cycloalkyl ring systems, $C_6$-$C_{10}$ aryl, fluoro, tri-fluoro-methyl, cyanato, isocyanato, carboxyl, $C_1$-$C_6$ acyloxy, $C_1$-$C_6$ acyl, carbonyl, amino, acetyl, acetoxy, oxo, nitro, hydroxyl, $C_1$-$C_6$ alkylcarboxy, $C_1$-$C_6$ alkoxy, $C_2$-$C_6$ alkenoxy, $C_2$-$C_6$ alkynoxy.

One of the ring carbon atom to which $R^1$ and $R^5$ are attached and the ring carbon to which $R^2$ and $R^6$ are attached may be optionally replaced with a nitrogen atom.

The above compounds may be present in salt form. Thus, IMSs that may be used in the present methods include pharmaceutically acceptable salts of compounds of formula I and oligomers and polymers of such salts. Such salts have a structure of the general formula II:

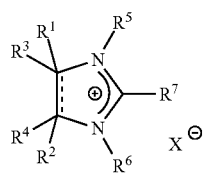
(II)

General formula II is as defined above for general formula I, with the further feature of counterion X. X is a pharmaceutically acceptable anion, including but not limited to chloride, bromide, tetrafluoroborate, hexafluorophosphate.

The term "fused" as used herein in reference to ring structures refers to the sharing of at least two atoms between ring structures. When two ring atoms (either of which may be C or N) are included in a fused ring system, the ring system is fused to the central imidazolium or imidazolinium ring.

In particular embodiments, the dashed line may be absent or is present as a bond to form a second bond between the carbon to which $R^1$ and $R^3$ are attached and the carbon to which $R^2$ and $R^4$ are attached; $R^1$ and $R^2$ are both H or together with their ring atoms form a 6- to 10-membered fused aromatic ring system; $R^3$ and $R^4$ are both H or nothing; $R^5$ and $R^6$ are each independently straight or branched $C_1$-$C_6$ alkyl, straight or branched $C_2$-$C_6$ alkenyl, straight or branched $C_2$-$C_6$ alkynyl, $C_3$-$C_{18}$ cycloalkyl including fused cycloalkyl ring systems, $C_6$-$C_{10}$ aryl, $C_6$-$C_{10}$ aryl-$C_1$-$C_6$ alkyl, $C_6$-$C_{10}$ aryl-$C_2$-$C_6$ alkenyl or $C_6$-$C_{10}$ aryl-$C_2$-$C_6$ alkynyl; $R^7$ is H; any of which substituents $R^1$ to $R^7$, where applicable may have one or more carbon atoms replaced with a heteroatom selected from N, O, S and P and any of which may optionally be substituted with one or more of straight or branched $C_1$-$C_6$ alkyl, straight or branched $C_2$-$C_6$ alkenyl, straight or branched $C_2$-$C_6$ alkynyl, $C_3$-$C_{18}$ cycloalkyl including fused cycloalkyl ring systems, $C_6$-$C_{10}$ aryl, fluoro, trifluoro-methyl, cyanato, carboxyl, carbonyl, amino, acetyl, oxo, nitro, $C_1$-$C_6$ alkoxy, $C_2$-$C_6$ alkenoxy, $C_2$-$C_6$ alkynoxy.

For example, in various embodiments, the compound may be an imidazolium salt, with a double bond between the two ring atoms to which $R^1$ and $R^2$ are attached. In various other embodiments, the compound may be an imidazolinium salt, wherein $R^3$ and $R^4$ are hydrogens and there is only a single bond between their ring carbons. In yet other embodiments, $R^3$ and $R^4$ are nothing and $R^1$ and $R^2$ together with their ring atoms form a 6- to 10-membered fused aromatic ring system.

The substituents comprising $R^5$ and $R^6$ may also vary. For example, in some embodiments, the IMS of the present method may be a compound wherein $R^5$ and $R^6$ are the same. In different embodiments, $R^5$ or $R^6$ may be aralkyls, branched alkyls or cycloalkyls including fused ring systems. In other embodiments $R^5$ or $R^6$ may comprise a phenalkyl group. In other embodiments, one or both of $R^5$ and $R^6$ may comprise an adamantanyl group.

IMSs that may be used in the present method also include oligomers or polymers formed from compounds of general formula I. Thus, "oligomer" as used herein, refers to, for example, 2 or more, 3 or more, 4 or more, 5 or more, 10 or more, 15 or more, 20 or more, 25 or more, 50 or more, 100 or more, 150 or more compounds of general formula I connected together in the manner described below. Thus, oligomer includes dimers and trimers. "Polymers" as used herein refers to, for example, 100 or more, 150 or more, 200 or more, 250 or more, 500 or more, 1000 or more compounds of general formula I connected together in the manner described below.

In oligomers or polymers as used herein, compounds of general formula I are connected to each other to form a macromolecular structure, which may be cyclised.

For example, trimers as described herein include 1,3,5-tris(4-methyl-imidazolium)-linked cyclophane or a pharmaceutically acceptable salt thereof (TDBZIM).

In the macromolecular structure, two compounds of general formula I may be connected together so that one or more $R^1$, $R^2$, $R^5$, $R^6$ or $R^7$ substituent is bivalent and is thus shared between the two compounds, rather than have a relevant substituent present in the oligomer or polymer for every compound of general formula I present. For example, in such a dimer, two compounds may be connected by a shared bivalent $R^1$ substituent, and thus in the complete dimer, there is only one occurrence of an $R^1$ substituent for the two compounds of general formula I.

Thus, the compounds of general formula I may be joined to each other via a bivalent substituent such as $R^1$, $R^2$, $R^5$, $R^6$, or $R^7$. For example, an $R^5$ substituent on one compound of general formula I may also be $R^5$ on a second compound of general formula I such that the two compounds are linked via a shared $R^5$ substituent. Similarly, oligmers or polymers may be formed by linking compounds via shared $R^1$, $R^2$, $R^5$, $R^6$, or $R^7$ substituents. For example, dimers of this description include 2,6-di-(3-benzyl-imidazolium bromide)-pyridine or a pharmaceutically acceptable salt thereof (IBN-22).

Sharing of substituents as described above can include sharing of two substituents that together with their ring carbons form a fused ring system. Thus, for example, if $R^1$ and $R^2$ together with their ring carbons form a ring system on a first compound of formula I, additional carbons within the ring will be ring carbons from a second compound of general formula I. For example, dimers of this description include benzo(1,2-4,5-diimidazolium)-N,N',N'',N'''-tetrabenzyl-dibromide or a pharmaceutically acceptable salt thereof (IBN-29).

Alternatively, a substituent such as one or more of $R^1$, $R^2$, $R^5$, $R^6$ or $R^7$ may be bonded to another such substituent on a second compound in order to connect two compounds together to form an oligomer or polymer, and thus there will be one occurrence of the relevant linking substituent for each compound of general formula I in the oligomer or polymer. Multiple compounds falling within general formula I may be joined together (oligomerised) in this way, by one or more shared bivalent $R^1$, $R^2$, $R^5$, $R^6$ or $R^7$ substituents. For example, such dimers include 2,2'-di-(3-benzyl-imidazolium bromide)-1,1'-binaphthalene or a pharmaceutically acceptable salt thereof (IBN-23).

Additionally, two compounds of general formula I may be attached by a single or double bond between respective carbon atoms to which $R^7$ is attached in general formula I to form a dimer. These molecules include for example, 1,3-dibenzyl-2-(1,3-dibenzyl-1H-imidazol-2(3H)-ylidene)-2,3-dihydro-1H-imidazole or a pharmaceutically acceptable salt thereof (compound H).

The oligomerised or polymerised compounds may be the same compound, such that all substituents in general formula I are the same in each oligomerised or polymerised compound, or may be different, with one or more substituents differing between compounds, with the exception that shared bivalent substituent or substituents will obviously be the same in the compounds in which the bivalent substituent is shared.

Table 1 contains the names and structures, of particular examples of the IMSs described herein.

In particular embodiments, the compounds of the present invention may be 1-ethyl-3-methylimidazolium, 1,3-bisbenzylimidazolium, 1,3-diisopropylimidazolium, 1,3-di-tert-butylimidazolinium, 1,3-bis(1-adamantyl)imidazolium, 1,3-bis(2,4,6-trimethylphenyl)-imidazolinium, 1,3-bis(2,6-diisopropyl-phenyl)-imidazolinium, 1,3-diallylimidazolium, 1-benzyl-3-methylimidazolium, 1-butyl-3-methylimidazolium, 1-(1-adamantyl)-3-(2,4,6-trimethylphenyl)-4,5-dihydroimidazolium, 2-benzylimidazo[1,5-a]quinolinium, 1,3-bis(1-adamantyl)-benzimidazolium, 1,3-dicyclohexylbenzimidazolium, 1,3-diisopropylimidazolinium tetrafluoroborate, 1,3-diisopropylimidazolium, 2-(2,6-diisopropylphenyl)-5-methylimidazo[1,5-a]pyridinium, diisopropylphenyl)-3-(2,4,6-trimethylphenyl)-imidazolinium, 2-mesityl-5-methylimidazo[1,5-a]pyridinium, 2-mesityl-2,5,6,7-tetrahydropyrrolo[2,1-c][1,2,4]triazol-4-ium, 1,3-bis(1-adamantyl)imidazolinium, 1-butyl-3-(2-pyridinylmethyl)-1H-imidazolium, 6,7-dihydro-2-pentafluorophenyl-5H-pyrrolo[2,1-c]-1,2,4-trizolium, or any pharmaceutically acceptable salt thereof.

In particular embodiments, the compounds of the present invention may be 1-ethyl-3-methylimidazolium bromide, 1,3-bisbenzylimidazolium bromide (DBZIM), 1,3-diisopropylimidazolium tetrafluoroborate (DPIM), 1,3-di-tert-butylimidazoliniumtetrafluoroborate (DBIM), 1,3-bis(1-adamantyl)imidazolium tetrafluoroborate (AMIM), 1,3-bis(2,4,6-trimethylphenyl)-imidazolinium chloride (TMPHIM), 1,3-bis(2,6-diisopropyl-phenyl)-imidazolinium chloride (DPPHIM), 1,3-diallylimidazolium bromide (Compound D), 1-benzyl-3-methylimidazolium bromide (Compound E), 1-butyl-3-methylimidazolium chloride (Compound G), 1-(1-adamantyl)-3-(2,4,6-trimethylphenyl)-4,5-dihydroimidazolium chloride (Compound S1), 2-benzylimidazo[1,5-a]quinolinium chloride (Compound S2), 1,3-bis(1-adamantyl)-benzimidazolium chloride (Compound S3), 1,3-dicyclohexylbenzimidazolium chloride (Compound S6), 1,3-diisopropylimidazolinium tetrafluoroborate (Compound S7), 1,3-diisopropylimidazolium chloride (Compound S8), 2-(2,6-diisopropylpheneyl)-5-methylimidazo[1,5-a]pyridinium hexafluorophosphate (Compound S9), 1-(2,6-diisopropylphenyl)-3-(2,4,6-trimethylphenyl)-imidazolinium chloride (Compound S10), 2-mesityl-5-methylimidazo[1,5-a]pyridinium chloride (Compound S11), 2-mesityl-2,5,6,7-tetrahydropyrrolo[2,1-c][1,2,4]triazol-4-ium chloride (Compound S12), 1,3-bis(1-adamantyl)imidazolinium tetrafluoroborate (Compound S13), 1-butyl-3-(2-pyridinylmethyl)-1H-imidazolium hexafluorophosphate (Compound S14), 6,7-dihydro-2-pentafluorophenyl-5H-pyrrolo[2,1-c]-1,2,4-trizolium tetrafluoroborate (Compound S15).

The compounds of general formula I include novel compounds, including 1-ethyl-3-methylimidazolium, 1-methyl-3-(2-hydroxylethyl)-imidazolium, 1-methyl-3-(4-isocynatobenzyl)-imidazolium, 1-methyl-3-(4-carboxylbenzyl)-imidazolium, 1-methyl-3-(4-acetate-benzyl)-imidazolium, 1-methyl-3-(2,2-dimethoxylethyl)-imidazolium, 1-(2,4,6-trimethylphenyl)-3-(4-acetate-benzyl)-imidazolium, 1,3-Dibenzyl-5-phenylimidazolium, 1-benzyl-3-(4-carboxylbenzyl)-2-methylimidazolium, 1-benzyl-3-(3,4,5-trimethoxylbenzyl)-2-methylimidazolium, 1-benzyl-3-(4-acetate-benzyl)-2-methyl-imidazolium, 1-benzyl-3-(4-methylcarboxylatebenzyl)-2-methylimidazolium, 1-benzyl-3-(2,2-dimethoxylethyl)-2-methyl-imidazolium, 2,6-di-(3-benzyl-imidazolium)-pyridine, 2,2'-di-(3-benzyl-imidazolium)-1,1'-binaphthalene, 1-benzyl-3-(4-methylbenzyl)-imidazolium, 1-benzyl-3-(2-trifluoromethylbenzyl)-2-methylimidazolium, 1-benzyl-3-(4-methylcarboxylatebenzyl)-5-phenyl-imidazolium, 1-benzyl-3-(4-acetatebenzyl)-5-phenyl-imidazolium, 1-benzyl-3-(4-methylbenzyl)-5-phenylimidazolium, (1,2-4,5-diimidazolium)-N,N',N'',N'''-tetrabenzyl-benzene, 1-benzyl-3-(2-propyn-1-yl)-imidazolium, 1-benzyl-3-(3-hydroxylpropyl)-imidazolium, 1,3-di(2-phenylethyl)-imidazolium, 1-benzyl-3-(4-acetatebenzyl)-imidazolium, 1-benzyl-3-(pyridin-2-yl)-imidazolium, 1,3,5-tris-(4-methyl-imidazolium)-linked cyclophane, 1,3-dibenzyl-2-(1,3-dibenzyl-1H-imidazol-2(3H)-ylidene)-2,3-dihydro-1H-imidazole, 1-benzyl-3-methyl-imidazolium, 1-(4-cyanatobenzyl)-3-methyl-imidazolium, 1-(4-carboxybenzyl)-3-methyl-imidazolium, 1-methyl-3-(4-acetate-benzyl)-imidazolium, 1-methyl-3-(2,2-dimethoxyethyl)-imidazolium, and 1-(2,4,6-trimethylphenyl)-3-(4-acetate-benzyl)-imidazolium, or any pharmaceutically acceptable salt thereof.

The compounds of general formula I include novel compounds, including 1-ethyl-3-methylimidazolium bromide, 1-methyl-3-(2-hydroxylethyl)-imidazolium bromide (IBN-2), 1-methyl-3-(4-isocynatobenzyl)-imidazolium chloride (IBN-3), 1-methyl-3-(4-carboxylbenzyl)-imidazolium bromide (IBN-4), 1-methyl-3-(4-acetate-benzyl)-imidazolium chloride (IBN-6), 1-methyl-3-(2,2-dimethoxylethyl)-imidazolium bromide (IBN-8), 1-(2,4,6-trimethylphenyl)-3-(4-acetate-benzyl)-imidazolium chloride (IBN-9), 1,3-Dibenzyl-5-phenylimidazolium bromide (IBN-15), 1-benzyl-3-(4-carboxylbenzyl)-2-methylimidazolium chloride (IBN-17), 1-benzyl-3-(3,4,5-trimethoxylbenzyl)-2-methylimidazolium chloride (IBN-18), 1-benzyl-3-(4-acetate-benzyl)-2-methyl-imidazolium chloride (IBN-19), 1-benzyl-3-(4-methylcarboxylatebenzyl)-2-methyl-imidazolium chloride (IBN-20), 1-benzyl-3-(2,2-dimethoxyethyl)-2-methyl-imidazolium bromide (IBN-21), 2,6-di-(3-benzyl-imidazolium bromide)-pyridine (IBN-22), 2,2'-di-(3-benzyl-imidazolium bromide)-1,1'-binaphthalene (IBN-23), 1-benzyl-3-(4-methylbenzyl)-imidazolium chloride (IBN-24), 1-benzyl-3-(2-trifluoromethylbenzyl)-2-methylimidazolium chloride (IBN-25), 1-benzyl-3-(4-methylcarboxylatebenzyl)-5-phenyl-imidazolium bromide (IBN-26), 1-benzyl-3-(4-acetate-benzyl)-5-phenyl-imidazolium bromide (IBN-27), 1-benzyl-3-(4-methylbenzyl)-5-phenylimidazolium chloride (IBN-28), Benzo(1,2-4,5-diimidazolium)-N,N',N'',N'''-tetrabenzyl-, di-bromide (IBN-29), 1-benzyl-3-(2-propyn-1-yl)-imidazolium bromide (IBN-30), 1-benzyl-3-(3-hydroxyl-propyl)-imidazolium bromide (IBN-31), 1,3-di(2-phenylethyl)-imidazolium bromide (IBN-32), 1-benzyl-3-(4-acetatebenzyl)-imidazolium chloride (IBN-33), 1-benzyl-3-(pyridin-2-yl)-imidazolium bromide (IBM-34), 1,3,5-tris-(4-methyl-imidazolium)-linked cyclophane 3Br (TDBZIM), 1,3-dibenzyl-2-(1,3-dibenzyl-1H-imidazol-2(3H)-ylidene)-2,3-dihydro-1H-imidazole (compound H), 1-benzyl-3-methyl-imidazolium bromide (compound 12), 1-(4-cyanatobenzyl)-3-methyl-imidazolium chloride, 1-(4-carboxybenzyl)-3-methyl-imidazolium bromide, 1-methyl-3-(4-acetate-benzyl)-imidazolium chloride, 1-methyl-3-(2,2-dimethoxyethyl)-imidazolium bromide, and 1-(2,4,6-trimethylphenyl)-3-(4-acetate-benzyl)-imidazolium chloride.

The compounds of general formula I and oligomers and polymers thereof are commercially available or may be synthesized using routine chemistry, as described in the Examples set out below. Methods of synthesis have also been described in Harlow et al. 1996, Zhang et al. 2007; Chianese and Cratree 2005 and Boydston et al. 2005.

Thus, there is presently provided a method for delivering an anti-fibrotic or anti-cancer agent to a cell, the method comprising contacting the cell with an effective amount of a compound of general formula I, a pharmaceutically acceptable salt thereof or an oligomer or polymer thereof.

As used herein, "delivering" an anti-fibrotic or anti-cancer agent to a cell refers to providing the agent in sufficiently close proximity to the cell such that the agent can exert its anti-fibrotic or anti-cancer effects on the cell. In vitro, for example, the agent may be delivered to the cell by adding the agent to the cell culture media. In vivo, for example, the agent may be delivered by administering the agent to a subject as a pharmaceutical composition.

As used herein, "contacting" a cell refers to direct and indirect contact with the cell. Direct contact refers to a direct interaction between the agent and the cell. In contrast, indirect contact involves "contacting the cell" via interactions with other molecules or compounds. For example, the agent may interact with a molecule, affecting a change in that molecule that causes it to interact with the cell or interact with another molecule which will then interact with the cell to exert an effect. Indirect contact may involve a series of molecular interactions resulting in an effect on the cell.

An anti-fibrotic agent as used herein refers to a compound that alters, reduces or inhibits molecules, mechanisms or effects associated with fibrotic disease. For example, the agent may be an anti-inflammatory or an anti-oxidative, induce apoptosis, alter, reduce or inhibit the activity of fibrogenic mediators such as TGF-β, NF-κB or IL-6 or neutralize proliferative, fibrogenic, contractile or pro-inflammatory responses of cells. Without being limited to any particular theory, the anti-fibrotic agent may reduce or inhibit fibrotic disease by: (a) reducing inflammation to avoid stimulating activation of cells involved in fibrotic disease such as stellate cells, (b) directly down-regulating activation of cells involved in fibrotic disease, (c) neutralizing proliferative, fibrogenic, contractile or pro-inflammatory responses of cells involved in fibrotic disease, (d) inducing apoptosis such as, for example, Bcl-xL or Fas; or (e) inducing ECM degradation.

An anti-cancer agent as used herein refers to a compound that alters, reduces or inhibits molecules, mechanisms or effects associated with cancer. For example, the agent may be an anti-inflammatory or an anti-oxidative, induce apoptosis, inhibit abnormal cell growth, inhibit cell proliferation, inhibit DNA mutation or modify the activity or level of activity of molecules associated with cancer such as survivin, caspase 9, caspase 3, Bcl-$X_L$, Bak, BAX, ATM, p53, Cdc25A, Cdc2, SESN2 and AP-1.

The cell to which the anti-fibrotic or anti-cancer agent is to be provided may be any cell, including an in vitro cell, a cell in culture, or an in vivo cell within a subject. The term "cell" as used herein refers to and includes a single cell, a plurality of cells or a population of cells where context permits, unless otherwise specified. The cell may be an in vitro cell including a cell explanted from a subject or it may be an in vivo cell in a subject. Similarly, reference to "cells" also includes reference to a single cell where context permits, unless otherwise specified.

The cell may be derived from any organism, for example an insect, a microorganism including a bacterium, or an animal including a mammal including a human.

The cell of the present method may be within a subject having fibrotic disease or cancer, a subject requiring treatment for fibrotic disease or cancer or a subject in which prevention of fibrotic disease or cancer is desired. In some embodiments, the subject is a human subject.

Fibrotic disease will be understood by those skilled in the art to refer to a condition which may be characterized or caused by the development of excess fibrous tissue or over production of extracellular matrix in an organ or tissue and may include for example liver fibrosis, kidney fibrosis, lung fibrosis, bone fibrosis, systemic sclerosis, mixed connective tissue. Further examples of fibrotic disease are provided in US 2007/0043016 which is herein incoporated by reference.

In one embodiment of the present methods, an anti-fibrotic agent may be delivered to a cell in a subject having hepatic fibrosis. The compound may be for example 1,3-diisopropylimidazolium or a pharmaceutically acceptable salt thereof.

A skilled person will understand cancer to encompass a class of diseases in which cells exhibit abnormal cell growth and the potential to invade nearby tissues. In some forms of cancer, the abnormal cells may also spread to other locations in the body. Different types of cancer include for example, breast cancer, colorectal cancer, brain cancer, prostate cancer, cervical cancer, ovarian cancer, bone cancer, skin cancer, lung cancer, pancreatic cancer, bladder cancer, gallbladder cancer, kidney cancer, esophageal cancer, Hodgkin lymphoma, Non-Hodgkin lymphoma, laryngeal cancer, leukemia, multiple myeloma, oral cancer, pleural mesothelioma, small intestine cancer, testicular cancer, uterine cancer, thyroid cancer and stomach cancer.

In one embodiment of the present methods, an anti-cancer agent may be delivered to a cell in a subject having hepatocellular carcinoma, lung cancer, breast cancer, stomach cancer or glioma. The compound may be for example 1,3-Bisbenzylimidazolium, 1,3,-Dibenzyl-2-methylimidazolium, 1-(2,4,6-trimethylphenyl)-3-(4-acetate-benzyl)-imidazolium, 1,3-Dibenzyl-5-phenylimidazolium, 1-benzyl-3-(4-acetate-benzyl)-2-methyl-imidazolium, 1-benzyl-3-(4-methyl-benzyl)-imidazolium, 1-benzyl-3-(2-trifluoromethylbenzyl)-2-methylimidazolium or 1,3-di(2-phenylethyl)-imidazolium, or a pharmaceutically acceptable salt thereof.

The term "effective amount" as used herein means an amount effective, at dosages and periods of time necessary to achieve the desired result, for example to treat fibrotic disease or cancer. The total amount of IMS to be administered will vary, depending on several factors, including the severity and type of the disorder, the mode of administration, and the age and health of the subject. Methods for determining an effective amount of a particular IMS for treating fibrotic disease or cancer will be readily apparent to a person skilled in the art.

"Treating" fibrotic disease or cancer refers to an approach for obtaining beneficial or desired results, including clinical results. Beneficial or desired clinical results can include, but are not limited to, alleviation or amelioration of one or more symptoms or conditions, diminishment of extent of disorder or disease, stabilization of the state of disease, prevention of development of disorder or disease, prevention of spread of disorder or disease, delay or slowing of disorder or disease progression, delay or slowing of disorder or disease onset, amelioration or palliation of the disorder or disease state, and remission (whether partial or total). "Treating" can also mean prolonging survival of a subject beyond that expected in the absence of treatment. "Treating" can also mean inhibiting the progression of disorder or disease, slowing the progression of disorder or disease temporarily, although more preferably, it involves halting the progression of the disorder or disease permanently.

To aid in administration, the IMS may be formulated as an ingredient in a pharmaceutical composition. The compositions may contain pharmaceutically acceptable concentrations of salt, buffering agents, preservatives and various compatible carriers or diluents.

The proportion and identity of the pharmaceutically acceptable carrier is dependant on a variety of factors including the chosen route of administration, compatibility with the IMS molecule and standard pharmaceutical practice. Generally, the pharmaceutical composition will be formulated with components that will not significantly impair the biological properties of the IMS.

Suitable vehicles and diluents are described, for example, in Remington's Pharmaceutical Sciences (Remington, The Science and Practice of Pharmacy, $21^{st}$ edition, Lippincott Williams & Wilkins, Philadelphia, Pa., 2006). It would be known to a person skilled in the art how to prepare a suitable pharmaceutical composition.

The pharmaceutical composition may be administered to a subject in a variety of forms depending on the selected route of administration, as will be understood by those skilled in the art. The composition of the invention may be administered for example, by oral administration, surgically or by injection to the desired site.

In different embodiments, the composition is administered by injection (subcutaneously, intravenously, intramuscularly, etc.) directly at a desired site, for example in the vicinity of fibrotic disease or cancer that is to be treated.

The dose of the pharmaceutical composition that is to be used depends on the particular fibrotic disease or cancer disorder being treated, the severity of the condition, individual patient parameters including age, physical condition, size and weight, the duration of the treatment, the nature of concurrent therapy (if any), the specific route of administration and other similar factors that are within the knowledge and expertise of the health practitioner. These factors are known to those of skill in the art and can be addressed with minimal routine experimentation.

It will be understood that pharmaceutical compositions may be provided in a variety of dosage forms and thus, in different embodiments, IMSs may be administered in different dosage forms including for example pills, tablets, capsules, solutions, suspensions, powder and injections. Conventional procedures and ingredients for preparing and administering the different dosage forms would be known to a skilled person and are described for example, in Remington's Pharmaceutical Sciences (Remington, The Science and Practice of Pharmacy, $21^{st}$ edition, Lippincott Williams & Wilkins, Philadelphia, Pa., 2006).

Uses of the IMSs as described herein, including compounds having a structure of general formula I, a pharmaceutically acceptable salt thereof or an oligomer or polymer thereof for delivering an anti-fibrotic or anti-cancer agent to a cell in vivo and in the preparation of a medicament for delivering an anti-fibrotic or anti-cancer agent to a cell in vivo are also contemplated.

The IMSs of the present method may exert their anti-fibrotic and anti-cancer effect as a result of anti-oxidative properties, which may function via a multitude of molecular mechanisms. Anti-oxidants generally exert their effect mainly through three different pathways: (1) neutralization of cellular free radical ROS generated during metabolism and immune response, (2) induction of endogenous anti-oxidative enzymatic activity, and (3) chelation of iron or copper ions that catalyze the generation of hydroxyl radical. Without being limited to any particular theory, it appears that the anti-oxidative properties of the IMSs may result, at least in part, due to their activity as a radical scavenger. It appears that the neutralization of free radicals by IMSs may occur after a series of chemical reactions including (1) the spontaneous conversion of IMSs to NHCs preferably under a basic condition, (2) the interaction of the NHCs at the carbon 2-position with free radicals such as ROS resulting in the formation of intermediate active radicals and the neutralization of the free radicals.

The present inventors have discovered that the IMSs described herein also exhibit anti-inflammatory properties. Without being limited to any particular theory, the dual anti-oxidative and anti-inflammatory properties of the IMSs may be attributable, at least in part, to the interplay between oxidative stress and inflammation. For example, it is hypothesized that in the treatment of liver fibrosis, the anti-inflammatory effects of the IMSs compounds defined herein may be attributable to the IMSs' anti-oxidative properties that inhibit HSC activation and thus the resulting production of pro-inflammatory cytokines. Similarly, without being limited to any particular theory, the inhibition of inflammatory mediator IL-6 by an IMS may be partially attributable to the anti-oxidative properties of the MS which suppress the activation of transcription factor NF-κB, an important regulator of the secretion of inflammatory cytokines.

In addition to their anti-oxidative and anti-inflammatory properties, the IMSs may exhibit other effects that are useful in treating fibrotic disease and cancer. Anti-oxidants have been found to also have apoptosis-inducing properties. For example, EGCG, a green tea extract has shown to induce apoptosis of human hepatocellular carcinoma in cultured cell lines and a xenograft model (Nishikawa et al. 2006) while garlic extract, a natural anti-oxidant, has also been shown to induce apoptosis in human glioblastoma cells (Das et al. 2007) and colon carcinoma cells (Jakubilova et al. 2006) by inducing oxidative stress.

Without being limited to any particular theory, it appears that the IMSs may be effective in treating cancer due to inducement of apoptosis and inhibition of cell proliferation through cell cycle arrest. For example, IMSs may trigger apoptosis and cell cycle arrest by increasing or decreasing the activity and expression of molecules involved in apoptosis and cell cycling including for example survivin, caspase 9, caspase 3, Bcl-$X_L$, Bak, BAX, ATM, p53, Cdc25A, Cdc2, SESN2 and AP-1.

The present methods and compounds are further exemplified by way of the following non-limited examples.

EXAMPLES

Materials and Methods

Anti-Oxidative, Anti-Inflammatory and Anti-Fibrotic Properties of IMSs

Synthesis and Characterization of IMSs

DBZIM, TDBZIM and DBZBIM were synthesized in-house. DPIM, DBIM, AMIM, TMPHIM and DPPHIM were purchased from Sigma Chemicals (USA). The chemical structures of DBZIM (1,3-bisbenzylimidazolium bromide), DBZBIM (1,3-bisbenzyl-benzimidazolium bromide) and TDBZIM (1,3,5-tris(4-methyl-imidazolium)-linked cyclophane.3Br) are illustrated in Table 1. DBZIM and DBZBIM were synthesized using a method disclosed in the literature (Harlow et al. 1996). TDBZIM was synthesized by mixing 4-methylimidazole (123 mg, 1.5 mmol) and 2,4,6-tris (bromomethyl)mesitylene (400 mg, 1 mmol) in 200 ml of N,N'-dimethylformamide (DMF) in a reaction vial. The reaction mixture was heated to 100° C. for 2 days. Colorless crystals of TDBZIM were precipitated, and collected in 40% yield (160 mg). Nuclear magnetic resonance was conducted with the following results: $^1$H nuclear magnetic resonance (NMR) (400 MHz, $CD_3OD$): δ 7.77 (s, 1H), 5.53 (s, 2H), 5.41 (s, 2H), 4.60 (s, 1H), 2.55 (s, 3H), 2.19 (s, 6H); $^{13}$C NMR (100 MHz, $CD_3OD$): δ 143.49, 136.27, 131.73, 131.54, 123.45, 67.06, 16.35, 9.57. Elemental analysis of TDBZIM ($C_{36}H_{45}Br_3N_6$) provided the following results: C, 53.21; H, 5.88; N, 10.12 (calc. C, 53.95; H, 5.66; N, 10.49).

Primary HSC Isolation and HSC-T6 Line

The isolation of primary HSCs from Wistar rat liver was performed primarily following the method provided in a previous report (Weiskirchen et al. 2005). Briefly, the supernatant of cell suspension after hepatocyte removal was washed and re-suspended in 9.5 ml of Gey's balance salt solution (GBSS), and mixed with 8 ml of 28.7% (w/v) Histodenz in GBSS. The gradient was prepared by laying the cell suspension underneath 6 ml of GBSS, and centrifuged in Histodenz gradient at 1400×g for 20 min. The stellate cells were separated into a fuzzy band just above the interface of the Histodenz solution and the aqueous buffer. The stellate cell band was harvested, washed, and 1×10$^6$ cells/well were seeded in a 6-well culture plate in Dulbecco modified Eagle's medium (DMEM) supplemented with 10% fetal bovine serum (FBS). The viability of the HSCs was >95% as determined by trypan blue exclusion staining, and the purity of the HSCs was >90% as assessed by glial fibrillary acidic protein (GFAP) positive staining in >200 cells counted. Primary HSCs were routinely cultured in DMEM with 10% FBS in a humidified $CO_2$ incubator at 37° C., and split at 1:4 ratio by trypsinization (0.05% trypsin/0.53 mM ethylenediaminetetraacetic acid (EDTA)) when they grew to confluency. The HSC-T6 cell line was kindly provided by Dr. Scott Friedman of Mount Sinai School of Medicine, New York. A stable T6/GFAP-LacZ clonal cell line was established as previously reported (Maubach et al. 2006). HSC-T6 and T6/GFAP-LacZ cells were cultured in the same conditions as the primary HSCs.

Cell Treatment with IMSs

Stock solutions of IMSs were prepared either in dimethyl-sulfoxide (DMSO) or $H_2O$ depending on their solubility. The final DMSO concentration in the culture medium was kept below 0.2% (v/v). NAC was obtained from Merck KGaA (Germany), and EGCG was purchased from Sigma and used directly without further purification. Cells were initially seeded in cell culture plates or flasks in DMEM supplemented with 10% FBS for 18-24 h before the addition of compounds of various concentrations for different time periods. Details of the each treatment can be found in the figure legends.

Cellular ROS Determination

The ROS level of treated HSC-T6 cells was determined using the dichlorofluorescein (DCF) labeling method (Molecular Probes Inc., OR, USA). Cultured cells were harvested by trypsinization, and resuspended in phenol red-free DMEM (Invitrogen). Cells were then incubated with 10 μg/ml of 2',7'-dichloro-fluorescein diacetate (DCFH-DA) in DMEM for 15 min before resuspension in DMEM for assaying. Cell solution was dispensed into a black-wall 96-well pate in triplicate for fluorescence readout at Ex=485 nm and Em=530 nm with a Tecan Safire II plate reader. The fluorescence unit was normalized against viable cell numbers, which were determined using 3-(4,5-dimethylthiazol-2-yl)-2,5-diphenyl tetrazolium bromide (MTT assay, Promega, Wis., USA). Cellular ROS level was expressed relative to the control sample.

Glutathione (GSH) and GSH/Disulfide Dimer of Glutathione (GSSG) Assays

Total cellular GSH and GSSG levels were determined by using assay kits from Cayman Chemical (Ann Arbor, Mich., USA) following the manufacturer's instructions. Briefly, HSC-T6 cells treated with DBZIM, TDBZIM, NAC, or EGCG were scalped and homogenized in phosphate buffered saline (PBS) by sonication at 60% frequency for 30 s, and the supernatant was collected after centrifugation at 16,000×g for 10 min at 4° C. Protein content of the samples was determined by bicinchonicic acid (BCA) assay.

For GSH assays, the protein sample was deproteinated by metaphosphoric acid (Aldrich, Catalog No. 23927-5), and the pH was adjusted by triethanolamine (Aldrich, Catalog No. T5830-0) according to the manual. The sample was ready for assaying total GSH including both the reduced and oxidized forms. Quantification of GSSG, exclusive of GSH, was performed by first derivatizing GSH with 2-vinylpyridine and assaying separately. Colorimetric signal was recorded at 405 nm with a Tecan Safire II plate reader. The levels of GSH or GSSG were determined as nmol/μg protein.

Glutathione Peroxidase (GPx), Catalase (CAT) and Superoxide Dimutase (SOD) Assays Activity levels of three anti-oxidant enzymes, GPx, CAT and SOD, were determined using assay kits from Cayman Chemical. To assay GPx and CAT activities, protein samples were harvested in ice-cold PBS containing 1 mM of EDTA. To assay SOD activity, protein samples were prepared in 20 mM of N-(2-hydroxyethyl)-piperazine-N'-2-ethanesulfonic acid (HEPES) buffer containing 1 mM of ethylene glycol-bis (2-aminoethylether)-N,N,N',N'-tetraacetic acid (EGTA), 210 mM of mannitol and 70 mM of sucrose. Protein content was determined by BCA assay.

GPx activity was indirectly measured by a coupled reaction with GSH reductase. Oxidized GSH, produced upon reduction of $H_2O_2$ by GPx, is recycled to its reduced state by glutathione reductase (GR) and nicotinamide adenine dinucleotide phosphate (NADPH). The oxidation of NAPDH is proportional to the GPx activity, and can be measured as a decrease in absorbance at 340 nm. GPx activity was expressed as nmol/min/mg protein.

CAT activity was determined based on reaction of the enzyme with methanol in the presence of $H_2O_2$. The formaldehyde produced was measured spectrophotometrically at 540 nm using Purpald as the chromogen. CAT activity was expressed as nmol/min/mg protein.

Total SOD, including all three types of SOD (Cu/Zn-, Mn- and Fe-SOD), was quantified using a tetrazolium salt to detect superoxide radicals generated by xanthine oxidase and hyposanthine. One unit of SOD was defined as the amount of enzyme needed to exhibit 50% dismutation of the superoxide radical. SOD activity was expressed as U/mg protein.

Glutathione S-Transferase (GST) Assay

The activity of phase II anti-oxidant enzyme, GST, was assayed using a kit from Cayman Chemical. Protein samples were harvested in PBS buffer containing 1 mM of EDTA, and the protein concentration was determined by BCA assay. Total GST (cytosolic and microsomal) activity was assayed by measuring the conjugation of 1-chloro-2,4-dinitobenzene (CDNB) with reduced GSH, and monitored by an increase in absorbance at 340 nm. GST activity was expressed as nmol/min/mg protein.

Total RNA Isolation and Real-Time RT-PCR

Total RNA was isolated using NucleoSpin RNAII isolation kit (Nacherey & Nagel, Germany), and quantified by ND-100 spectrophotometer (Nanodrop Technologies, DE, USA). The details of real-time RT-PCR were reported elsewhere (Zhang et al. 2006). Briefly, it was a two-step real-time RT-PCR using Taqman chemistry. Total RNA was first reverse transcribed to cDNA, and real-time PCR was run and detected in ABI 7500 Fast Real-Time PCR System (Applied Biosystems, CA, USA). Primers and probes for rat GFAP, SMAA, collagen Ia1, fibronectin, TGF-β1, TGF-β receptor I (TGFβ RI) and IL-6 were ordered from Taqman's assay-on-demand database. Rat β-actin was used as normalization gene, and its expression level was constant ($C_T$ difference was <±0.5) throughout the experimental settings in this study. Relative quantification of target mRNA was calculated using comparative threshold cycle method ($\Delta\Delta C_T$) as described in User Bulletin #2 (ABI Prism 7700 Sequence Detection System). Relative quantification was given by $2^{-\Delta\Delta C_T}$ to express the up-regulation or down regulation of the target gene under the treatments compared to the control.

Western Blotting

Protein extracts were prepared by lysing a cell pellet in 10 volumes of boiled 1% sodium dodecyl sulfate (SDS) (90-95° C.) for 10 min for GFAP, or using NE-PER nuclear and cytoplasmic extraction reagents from Pierce (IL, USA) for nuclear proteins, or RIPA (Pierce, Ill., USA) for SMAA, fibronectin, collagen αI(I), TGF-β1 and TGFβ RI. Protein content was quantified using a BCA kit (Pierce, Ill., USA). 15 μg of total protein were resolved in 4-12% gradient SDS/polyacrylamide gel electrophoresis (PAGE) gel, and transferred to a nitrocellular membrane. The membrane was then probed with primary antibodies against GFAP (Dako, Denmark), SMAA (Sigma, USA), procollagen αI(I), fibronectin, c-Jun, c-Fos, JunB, JunD, Fra-1, Fra-2 (Santa Cruz Biotechnology, CA, USA), NF-κB P65, TGF-β1 and TGFβ RI (Abeam, UK), and detected by horseradish peroxidase-conjugated secondary antibody (Santa Cruz Biotechnology, CA, USA). For fibronectin and col1a1 blotting, the protein extract was separated in 3-8% tris-acetate gel. Protein bands were recorded on X-ray film by reacting with ECL chemiluminescence reagents (Amersham Biosciences, NJ, USA). Alpha-tubulin (Abeam, UK) was used as the loading control for total protein, and Tata binding protein (TBP) (Abeam, UK) was used as the loading control for nuclear protein.

Quantification of β-Galactosidase Activity

Beta-galactosidase activity in extracts from T6/GFAP-lacZ cells treated by DBZIM or TDBZIM was measured using a chemiluminescent assay kit (Roche, Mannheim, Germany) in a 96-well plate format, according to the manufacturer's instructions. Briefly, cells were washed twice with ice-cold 1×PBS (pH 7.4), and lysed for 30 min at room temperature in the lysis buffer. The supernatant was collected for assays with a Tecan Sere II plate reader. Protein concentration was determined with a BCA protein assay kit (Pierce, Ill., USA). Specific β-galactosidase activity was obtained by normalizing against total cellular protein content.

General Toxicity of IMSs in Mice

IMSs (DPIM and DBZIM) were dissolved in saline, and administered to Friend virus B-Type (FVB) mice (weighing ~25-30 g) intraperitoneally every other day for 2 weeks. The dosages were 0, 200, 300, 350, 400 and 500 mg/kg for DPIM, and 0, 10, 30, 35, 40 and 55 mg/kg for DBZIM. The injection volume was maintained at 100-160 μl. The mortality rate of mice was assessed after the treatment. The animal experimental protocol was approved by the Institutional Animal Care and Use Committee (IACUC) of Biological Resource Center (BRC) at Biopolis, Singapore.

Statistical Analysis

All quantitative results were presented as mean and standard error of mean (SEM). Experimental data were analyzed using two-tailed Student's t-test assuming unequal variances. A P-value of ≤0.05 was considered statistically significant.

Effect IMSs on Liver Fibrosis in Mice

For the liver toxin thioacetamide (TAA) model, TAA was given by i.p. injection at 200 mg/kg body weight, 3 times per week, for 12 weeks, to induce hepatic fibrosis in mice. For the bile duct ligation model (BDL), adult mice were anesthetized with Ketamine (150 mg/kg)/Xylazine (10 mg/kg) via i.p. injection. An abdominal incision at the midline is made to expose the common bile conduct, which was then ligated using 5-0 silk suture. In the control animal, the bile duct is exposed, but not ligated. DBZIM or DPIM was provided to the mice in drinking water at concentrations from 1 to 1000 mg/liter. The collagen content in the fibrotic liver was assessed by the Sirius Red staining of the liver tissue sections.

Additional studies were carried out on the effect of DPIM on liver fibrosis inducted by BDL. DPIM was purchased from Sigma Chemicals (St. Louis, Mo., USA).

Mice and Compound Dosing

Male FVB/N mice (8-10 weeks old) housed in a specific pathogen-free (SFP) facility on a 12 hour dark-light cycle and with free access to water and diet were used in the study. The animal experiment protocol was approved by the institutional animal care and use committee (IACUC), the Biomedical Research Council (BMRC) of Singapore.

Cholestatic fibrosis was induced by BDL, briefly, mice were anesthetized with intraperitoneal injection of ketamine (150 mg/kg) and xylazine (10 mg/kg), after midline laparotomy, the common bile duct was ligated twice with 5-0 silk suture. The sham operation was performed similarly except that bile duct was not double ligated. The experimental mice were divided into four groups: 1) control only (sham operated, but no BDL); 2) control+DPIM; 3) BDL only; 4) BDL+DPIM. Each group consists of 6-8 mice. DPIM compound for treatment was supplied in the drinking water at three concentrations, 500 mg/l, 750 mg/l, 1 g/l, respectively. The drinking water containing DPIM was changed weekly. It was observed that on average each mouse (normal or operated) drank approximately 3-4 ml plain or DPIM-containing water every day. Testing by NMR analysis was also conducted to confirm that DPIM is stable in water at room temperature condition for at least two weeks. The compound treatment was started on the third day after animals recovered from the BDL procedure. After 4 weeks, livers were removed from mice for fixation 10% formalin, subsequently embedded in paraffin.

Measurement of Hepatic Enzymes

Serum was collected by retro-orbital method and serum alanine transaminase (ALT) activity was measured by automated procedures with Cobase c 111 (Roche diagnostic).

Collagen Staining by Sirius Red

For consistency, paraffin-sections prepared from the left and median lobes were stained with Sirius-Red to visualize the collagen content. Briefly, after de-wax, re-hydration, air-drying, the sections were stained in 0.1% Sirius Red solution for one hour, washed twice with 0.5% acetic acid, then dehydrated in three changes of ethanol, the sections were finally cleared in xylene and mounted with Histomount (National diagnostics, Georgia, USA). The collagen stained areas were measured in at least 6 independent fields under low magnification (4×) for each left and median lobe, respectively, and quantified with Image J software.

Statistical Analysis

All images displayed are representative of 6-8 mice, unless stated otherwise. All quantitative data were expressed as mean±SE, differences among different treatment groups were analysed by two-tailed unpaired Student t-test, P value less than 0.05 were considered statistically significant.

Effect of DBZIM on Hepatocellular Carcinoma and Other Tumour Cells

DBZIM (1,3-bisbenzylimidazolium bromide) was synthesized based on a published method (Harlow et al. 1996).

Cell Culture and Compound Treatment

Human heptocellular carcinoma cell lines: HLE (an undifferentiated cell line) and HepG2 (differentiated cell line) were purchased from JCRB (Japanese Collection of Research Bioresources). Human gastric cancer cell lines AGS and MKN28, lung cancer cell line H1299, breast cancer cell line MCF-7, glioma cell line U87 MG, and C6 were all purchase from ATCC: Cell lines were routinely cultured in DMEM with 10% FBS in a humidified $CO_2$ incubator at 37° C., and split at 1:4 ratio by trypsinization (0.05% trypsin/0.53 mM ethylenediaminetetraacetic acid (EDTA) when they grew to confluence.

Stock solution of DBZIM was prepared in water. Cells were initially seeded in cell culture plates or flasks in DMEM supplemented with 10% FBS for 18-24 h before the addition of compound of various concentrations for different time periods. Details of the each treatment can be found in the figure legends.

DNA Content Analysis

HLE cells grown in a 96-well plate were treated with compounds in 6 replicates for 24 hr. Cells were then fixed with 4% paraformaldehyde and stained with DAPI. Cells were analyzed and imaged on ArrayScan VTI HCS reader (Thermal Scientific, PA, USA) and DNA content (2N vs. 4N) was determined based on DAPI staining.

Cell Proliferation Assay

HLE cells were grown, treated by compounds in 6 replicates for 48 hr in a 96-well plate. Cells were then fixed by using 4% paraformaldehyde and stained by DAPI and BrdU antibody using Hitkit (Thermo Scientific, IL, USA). Cells were imaged and analyzed on ArrayScan VTI HCS reader (Thermal Scientific, PA, USA). Cell numbers were counted based on nuclear staining and BrdU incorporation was determined and expressed as percentage of positively stained cells.

Proliferation of Glioma cell lines: U87 MG and C6 under the treatment of DBZIM was examined using 3-(4,5-dimethylthiazol-2-yl)-5-(3-carboxymethoxyphenyl)-2-(4-sulfophenyl)-2H-tetrazolium (MTS) based proliferation assay kit (Promega, Wis., USA). MTS reagent was added to the control and treated cells (after 48 hr) directly and the absorbance signal was read at 490 nm using a Tecan Safire II plate reader. Proliferation was similarly performed for gastric cancer cell line AGS, lung cancer cell line H1299, and breast cancer cell line MCF-7, but the IC50 value was determined at 72 h, instead of 48 h.

Cell Based Caspase 3/7 and LDH Assays

Capspase 3/7 activity and lactate dehydrogenase (LDH) release were measured by Fluorometric assays (Promega Corp., WI, USA). The HCC cells were cultured in 96-well plate and treated with DBZIM of various concentrations for 6 hr before assays. For caspase 3/7 assay, medium was removed and substrate buffer was added to lyse the cell and react with caspase 3/7 to give rise to fluorescence signal which was read at Ex=485 nm and Em=530 nm on a Tecan Safire II plate reader after 1 hr incubation. The caspase 3/7 activity of sample cells with the compound treatment was expressed as relative fold change after normalizing to the control cells. The LDH assay (indicative of membrane integrity) was performed using a Kit from Promega Corp according to manufactor's instructions.

Protein Extract Based Caspase 3/8/9 Colorimetric Assays

Capspase 3/8/9 activities were determined using total protein extract as starting material (Biovision Inc., CA, USA). HLE cells were cultured in T75 flask and treated with DBZIM of various concentrations. Cytosolic protein extract was collected by pelleting and lysing the cells and centrifugation to remove the debris. Capspase 3, 8 and 9 activities were assayed using the same protein extract but adding the respective substrate. Absorbance readings were taken at 405 nm using Tecan Safire II plate reader. Results were expressed as relative caspase activity by normalizing to control cells without compound treatment.

Annexin V Staining and Analysis by Cytometry

HLE and HepG2 cells were treated with various concentrations of DBZIM or TRAIL (100 ng/ml) for 24 hr, harvested and labeled with Annexin V-FITC (BioVision, CA, USA). The labeled cells were analysed by flow cytometry FACS-Calibur (Beckman-Dickson, NJ, USA) and CellQuest software. Cells showing green staining in the plasma membrane were considered as apoptotic cells.

AIF/Survivin Translocation Assay

HLE cells cultured in 96-well plate were treated with DBZIM for 24 hr before staining and imaging. Cells were then fixed and stained with antibodies against apoptosis-inducing protein (ATP) and Survivin. (Lab Vision Corp. CA, USA) and buffer reagent from Hitkit (Thermo Scientific, IL, USA). The cells were imaged and analyzed on ArrayScan VTI HCS reader (Thermal Scientific, PA, USA). Fluorescence intensity in the cytoplasmic and nuclear area was plotted for indication of cytoplasm to nucleus translocation.

SDS-PAGE and Western Blot

Protein extracts were prepared by lysing cell pellet in RIPA buffer (Pierce, Ill., USA) for total protein extract, or in NE-PER reagent from Pierce (Pierce, Ill., USA) for nuclear and cytoplasmic fractions, or in a Kit from BioVision (CA, USA) for mitochondria and cytosol fractions. Protein content was quantified using BCA Kit (Pierce, Ill., USA). Fifteen micrograms of protein were resolved in 4-12% gradient SDS/polyacrylamide gel electrophoresis (PAGE) gel, and transferred to nitrocellular membrane. The membrane was then probed with primary antibodies against Bcl-$X_L$, Bak, Bcl-$2\alpha$, Bax (Lab Vision Corp., CA, USA), survivin, xIAP, cIAP (R&D systems Inc., MN, USA), c-Jun, c-Fos, JunB, JunD, Fra-1, Fra-2 (Santa Cruz Biotechnology, CA, USA) respectively, and detected by horseradish peroxidase-conjugated secondary antibody (Santa Cruz Biotechnology, CA, USA). Protein bands were recorded on X-ray film by reacting with ECL chemiluminescence reagents (Amersham Biosciences, NJ, USA). Alpha-tubulin (Abcam, UK) was used as the loading control for total protein, Tata binding protein (TBP) (Abcam, UK) was used as the loading control for nuclear protein, and Cox4 (Abcam, UK) was used as loading control for mitochondria protein.

ROS Determination

Oxidative stress was measured using Cellomic HitKit (Thermo Scientific, IL, USA). HLE cells were treated with DBZIM for 24 hr, fixed and labeled by Dihydroethidium probe for quantitation of ROS generation and Hoechst dye for nuclear staining. The result was analyzed by Target Activation BioApplication software. The percentage of positive responding cells was plotted as the indication of ROS amount.

High-Content Analysis for Cytotoxicity and Apoptosis

Hitkit: Multiparameter Cytotoxicity 1 and Multiparameter Apoptosis 1 assay kits (Thermal Scientific, PA, USA) were used to exam the cytotoxicity and apoptosis profile of additional IMSs. Cells were cultured and treated in 96-well plate for 24 hr before assaying. Cells were fixed and stained essentially following the manufacturer's instruction. The images were taken by ArrayScan VTI HCS reader (Thermal Scientific, PA, USA) and analyzed using Cell Viability and Cell Health Profiling BioApplication software respectively.

HCC Xenograft Model and Dosing

Balb/c Nude mice, 5-6 weeks old, were inoculated with $1 \times 10^7$ Huh7 cells in 0.2 ml volume of Matrigel/DMEM mix. Since not every mouse developed a tumor after the inoculation of HCC cells, only those with visible tumors (about 8 weeks after inoculation) were used for subsequent experiment. The tumor-bearing mice were randomly divided to the control and the treatment group. (n=3), respectively. Mice in the treatment group had free access to drinking water containing DBZIM (2 grams/liter) only, while mice in the control group had free access to Water only. The compound treatment lasted for 3 weeks. The tumor size was measured weekly, and the tumor volume was calculated using the formula: $0.52 \times$ width$^2 \times$length.

Anticancer Activities of Additional IMSs

Synthesis and Characterization of IMSs

All solvents and chemicals were used as obtained from commercial suppliers, unless otherwise indicated. Centrifugation was performed on Eppendorf Centrifuge 5810R (4000 rpm, 10 min). $^1$H and $^{13}$C NMR spectra were recorded on Bruker AV-400 (400 MHz) instrument. Data for $^1$H and $^{13}$C NMR were reported in chemical shift ($\delta$ ppm) and multiplicity (s=singlet, d=doublet, t=triplet, q=quartet, m=multiplet). GC-MS was performed on Shimadzu GCMS QP2010. Gas liquid chromatography (GLC) was performed on Agilent 6890N gas chromatographs equipped with split-mode capillary injection system and flame ionization detector.

To prepare substituted imidazoles, NaH (60% in oil, 420 mg, 10.5 mmol) was added to a DMF solution of imidazole ($A_1$) (680 mg, 10 mmol) at 0° C., and the resulting suspension was stirred at room temperature for 2 h. Benzylbromide (1.71 g, 10 mmol) was added to the residue. The resulting solution was stirred at room temperature for another 4 h. The solvent was removed under vacuum. The product was extracted with dichloromethane (DCM), and $B_1$ was obtained in quantitative yield after removing the solvent. $B_2$ to $B_4$ were synthesized in the same protocol with $A_2$ to $A_4$ as imidazole starting materials. The products were confirmed by MS and NMR.

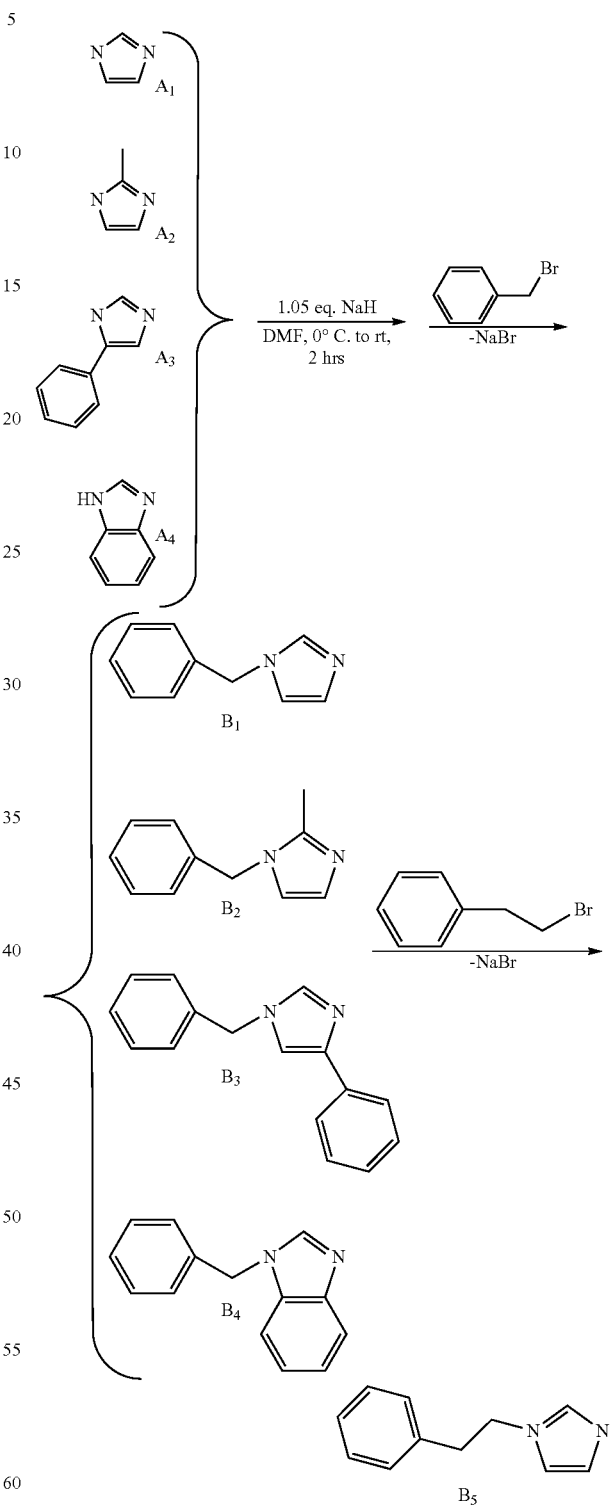

DBZIM, DBZBIM, 1,3,-Dibenzyl-2-methylimidazolium bromide (DBZMIM, Compound C), IBN-2, 3, 4, 6, 8, 9 (Compound), 12, 13, 15, 17, 18, 19, 20, 21, 24, 25, 26, 27, 28, 30, 31, 32 33, 34 were synthesized by mixing 1 mmol of substituted imidazole (like $B_1$-$B_4$) and 1 mmol of substituted benzyl bromide(chloride) or alkyl bromide(chloride) in 1 ml of DMF. The mixture was stirred at 100° C. for 16 hours. The reaction mixture was cooled down to room temperature and ether (10 ml) was added to precipitate product. The powder or gel precipitate was collected as imidazolium product and purified by re-crystalline or chromatograph method and characterized by NMR.

IBN-22, 23, 29 were made based on literature methods (Zhang et al. 2007; Chianese and Cratree 2005, Boydston et al. 2005).

The remaining IMSs listed in Table 2 were purchased from Sigma.

Typically 100 mM of stock solution of IMSs was prepared in DMSO. Aliquots of stock solution were stored until use at −20 C.

Cell Lines and Cell Culture

Human Hepatocellular cancer cell lines HLE (p53 Mutant) and human gastric cancer cell line MKN 28 were obtained from Japan Health Sciences Foundation (Osaka, Japan). The human breast cancer cell line MDAMB231 (mutant p53) and breast epithelial cells MCF-10A (wild type p53) were obtained from ATCC. These cell lines were maintained in DMEM medium (RPMI 1640 for MDAMB231) supplemented with 10% fetal bovine serum and 1% of mixture Penicillin and Stretomycin incubated at 37° C. in an atmosphere of 5% $CO_2$.

Growth Inhibition Assay

The percentage of growth inhibition was determined by using a MTT assay to measure viable cells. For the MTT assay, $1\times10^3$ cells per well were cultured in 96-well plates and treated with 0 to 100 μM of various types of IMSs for 72 h. After incubation for specified times at 37° C. in a humidified incubator, culture medium replaced with 10 μL of MTT reagent (5 mg/mL) contains 100 μL medium was added to each well and further incubated for 4 h. The reaction was stopped by adding 100 μL of DMSO. Absorbance was measured at 570 nm on a micro plate reader (SpectroMax 190, Molecular Devices). Data were presented from three separate experiments, and the percentage of IMSs induced cell growth inhibition was determined where DMSO-treated cells (control) were taken as 100%.

Cell Cycle Analysis

To perform cell cycle distribution analysis, $4\times10^5$ cells were plated in 10 cm dish. The cells (70% confluence) were serum-starved for 24 h to synchronize them in the $G_0$ phase of the cell cycle. After 24 h incubation, the cells were replaced with fresh 10% DMEM medium and then treated 60 μM of IBN-15, 90 μM of IBN-19, 90 μM of IBN-24, 30 μM of IBN-24 and 20 μM of IBN-32) and 0.045% DMSO as control for 72 h. The floating and trypsinized adherent cells were collected and washed with PBS. The cell pellets were resuspended in 1 ml of PBS and fixed by the addition of 70% ice-cold ethanol and stored at −20° C. After incubation for 24 hr, the cells were re-pelleted by centrifugation, the cells were washed once with PBS and resuspended in 0.1 mL of PBS containing 100 μg/ml of RNase and then incubated at 37° C. for 15 min. Finally, the cells were stained with 0.5 ml of PI solution (100 μg/mL in PBS) for 30 min. Cell cycle distribution was detected by a BD FACS array flow cytometer (Becton Dickinson). Cells with sub-$G_0$ DNA were classified as apoptotic cells.

Apoptosis Assay

To determine apoptosis analysis, $4\times10^5$ cells were plated in 10 cm dish. The cells were then treated with 60 μM of IBN-15, 90 μM of IBN-19, 90 μM of IBN-24, 30 μM of IBN-25 and 20 μM of IBN-32) and 0.045% DMSO as control for 72 h. The floating and trypsinized adherent cells were collected and the apoptosis was quantified using Annexin V-FITC reagent (BD Biosciences Pharmingen) and PI (Invitrogen) following the manufacturer's protocol. Briefly, the cells were washed twice with cold PBS and then resuspend cell in 100 μl of x binding buffer containing a 10 μl of Annexin V-FITC (BD-Pharminagen) and 2 μl of PI from the stock of 100 μg/ml. The cells were gently vortexed and incubated for 15 min at room temperature in the dark. Subsequently 400 μl of 1× binding buffer were added to each tube, and the samples were immediately analyzed by FACScan flow cytometer (Becton Dickinson). The fluorescent signals of the Annexin-V conjugate and PI were detected at channels of fluorescence intensity FL1 and FL2 (BD LSR II with software BD).

SDS-PAGE and Western Blotting

The HLE cells were seeded at a density of $4\times10^5$ in 10 cm dish. After 24 h incubation, the cells were replaced with fresh 10% DMEM medium and then treated with 60 μM of IBN-15, 90 μM of IBN-19, 90 μM of IBN-24, 30 μM of IBN-25 and 20 μM of IBN 32 and 0.045% DMSO as control for 72 h. Whole cell lysates were prepared on day 3 with lysis buffer [125 mM Tris (pH 7.4), 2% Sodium dodecyl sulfate, 10% glycerol, 6M urea and a protease inhibitor cocktail (Sigma) and 0.02% Bromophenol blue]. The lysates were sonicated for 30 seconds and then heated for 5 mins at boiling temperature. The lysates were centrifuged at 13000 rpm for 10 mins and the protein concentration of each sample was estimated using the BCA protein assay. The lysates was then mixed with 5% 2-mercaptoethanol and stored at −80 C. For Western blotting, samples containing 50 μg of total cell lysate were loaded onto a SDS-PAGE and subjected to electrophoresis. Proteins were transferred to a nitrocellulose membrane and then blocked with 5% non-fat dry milk in Tris buffer saline containing 0.1% Tween 20 for 60 min at 37 C. The membranes were probed with a primary antibody overnight at 4 C in TEST containing 5% Bovine serum albumin. Then the membrane was incubated with horseradish peroxidase (HRP)-conjugated anti-rabbit or anti-mouse secondary antibodies (GE Health care, Chalfont St Giles, UK). Detection was performed with enhanced chemiluminescence (ECL) reagent (Amersham Arlington Heights, Ill.) according to the manufacturer's protocol. Rabbit polyclonal Phospho-p53 (Ser15, 20, 46, 392), anti-caspase-9, anti-caspase-3, anti-PARP antibodies were purchased from Cell Signaling Technology, Inc. (Beverly, Mass., USA). Antibodies against p53 and p21 were purchased from Santa Cruz Biotechnology (Santa Cruz, Calif., USA). Equal loading of protein was demonstrated by probing the membranes with a mouse anti-β-actin monoclonal antibody (Sigma Chemical Co. (St. Louis, Mo.).

Immunostaining and Confocal Microscopy

For immunostaining, HLE cells were seeded at a density of $1\times10^4$ in 8 well chamber slide. After 24 h incubation, the cells were replaced with 200 μl fresh 10% DMEM medium and then treated with 60 μM of IBN-15, 90 μM of IBN-19, 90 μM of IBN-24, 30 μM of IBN-25 and 20 μM of IBN-32 and 0.045% DMSO as control for 24 and 48 h. After washing, cells were fixed in 4% formaldehyde for 15 mins and permeabilized with 0.5% Triton X-100 in PBS for 10 mins. The cells were then blocked for 60 min in PBS containing 3% bovine serum albumin and then incubated for 1 h with a mouse antibody against nucleolin (MS-3, Santa Cruz; 1:100 in blocking buffer). After washing extensively with PBS, the cells were then incubated for 1 h at room temperature in dark with a FITC-conjugated antibody against mouse IgG (1:20 ilution). The slides were mounted with a VectaShield medium containing DAPI (Vector Laboratories, Burlingame, Calif.). Microscopy was performed with a Zeiss LSM 510 Meta (upright stand) confocal microscope.

Real-Time Quantitative RT-PCR Analysis

Cells were seeded at a density of $4\times10^5$ cells per dish in 10 cm dishes. Next day, the cells were exposed to 90 uM of IBN-19, 90 uM of IBN-24, 40 uM of IBN-25 and 0.045% of DMSO (Dimethyl Sulphoxide) as the control. After 48 hrs, total RNAs were extracted from the cells using Nucleospin RNA II kit as per the manufacturer's istructions. RNA quality and yield were evaluated after spectrophotometer measurements.

The human apoptosis PCR array ($RT^2$ Profiler) was used to analyze mRNA levels of 84 key genes involved in apoptosis, in a 96-well format, according to the manufacturer's instructions (Super Array Bioscience). First-strand cDNA was synthesized with 1 μg of RNA by using a PCR array first strand-synthesis kit (C-03; Super array Bioscience). This kit uses reverse transcriptase (Power Script; Super array Bioscience) and a combination of random primers and oligo dT primers. The total volume of the reaction was 20 μL diluted to 100 μL. PCR reactions were performed using real-time PCR (79s00HT 96-well block with $RT^2$ Real-Time SYBR Green PCR master mix PA-012; Applied Biosystems Instruments 7500). The total volume of the PCR reaction was 25 μl. An equivalent of 1 μg of RNA was applied to the PCR reaction. The thermocycler parameters were 95° C. for 10 minutes, followed by 40 cycles of 95° C. for 15 seconds and 60° C. for 1 minute. Relative changes in gene expression were calculated using the $\Delta\Delta C_t$ (cycle threshold) method. An average of the number of cycles of the five housekeeping genes, GAPDH, Actin-β, β2m, Hprt1, and Rpl13d, was used to normalize the expression between samples. The expression data are presented as fold regulation. GAPDH gene expression levels were utilized as an internal control to normalize the data. Reported fold changes in expression are the ratios of treatment over control values.

Treatment of HCC Mice with Compound 9

Balb/c Nude mice, 5-6 weeks old, were inoculated with $1\times10^7$ Huh7 cells in 0.2 ml volume of Matrigel/DMEM mix. Since not every mouse developed a tumor after the inoculation of HCC cells, only those with visible tumors (about 8 weeks after inoculation) were used for subsequent experiment. The tumor-bearing mice were randomly divided to the control and the treatment group (n=3), respectively. Mice in the treatment group had free access to drinking water containing compound 9 (IBN-9) at 0.6 g/l or 1.5 g/l only, while mice in the control group had free access to water only. The compound treatment lasted for 3 weeks. The tumor size was measured weekly, and the tumor volume was calculated using the formula: $0.52\times width^2 \times length$.

Statistical Analysis

All data are presented as mean±SD. Significant differences between the groups Were determined using the unpaired Student's t-test. Levels of significance were defined as follows: $p<0.05$ (*), $p<0.01$ () and $p<0.001$ (*).

Results

Anti-Oxidative, Anti-Inflammatory and Anti-Fibrotic Properties of IMSs

Determination of Toxicity of IMSs on Cultured HSC T6 Cells and FVB Mice

Firstly we assessed the cytotoxicity of DBZIM and TDBZIM on cultured HSC-T6 cells using a 3-(4,5-dimethylthiazol-2-yl)-5-(3-carboxymethoxyphenyl)-2-(4-sulfophenyl)-2H-tetrazolium (MTS) based proliferation assay kit (Promega, Wis., USA). FIGS. 1a and 1b show the effect of DBZIM (0-400 μM) and TDBZIM (0-200 μM) on the proliferation of T6 cells cultured in DMEM containing 10% of FBS. At high concentrations of 250-400 μM, DBZIM inhibited cell proliferation by 3.5-8.9% with statistical significance. At high concentrations of 125-200 μM, TDBZIM demonstrated a stronger inhibition of 13-19% as compared to the control.

In the preliminary toxicity studies, two forms of IMSs were selected for in vivo testing with FVB inbred mice. For DBZIM, the lethal dosage was 50 mg/kg and LD50 was estimated to be 30-40 mg/kg. For DPIM, the lethal dosage was 500 mg/kg and LD50 was ~300-400 mg/kg.

DBZIM and TDBZIM Attenuated Cellular ROS Level and Enhanced GSH/GSSG Ratio

To measure the cellular oxidative stress level of HSC T6 cells treated with IMSs, cells cultured with DBZIM (10, 50, 100 and 300 μM) or TDBZIM (10, 50 and 100 μM) for 48 h in full serum medium were assayed for ROS, GSH and GSSG. Cells treated with NAC (1 or 5 mM), and EGCG (25 μM) were included as references. IMSs treatment led to significantly attenuated cellular ROS level. As shown in FIG. 2a, ROS was suppressed by DBZIM in a dosage-dependent manner (by 25% at 50 μM ($P<0.005$) and by 34% at 300 μM ($P<0.0005$)). TDBZIM, which is comprised of a trimer of DBZIM, substantially suppressed cellular ROS level by 19% at 10 μM ($P<0.01$) and by 36% at 100 μM ($P<0.00001$) (FIG. 2b). In comparison, EGCG was able to attenuate ROS by 14% at 25 μM ($P<0.005$), whilst NAC did not show apparent inhibition on ROS level even at 1 mM.

The effect of the compounds on the level of an important endogenous antioxidant, GSH, was also investigated. As indicated in FIGS. 3a and 3b, the total cellular GSH amount was quantified including the reduced glutathione (GSH) and oxidized glutathione (GSSG). As shown in FIG. 3a, DBZIM attenuated the total GSH level by 7%, 12% ($P<0.005$) and 20% ($P<0.0001$) at 10, 50 and 100 μM, respectively. At a high dosage of 300 μM of DBZIM, slight enhancement by 8% was observed, but without statistical significance. NAC (5 mM) did not show any effect on the total GSH, while EGCG (25 μM) induced the total GSH synthesis by 19% ($P<0.01$), which was in agreement with an earlier report (Fu et al. 2006). In contrast to its monomer, TDBZIM did not alter the total cellular GSH level at 10-100 μM (FIG. 3b). GSH was oxidized to GSSG in the reaction to reduce $H_2O_2$ to $H_2O$. The amount of GSSG was also quantified as shown in FIGS. 3c and 3d. DBZIM depleted GSSG by 13% at 10 μM, 23% at 50 μM ($P<0.0005$), 35% at 1001 μM ($P<0.0001$) and 85% at 300 μM ($P<0.0001$). In contrast, EGCG reduced GSSG by 42% at 25 μM ($P<0.05$) and NAC had no effect on GSSG at 5 mM. TDBZIM also suppressed GSSG production by 12% at 10 μM ($P<0.05$), by 35% at 50 μM ($P<0.05$), and by 50% at 100 μM ($P<0.0001$). The GSH/GSSG ratio was enhanced by 8%, 15% ($P<0.001$) and 23% ($P<0.0001$) under the influence of DBZIM at 10, 50 and 100 μM, respectively (see FIG. 3e). At a high dosage of DBZIM (300 μM), the increase in GSH/GSSG ratio was more dramatic, reaching 7.4 fold of that of the control group. There was no change in the GSH/GSSG ratio for NAC at 5 mM, whereas a 2-fold increase in the GSH/GSSG ratio was observed for EGCG at 25 μM ($P<0.0001$). For TDBZIM, the GSH/GSSG ratio was enhanced by 14% at 10 μM, by 65% at 50 μM ($P<0.05$) and by 106% at 100 μM ($P<0.001$) (FIG. 3f). These results suggested that these two forms of IMSs significantly enhanced the GSH/GSSG ratio mainly through attenuating the production of GSSG from the oxidation of GSH, resulting in improved anti-oxidation.

DBZIM and TDBZIM Attenuated GPx and CAT Activities, and DBZIM Enhanced GST Activity.

To further investigate the anti-oxidant properties of the IMSs, the activities of anti-oxidant enzymes: GPx, CAT, SOD and GST were assayed. FIG. 4a shows that DBZIM attenuated the GPx activity by 10% at 10 µM (P<0.005) and by 10% at 50 µM (P<0.01), but enhanced the GPx activity by 15% at a high Concentration of 300 µM (P<0.005), with a slight biphasic pattern. For TDBZIM, GPx activity was suppressed by 18% at 10 µM (P<0.05), by 25% at 50 µM (P<0.01) and by 34% at 100 µM (P<0.005) (FIG. 4b). In comparison, EGCG attenuated the GPx activity by 53% (P<0.005) at 25 µM, while NAC did not show much effect at 5 mM (FIG. 4a).

A similar pattern was observed for DBZIM's effect on CAT activity. DBZIM was able to attenuate CAT activity by 19%, 16% and 12%, respectively at 10 µM, 50 µM and 100 µM, respectively (P<0.05) (FIG. 4c). When the concentration was increased to 300 µM, the attenuating effect decreased to 8% without statistical significance. TDBZIM inhibited the CAT activity by 25% at 10 µM (P<0.005), 31% at 50 µM (P<0.0005) and 20% at 100 µM (P<0.005), with a less potent effect above 50 µM (FIG. 4d). EGCG showed 13% suppression on CAT activity, but the data were not significant, whereas NAC demonstrated 35% inhibition (P<0.01) (FIG. 4c).

As shown in FIGS. 4e and 4f, DBZIM, TDBZIM, EGCG and NAC all did not show much effect on the SOD activity, suggesting that these compounds did not act on superoxides. FIG. 4g illustrates the GST activity of cells under the treatment of DBZIM (10-300 µM). GST activity was enhanced by 22% at 100 µM (P<0.005) and by 32% at 300 µM (P<0.0001). In contrast, EGCG and NAC did not have much affect on the GST activity.

DBZIM and TDBZIM Protected Primary HSCs from DMSO Cytotoxicity DMSO is a common solvent used in cell-based assays (at concentrations of ≤0.5% (v/v)) and cell cryopreservation (at a concentration of ~10% (v/v). For the primary HSCs, however, DMSO imposed significant toxicity at a concentration of 0.2% (v/v) (FIG. 5a). Control cells incubated with 0.2% (v/v) of DMSO died after 26 h. In contrast, the cells survived in the co-presence of 100 µM of DBZIM or 50 µM of TDBZIM and 0.2% (v/v) of DMSO. When they were cultivated for over 93 h, the cells remained viable and proliferated to confluency in the presence of TDBZIM. However, most cells died in the presence of DBZIM after 93 h. This suggested that TDBZIM provided a more potent protective effect against DMSO's toxicity on primary HSCs.

Figure 5G:
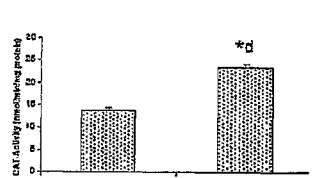
Figure 5:
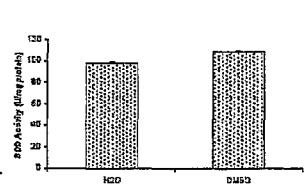

DMSO-induced oxidative stress in cultured HSC T6 cells was quantitatively characterized by the depleted total cellular GSH level (74% of the control, P<0.0001), the dramatically increased GSSG amount (4.4 fold of the control, P<0.0001), the decreased GSH/GSSG ratio (17% of the control, P<0.001), the induced GPx (2.62 times of the control, P<0.0001) and CAT (1.7 fold of the control, P<0.0001) antioxidant enzymes (see FIGS. 5b,c,d,e,f). DMSO also enhanced SOD activity slightly (10% increase), but the data were not statistically significant (FIG. 5g). This finding suggested that the protective effect of IMSs against DMSO cytotoxicty on primary HSCs was through the attenuation of oxidative stress. A similar observation was reported in another study that found that quercetin, a flavonoid (0.1 µM), can effectively protect human lens epithelial cells from dying from 1% (v/v) of DMSO, presumably through the attenuation of oxidative stress (Cao et al. 2007).

Figure 6:
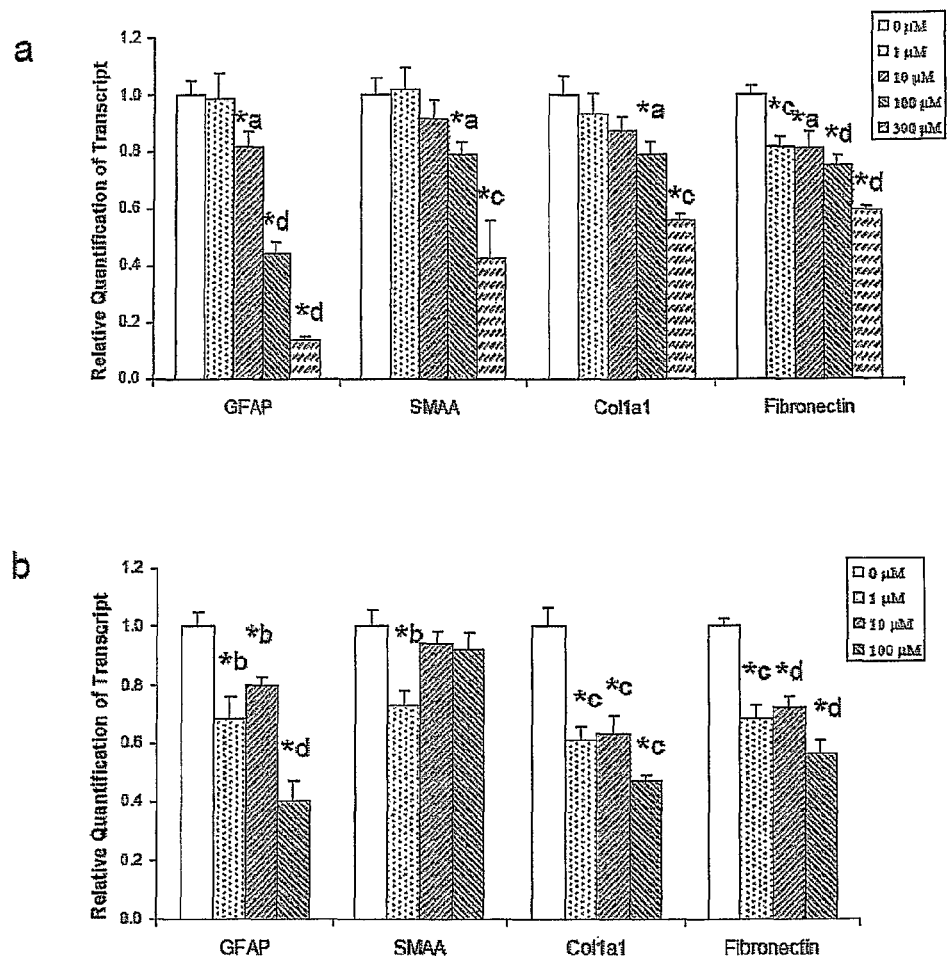
FIG. 6. (a) DBZIM and (b) TDBZIM suppressed the mRNA expression of HSC activation markers (GFAP and SMAA) and fibrotic endpoints (col1a1 and fibronectin) in a dosage-dependent manner. HSC T6 cells were treated with DBZIM (1, 10, 100 and 300 μM) and TDBZIM (1, 10 and 100 μM) for 48 h. β-actin was used as the normalization gene; its expression level was constant under the experimental conditions. The ΔΔCt method was used for relative quantification with vehicle control sample being the calibrator. The data were presented as mean and SEM, N=6, *$^a$P<0.05, *$^b$P<0.01, *$^c$P<0.005, and *$^d$P<0.0005, when compared to the vehicle control.

IMSs Suppressed HSC Activation Markers and Fibrogenic Endpoints in a Time- and Dosage-Dependent Manner It has earlier been shown that GFAP can be used as a biomarker along with SMAA for HSC activation in vitro (Zhang et. al 2006). Deposition of ECM (including collagen and fibronectin) was the endpoint used to assess the degree of fibrosis. Two IMSs (DBZIM and TDBZIM) suppressed the mRNA level of both HSC activation markers (GFAP and SMAA) and fibrotic endpoint (col1a1 and fibronectin) in a dosage-dependent (FIGS. 6a and 6b) and time-dependent (FIGS. 7a-d) manner. As shown in FIG. 6a, DBZIM attenuated GFAP mRNA expression levels by 18% (P<0.05) and 86% (P<0.001) at 10 µM and 300 µM, respectively. It attenuated SMAA by 21% at 100 µM (P<0.05) and by 58% at 300 µM (P<0.001), col1a1 by 21% at 100 µM (P<0.05) and by 44% at 300 µM (P<0.001), and fibronectin by 19% (P<0.005) to 40% (P<0.0001) with dosages of 1 µM to 300 µM.

The dosage dependency of TDBZIM was less prominent compared to its monomer counterpart (FIG. 6b). TDBZIM decreased GFAP mRNA by 32% at 1 µM (P<0.01), by 20% at 10 µM (P<0.01) and by 60% at 100 µM (P<0.0001), SMAA by 27% only at a low dosage of 1 µM (P<0.01), col1a1 by 39% at 1 µM (P<0.005), by 36% at 10 µM (P<0.005) and by 53% at 100 µM (P<0.001), and fibronectin by 32% at 1 µM (P<0.0010), by 28% at 10 µM (P<6.0005) and by 43% at 100 µM (P<0.0001).

Figure 8:
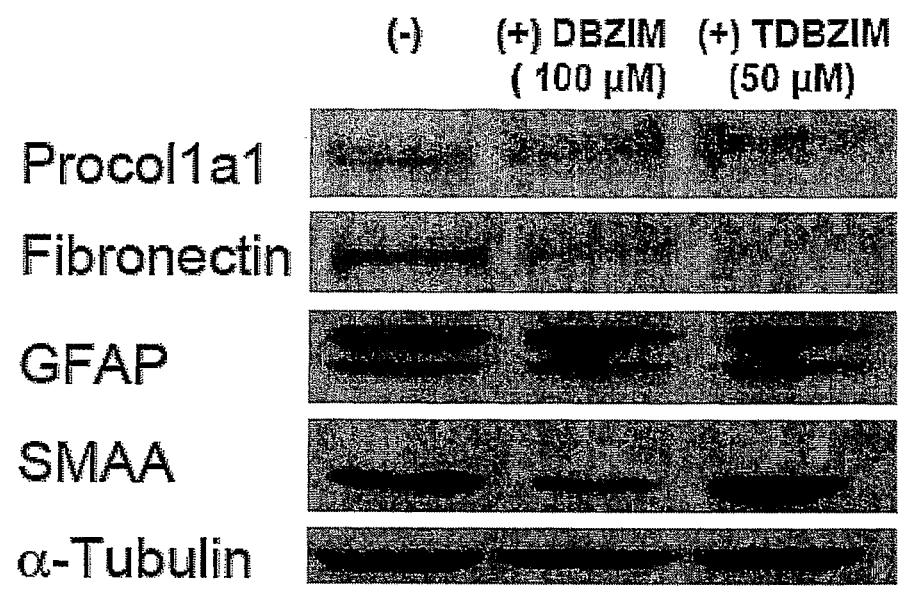
FIG. 8. Western blotting of col1a1, fibronectin, GFAP and SMAA protein expression in HSC T6 cells treated with DBZIM (100 μM) and TDBZIM (50 μM) for 48 h. 15 μg of total proteins were resolved in 3-8% of tris-acetate gel for col1a1 and fibronectin, or 4-12% gradient PAGE-SDS gel for GFAP and SMAA. The target proteins were recognized by the respective antibodies, and visualized by the ECL method. The membrane was stripped and re-probed for α-tubulin as the loading control.

Time course study showed that 100 µM of DBZIM and TDBZIM, respectively, suppressed GFAP by 28% (P<0.05) and 30% (P<0.05) at 8 h, by 40% (P<0.005) and 36% (P<0.005) at 24 h, and by 56% (P<0.0001) and 60% (P<0.0001) at 48 h. They suppressed col1a1 by 22% and 22% (P<0.01) at 8 h, by 29% (P<0.005) and 40% (P<0.0001) at 24 h, and by 21% (P<0.05) and 53% (P<0.001) at 48 h. They also suppressed fibronectin by 15% (P<0.05) and 25% (P<0.05) at 8 h, by 17% (P<0.05) and 29% (P<0.05) at 24 h, and by 25% (P<0.0005) and 43% (P<0.0001) at 48 h. It was generally true that the IMSs suppressed almost all HSC activation markers and endpoint molecules in a time- and dosage-dependent manner, except that SMAA was transiently induced by up to 79% by 100 µM of TDBZIM at 24 h, while no change was observed with both compounds at 8 h, and 21% suppression was noted for DBZIM (P<0.05) at 48 h. SMAA expression was particularly induced by TDBZIM at a high dosage. Western blotting of GFAP, SMAA, col1a1 and fibronectin was also performed to evaluate the influence of compounds on the protein expression level. As shown in FIG. 8, both DBZIM (100 µM) and TDBZIM (50 µM) attenuated procollagen αI(I) and fibronectin significantly, and GFAP expression to a less degree, when the cells were treated for 48 h. DBZIM suppressed SMAA protein, but TDBZIM enhanced SMAA, which agreed with the real-time PCR data. Other time points (8 h and 24 h) were also examined, but no significant change was observed (data were not shown).

IMSs Suppressed Transcription of TGF-β1 and TGF β RI

TGF-β1 is the most important pro-fibrogenic cytokine. When the liver is insulted, quiescent HSCs respond to TGF-β1 secreted by Kupffer cells and endothelial cells, and start to produce TGF-β1 themselves via autocrine loops. TGF-β1 is over-expressed during HSC activation and liver fibrogenesis (Bachem et al. 1992). The total TGF-β1 synthesis under the treatment of IMSs was measured. As shown in FIG. 9a, DBZIM suppressed the TGF-β1 mRNA by 28% (P<0.05) and 33% (P<0.005) at high concentrations of 100 µM and 300 µM, respectively. TDBZIM inhibited TGF-β1 by ~23% regardless of dosage (1-100 µM) with statistical significance (P<0.05) (FIG. 9b). For 8-24 h treatment, both DBZIM and TDBZIM suppressed TGF-β1 transcription by 40-50% (P<0.05) (FIG. 9c). The less apparent dosage- or time-dependency might be due to the auto-looping characteristic of TGF-β1.

DBZIM and TDBZIM Inhibited Pro-Inflammatory and Pro-Fibrogenic Cytokine IL-6

IL-6 is regulated by NF-κB and involved in inflammatory responses. Being a pro-contractile and pro-inflammatory cytokine, IL-6 plays an important role in liver fibrogenesis. To study the influence of IMSs on IL-6, IL-6 mRNA expression was quantified using real-time PCR. As shown in FIG. 10a, DBZIM inhibited IL-6 transcription in a dosage-dependent manner by 37% at 1 µM ($P<0.0005$), by 46% at 10 µM ($P<0.0005$), by 53% at 100 µM ($P<0.0001$), and by 59% at 300 µM ($P<0.0001$). TDBZIM demonstrated more potent inhibition of 37% at 1 µM ($P<0.01$), 55% at 10 µM ($P<0.0001$) and 80% at 100 µM ($P<0.0001$) (FIG. 10b). Time course study showed that 100 µM of DBZIM significantly suppressed IL-6 mRNA expression by 53% at 48 h ($P<0.005$). Shorter treatment of DBZIM did not show statistically significant suppression on IL-6. 100 µM of TDBZIM demonstrated an inhibitory effect of 52% at 24 h ($P<0.005$), and 80% at 48 h ($P<0.0001$) (FIG. 10c).

DBZIM and TDBZIM Mediated Through NF-κB and AP-1 Transcription Factors

Figure 11:
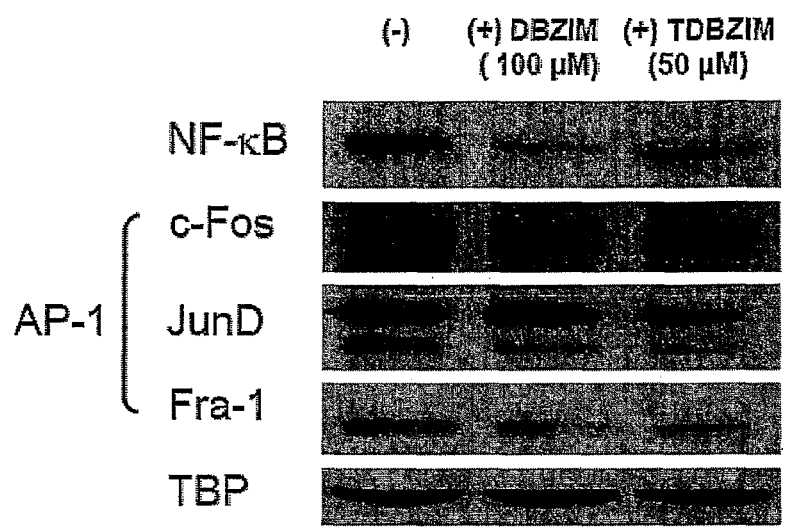
FIG. 11. Western blotting of NF-κB and AP-1 (c-Fos, JunD and Fra-1) protein expressions in HSC T6 cells treated with DBZIM (100 μM) and TDBZIM (50 μM) for 48 h. 15 μg of nuclear protein was resolved in 4-12% gradient PAGE-SDS gel. The target proteins were recognized by the respective antibodies, and visualized by the ECL method. The membrane was stripped and probed for the Tata binding protein TBP used as the loading control.

Transcription factors NF-κB and AP-1 are known to be sensitive to cellular redox states. NF-κB also plays an essential role in physiological conditions such as inflammation and tissue repair. Protein expression of the NF-κB P65 and activation protein 1 (AP-1) family members (c-Fos, c-Jun, Jun B/D, Fra-1/2) were examined when the cells were treated with IMSs. As shown in FIG. 11, nuclear NF-κB P65 in an active form was significantly attenuated by both DBZIM and TDBZIM. The amount of latent NF-κB in cytosol was not affected (data not shown). AP-1, c-Fos, Jun D and Fra-1 were suppressed, while c-Jun, Jun B and Fra-2 were less affected.

IMSs Regulated the Expression of a HSC-Specific GFAP-Reporter Surrogate

It has been shown earlier that the GFAP-lacZ transgene reporter could be used to screen anti-fibrotic compounds (Maubach et. al 2006, Zhang et. al 2006). In the current experiment, the β-galactosidase activity under the treatment of DBZIM and TDBZIM at different dosages (0-300 µM) and time points (24 h and 48 h) was assayed. Significant suppression on β-galactosidase activity was observed for DBZIM: by 25% at 100 µM ($P<0.001$) and by 34% at 300 µM ($P<0.001$) (FIG. 12a). For TDBZIM, a smaller and transient suppression (20%) was observed at 100 µM at 24 h (FIG. 12b).

Safety and Efficacy of Additional IMSs with Different Substituents

IMSs of different structures were also tested in a preliminary structure-activity-relationship (SAR) study. Testing was performed on 3-Bisbenzylimidazolium bromide (DBZIM), 1,3,5-tris(4-methyl-imidazolium)-linked cyclophane.3Br (TDBZIM), 1,3-Diisopropylimidazolium tetrafluoroborate (DPIM), 1,3-Di-tert-butylimidazoliniumtetrafluoroborate (DBIM), 1,3-Bis(1-adamantyl)imidazolium tetrafluoroborate (AMIM), 1,3-Bis(2,4,6-trimethylphenyl)-imidazolinium chloride (TMPHIM), 1,3-Bis(2,6-diisopropyl-phenyl)-imidazolinium chloride (DPPHIM) and 1,3-Bisbenzyl-benzimida-zolium bromide (DBZBIM). In general, those with smaller aliphatic groups, such as 1,3-diisopropylimidazolinium tetrafluoroborate (DPIM) and 1,3-di-tert-butylimidazolium tetrafluoroborate (DBIM), showed less toxicity on T6 cells, compared to those with bulky aromatic groups, such as 1,3-bis(2,4,6-trimethylphenyl)imidazolium chloride (TMPHIM) and 1,3-bis(2,6-diisopropylphenyl)imidazolium chloride (DPPHIM). Those with a methyl spacer between the imidazolium and aromatic ring, such as 1,3-bisbenzylimidazolium bromide (DBZIM) and 1,3-bisbenzylbenzimidazolium bromide (DBZBIM), showed moderate toxicity. The toxicity of compounds was ranked based on IC50 as follows: DPIM (IC50=3.1 mM)<DBIM (IC50 was undetermined due to limited solubility in DMSO, but estimated to be 2-3 mM)<DBZIM (IC50=1.7 mM)<TDBZIM (IC50~500 µM)<DBZBIM (IC50=310 µM)<AMIM (IC50=166 µM)<TMPHIM (IC50=110 µM)<DPPHIM (IC50=34 µM).

Efficacy of compounds in suppressing fibrosis was also evaluated. HSC T6 cells were treated with IMSs at concentrations that were below their respective IC50. Compounds were either dissolved in DMSO or $H_2O$ depending on their solubility, and the intensities of the bands were compared to the respective control. As shown in FIG. 13A, proteins of SMAA, Col1a1, fibronectin, TGF-β1 and TGFβ RI were all suppressed with the treatment of IMSs. Semiquantitative data from measuring the gray scale of the band pixels is summarized in FIG. 13B. If all 5 parameters are assigned with equal importance, the efficacy of IMSs could be roughly ranked as DPIM>TMPHIM>AMIM>DBIM>DBZBIM>DBZIM>DPPHIM>TDBZIM.

GFAP, SMAA, fibronectin and col1a1 transcripts were also quantified by real-time PCR. As shown in FIGS. 14a,b,c,d, GFAP mRNA was suppressed by 2 mM of DPIM by 78% ($P<0.0001$), by 50 µM of AMIM by 69% ($P<0.0005$), by 50 µM of TMPHIM by 66% ($P<0.001$), and by 100 µM of DBZBIM by 50% ($P<0.005$). SMAA mRNA was suppressed by 1 mM of DBIM by 49% ($P<0.05$), by 2 mM of DPIM by 78% ($P<0.0001$), by 50 µM of AMIM by 23% ($P<0.05$), and by 50 µM of TMPHIM by 49% ($P<0.05$). Fibronectin mRNA was suppressed by DPIM by 48% ($P<0.05$), by TMPHIM by 29% ($P<0.005$), and by DBZIM by 26% ($P<0.005$). Col1a1 mRNA was suppressed by DBIM by 58% ($P<0.0005$), by DPIM by 61% ($P<0.0001$), by TMPHIM by 62% ($P<0.0001$), and by DPPHIM by 47% ($P<0.05$). EGCG did not show significant inhibition on HSC activation and fibrosis. This might due to the chemical instability of EGCG under the prolonged incubation of 48 h. It was reported that the half life of EGCG was only. 30 min in the culture medium for human esophageal cancer cells (Hou et al. 2005) and ~72 min in rat blood at a dosage of 30 mg/kg (Lin et al. 2004). Among all the IMSs, DPIM and TMPHIM showed significant suppression on all four genes, and DPIM was the most potent agent under the test conditions.

Effect IMSs on Liver Fibrosis in Mice

Figure 15:
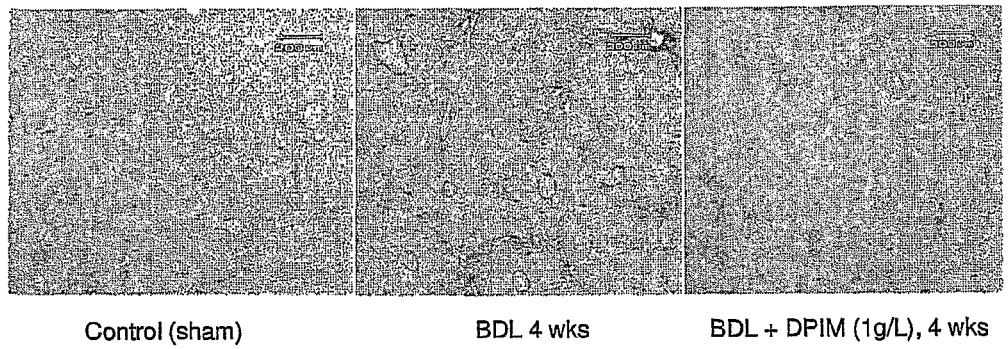
FIG. 15 Effect of DBZIM and DPIM on liver fibrosis in mice. DBZIM was tested on mice induced by (a) liver toxin thioacetamide (TAA) or by (b) bile duct ligation (BDL). DPIM was also tested on mice induced by TAA (data not shown)) or by (c) bile duct ligation (BDL). DBZIM attenuated fibrosis in the TAA model (at 500 mg/L, 12 weeks) and the BDL model (at 10 mg/L, 4 weeks), whereas the DPIM displayed its effect in the BDL model at 1 g/L (4 wks).

DBZIM and DPIM were tested in two liver fibrosis models in mice induced by liver toxin thioacetamide (TAA) or by a surgical procedure called bile duct ligation (BDL), respectively. As shown in FIG. 15, the two IMSs, when administered in drinking water, showed anti-fibrotic properties in the two mouse models of liver fibrosis. Particularly DBZIM attenuated fibrosis in the TAA model (at 500 mg/L, 12 weeks) (FIG. 15a) and the BDL model (at 10 mg/L, 4 weeks) (FIG. 15b), whereas the DPIM displayed its effect in the BDL model at 1 g/L (4 wks) (FIG. 15c). This data suggests that IMSs have potential as anti-liver fibrosis therapeutic compounds.

DPIM Attenuated Liver Fibrosis

Figure 16:
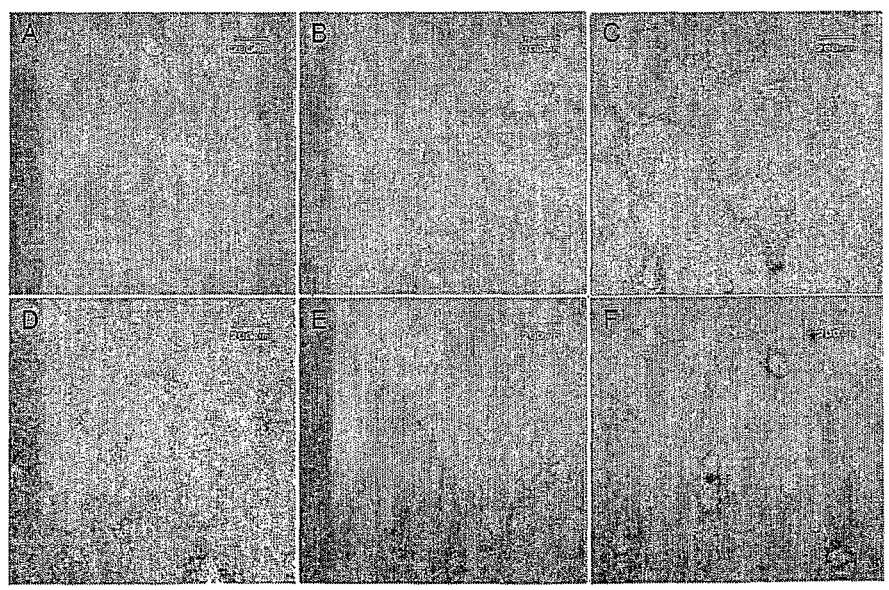
FIG. 16. Representative of images of Sirius red staining in liver sections from different DPIM compound treated group mice. Each treated group had 6-8 mice, except for 500 mg/l treated group, which had only one mouse in the group. Red staining areas represent collagen deposits. (A) sham operated, (B) sham operated+DPIM 1 g/l for 4 weeks, (C) BDL for 4 weeks, (D) BDL 4 weeks+500 mg/l DPIM treatment, (E) BDL 4 weeks+750 mg/l DPIM treatment, and (F) BDL 4 weeks+1 g/l DPIM treatment.
Figure 17:
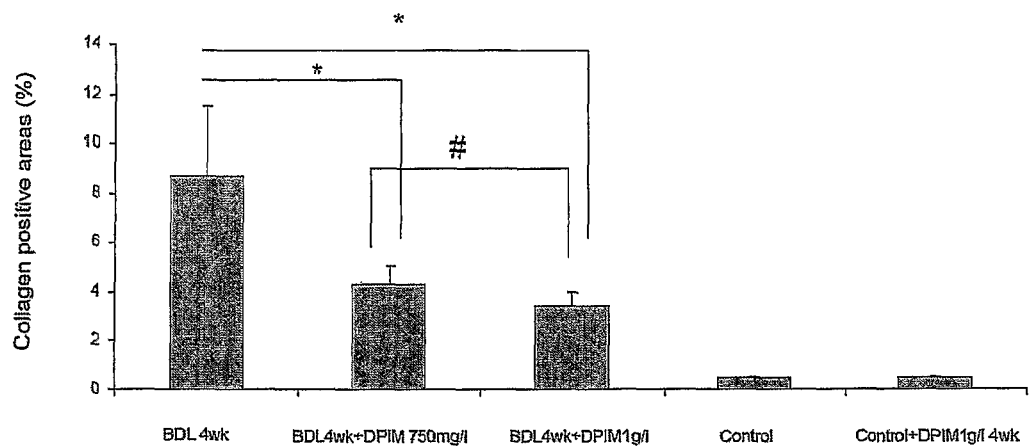
FIG. 17. Percentage of Sirius red staining areas. Sirius red staining areas from different treatment group mice were quantified with Image J software, at least 6 different areas from left and middle lobes of liver of each mouse were covered. *P<0.05, BDL vs. DPIM treated groups; # P<0.05, 750 mg/l vs. 1 g/l treated groups.

DPIM was chosen for further in vivo study, To ensure proficiency in BDL procedure, a number of exercises and tests were performed to eventually achieve over 90% success rate on the BDL surgery and over 4 weeks of survival time for the operated mice. The extent of fibrosis was assessed by the Sirius-Red collagen staining at 4 weeks post-BDL. An extensive collagen accumulation around the sinusoidal areas was observed in the BDL group (FIG. 16C), whereas only minimal collagen staining was seen in the sham operated group (FIG. 16A). Treatment of sham mice with 1 g/l of DPIM for 4 weeks did not induce any significant build-up of collagen (FIG. 16B). Four weeks after compound treatment, the collagen contents were dramatically reduced by 750 mg/l (FIG. 16E) and 1 g/l (FIG. 16F) of DPIM. The effect by the 500 mg/l of DPIM was not conclusive, since only one mouse was treated with this dose at the time of data collection (FIG. 16D). Quantitatively the Sirius-Red positive areas were reduced from 8.69 to 4.33 by the dose of 750 mg/l, and even more (and dose-dependently) down to 3.42 by the dose of 1 g/l (FIG. 17).

DPIM Reduced Fibrotic Cellular Proliferation

Figure 18:
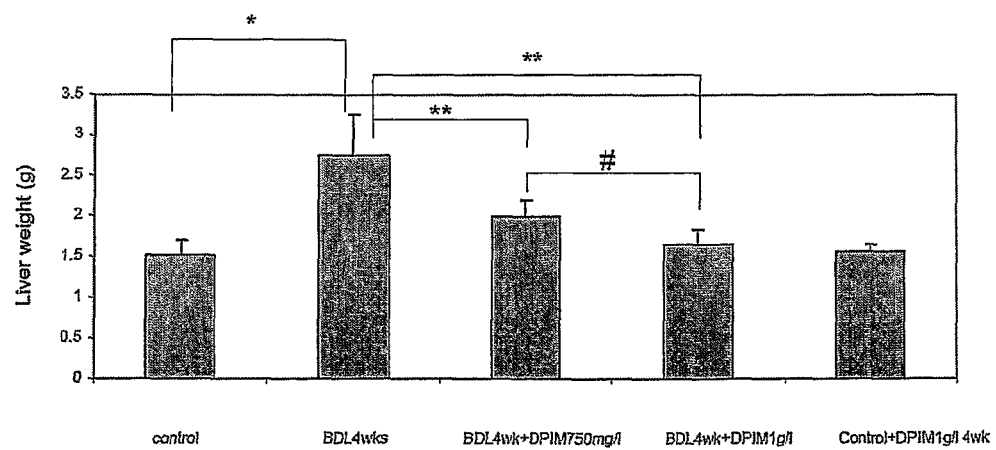
FIG. 18. Liver weights of different treatment groups. Each group consisted of 6-8 mice which were 10-12 weeks old at the start of surgery procedure. *P<0.05, sham operated control group vs: BDL 4 weeks, **P<0.05, DPIM compound treated groups vs; BDL weeks group, # P<0.05, 750 mg/l DPIM treated group vs. 1 g/l DPIM treated group.

Liver weight increases in BDL-mice mainly due to 1) the build-up of bile, and 2) fibrotic cellular proliferation. The livers of different treated groups were weighed, 4 weeks after BDL, liver weight was increased by 83% compared with sham operated mice (1.50±0.19 g for sham operated, vs. 2.74±0.51 g for BDL 4 weeks, P<0.05). However, DPIM compound treatments showed a significant liver weight reduction (P<0.05, DPIM compound treatment vs. BDL 4 weeks): 1.97±0.44 g for the 750 mg/l treatment group, 1.65±0.20 g for the 1 g/l treatment group (FIG. 18). This dose-dependant effect was consistent with Sirius red staining areas. Compared with sham operated mice, DPIM treatments in sham operated mice for 4 weeks did not result in significant liver weight change (1.56±0.08 g for DPIM treated vs. 1.50±0.19 g for sham operated, P=0.46)(FIG. 18).

Figure 19:
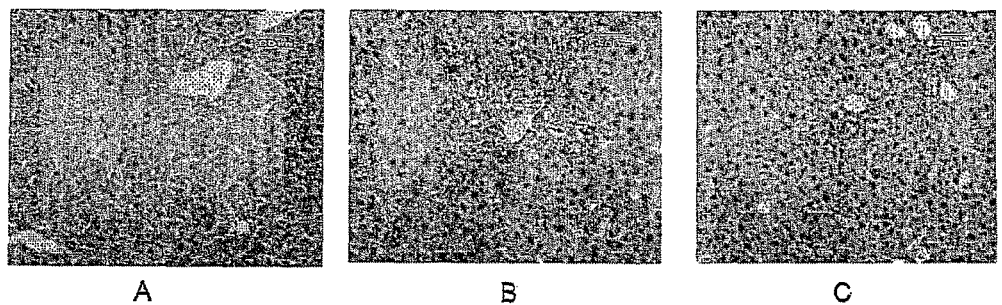
FIG. 19. Representative images of H&E staining of liver sections. (A) control group; (B) BDL 4 weeks group; and (C) BDL 4 weeks+DPIM 1 g/l treatment group.
Figure 20:
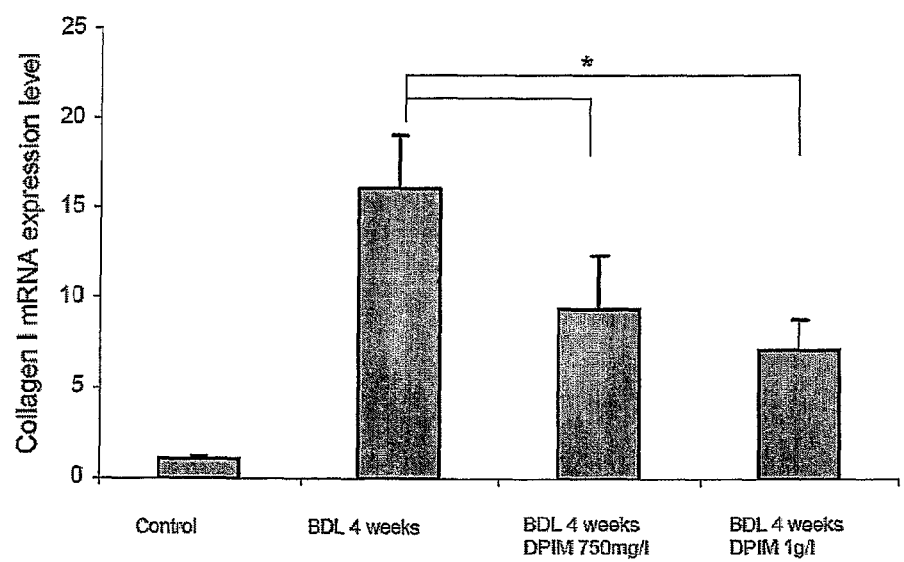
FIG. 20. Quantitative real-time PCR for collagen 1a1 mRNA. DPIM reduced collagen 1a1 mRNA.

H&E staining of the liver sections (FIG. 19) showed that DPIM treatment (FIG. 19C) reduced the number of proliferative cells (identified by the nuclear staining of Hamehexlin) around the sinusoidal area, when compared to the DBL group (FIG. 19B) and control sham group (FIG. 19A). At the messenger level, DPIM also reduced the collagen 1a1 mRNA (FIG. 20).

Effect of DBZIM on Hepatocellular Carcinoma and Other Tumour Cells

DBZIM Inhibited Cell Proliferation and Disrupted Cell Cycle in HLE Cells

The effect of DBZIM on the HCC cell proliferation and cell cycle was characterized on a high-content screening (HCS) platform. Under each concentration, at lease 1000 cells were analyzed. 5-bromo-2'-deoxyuridine (BrdU), which incorporates into replicating DNA, is used to identify cells which have progressed through S phase of cell cycle. DAPI staining was used for nuclear identification and DNA content determination. DBZIM inhibited the HLE cell proliferation as indicated by less total cell number and less BrdU positive cells in a dose-dependant manner (FIG. 21A), and arrested HLE cells in the G0/G1 phase (FIG. 21B).

DBZIM Induced Cell Death through Apoptosis in HCC Cells

Cell-based caspase 3/7 activity and lactate dehydrogenase (LDH) release assay allow the differentiation of apoptosis and necrosis of cells under the influence of DBZIM. As shown in FIG. 22A-D, caspase 3/7 activity (indicative of apoptosis) in both HLE and HepG2 cells was enhanced by DBZIM, while LDH release (indicative of cytotoxicity) was least affected under the same treatment regimen. It suggested that DBZIM used at the current treatment condition caused the HCC cell death mainly by apoptosis, rather than necrosis.

Apoptosis was further confirmed by annexin V staining. In the initial phase of apoptosis, cells translocated the membrane phosphatidylserine (PS) from the inner face of the plasma membrane to the cell surface. The surface PS is readily detected by fluorescent conjugate of annexin V, which has a high affinity for PS and often used as an apoptosis marker. As shown in the scatter plots in FIG. 22E-F, DBZIM dose-dependently induced apoptosis in both HepG2 and HLE cells. It was noted that as a positive control, the TRAIL (TNF-Related Apoptosis Inducing Ligand) only induced apoptosis in HepG2, but not in HLE cells.

DBZIM Triggered Mitochondria-Mediated Apoptosis Pathway

In order to understand the apoptosis pathway involved by DBZIM, caspase 3, 8, 9 activities were assayed using colorimetric assays. As shown in FIG. 23A, caspase 8 activity was not affected by DBZIM, whilst caspase 9 and 3 activities were dose-dependently enhanced by DBZIM, pointing a mitochondria-mediated apoptosis pathway. However, DBZIM was found to cause a minimal release of cytochrome C from the mitochondria to the cytosol (FIG. 23B).

Figure 24:
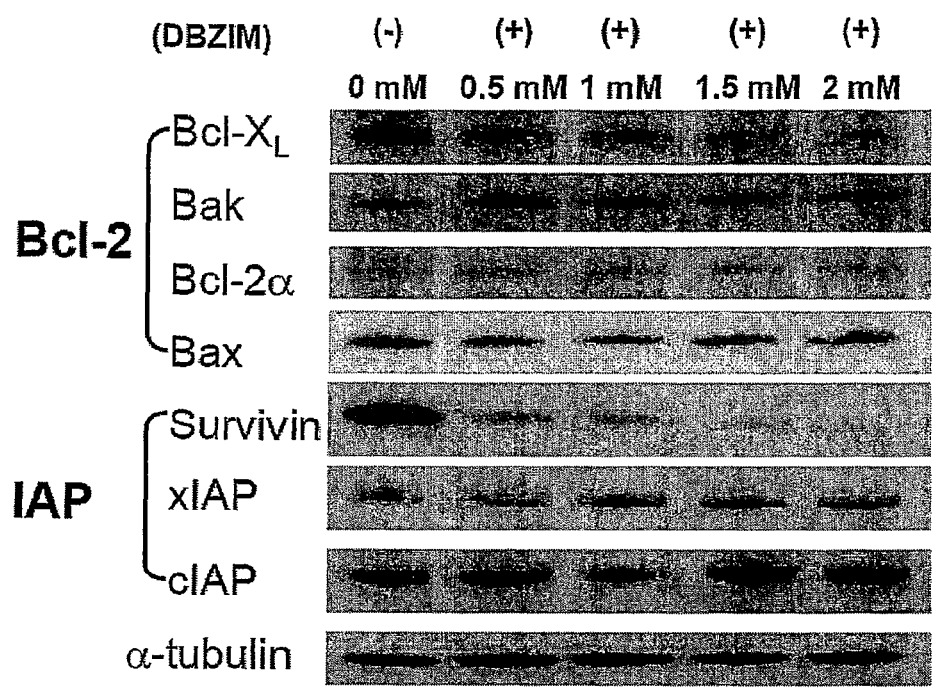
FIG. 24. DBZIM affected Bcl-2 and IAP protein expression. HepG2 cells were treated with DBZIM (0, 0.5, 1.0, 1.5 and 2.0 mM) for 24 hr. Total protein was collected using RIPA buffer. 15 µg of total protein was resolved in 4-12% gradient PAGE-SDS gel. The target proteins were recognized by respective antibodies, and visualized by the ECL method. The membrane was stripped and probed for the α-tubulin as the loading control.
Figure 25:
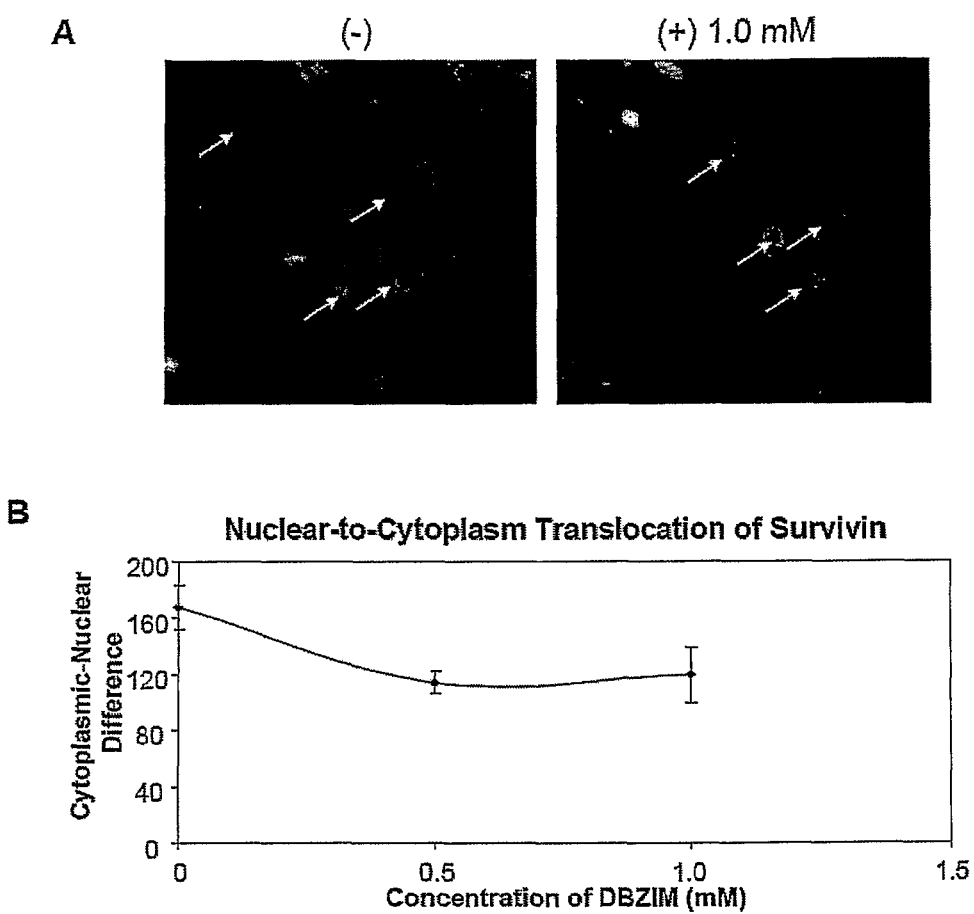
FIG. 25. DBZIM induced nucleus to cytoplasm translocation of survivin protein. (A) Representative immunocytostaining images of HLE cells treated by DBZIM (0 and 1.0 mM) for 24 hr. Arrows indicate the accumulation and the disappearance of survivin in the nucleus of the control and the DBZIM-treated cells, respectively. The images were acquired and analyzed using ArrayScan VTI HCS reader (Thermal Scientific, PA, USA) and Target Activation BioApplication software. (B) Quantitation of translocation event. Cells were grown in 96-well plate and treated by DBZIM of various concentrations for 24 hr before fixation and immunocytostaining for survivin. Lower value in "Cytoplasmic-Nuclear Difference" indicated a lower amount of cytoplasmic survivin.

The mitochondria-mediated intrinsic apoptosis pathway is mainly regulated by the Bcl-2 and the IAP (Inhibitor of Apoptosis Protein) families. As shown with Western blotting in FIG. 24, the anti-apoptotic protein $Bcl-X_L$ and the pro-apoptotic protein Bak were slightly down-regulated and up-regulated by DBZIM respectively, whereas the other two members of the Bcl-2 family, Bcl-2α and Bax, were not affected by the treatment. Notably in the IAP family, survivin was significantly suppressed by DBZIM, whereas xIAP and cIAP were not affected (FIG. 24). In addition, HCS analysis revealed that survivin was translocated from the nucleus to the cytoplasm under the influence of DBZIM (FIG. 25).

DBZIM Induced Cytoplasm-To-Nucleus Translocation of AIF

Figure 26:
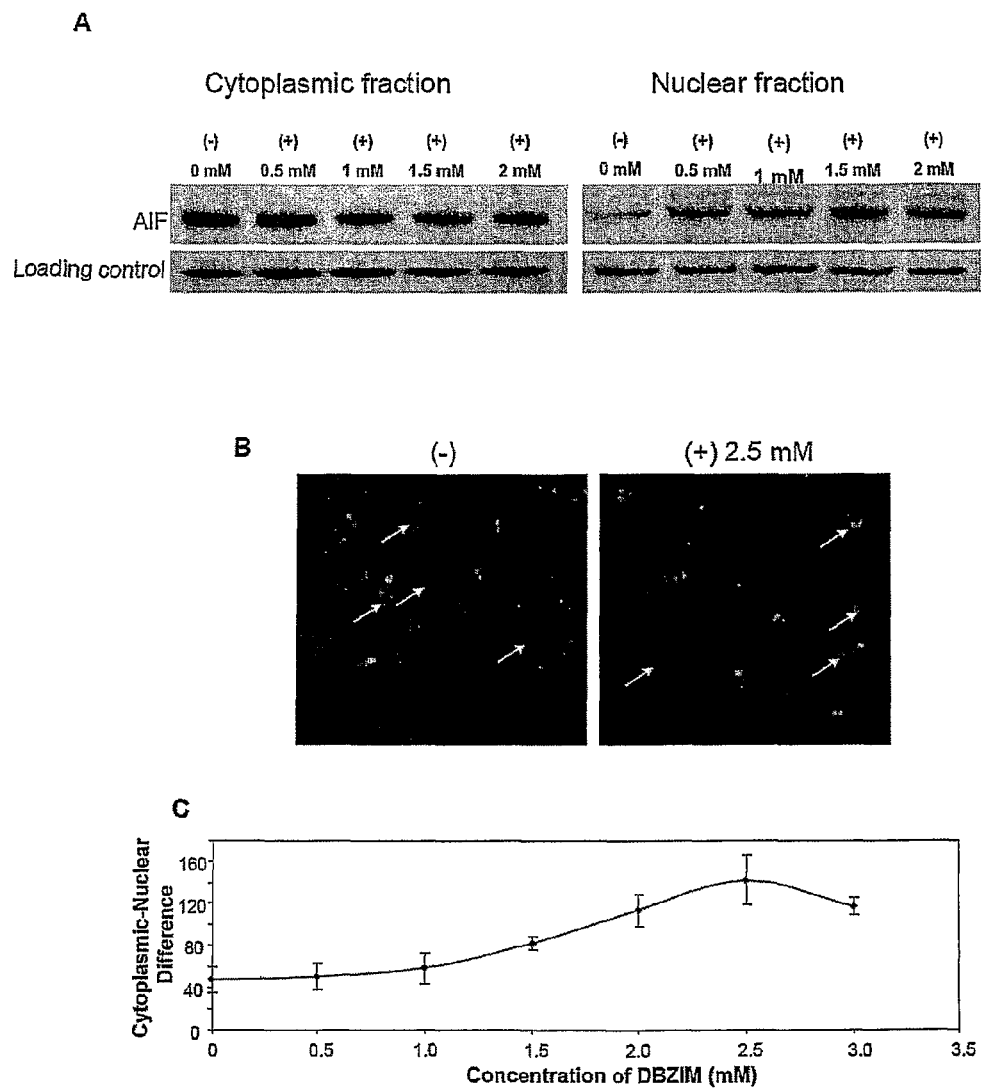
FIG. 26. DBZIM induced cytoplasm-to-nucleus translocation of AIF. (A). DBZIM translocated AIF from cytoplasm to nucleus. HepG2 cells were treated by DBZIM for 24 hr. Cytoplasmic and nuclear proteins were fractionated using a kit from Pierce. 15 µg of proteins were resolved in 4-12% gradient PAGE-SDS gel. The target proteins were recognized by the antibody of AIF, and visualized by the ECL method. The membrane was stripped and re-probed for α-tubulin as the loading control for cytoplasmic fraction and Tata binding protein TBP for nuclear protein. (B). HLE cells were grown in 96-well plate and treated by DBZIM for 24 hr. The cells were then fixed and stained by antibody of AIF. The images were acquired and analyzed using ArrayScan VTI HCS reader (Thermal Scientific, PA, USA) and Target Activation BioApplication software. The arrows indicate the cytoplasmic and the nuclear location of the AIF staining in the control and the DBZIM, respectively. (C). Quantification of AIF staining in different subcellular compartments. Higher value in "Cytoplasmic-Nuclear Difference" indicated higher nuclear AIF.

Apoptosis-inducing factor (AIF) is normally localized in the mitochondria, and translocated to the nucleus upon induction of apoptosis. It induces mitochondria to release caspase 9. In nucleus, AIF also induces chromatin condensation and DNA fragmentation, a process known as caspase independent apoptosis pathway. DBZIM was found to induce the translocation of AIF to the nucleus by Western blotting (FIG. 26A). Immunocytostaining showed that AIF was translocated from the mitochondria/cytoplasm to the nucleus (FIG. 26B). It is worth noting that under DBZIM treatment the nuclear AIF (arrows) tends to be associated with the smaller condensed nuclei which are presumably going through the apoptosis. Quantitative analysis with HCS suggested that the DBZIM-induced translocation is dose-dependent (FIG. 26C).

DBZIM Induced Apoptosis through Inducing ROS and AP-1

Figure 27:
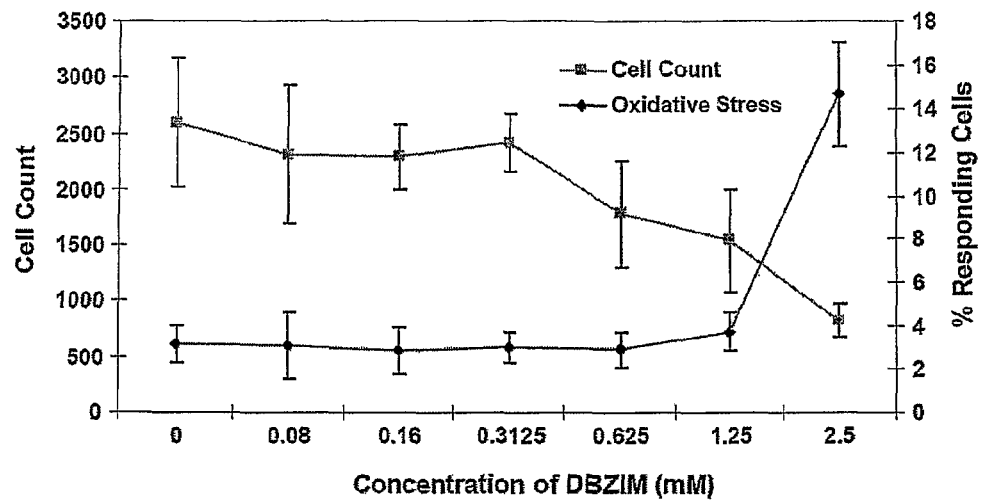
FIG. 27. High dose DBZIM induced ROS production in HLE cells. HLE cells were grown in 96-Well plate and treated by DBZIM for 24 hr. The cells were then fixed and stained by DHE for quantification of ROS generation. The images ware acquired and analyzed using ArrayScan VTI HCS reader (Thermal Scientific, PA, USA) and Target Activation BioApplication software.

Reactive oxygen species (ROS) not only directly modifies cellular macromolecules, it also actively participates in various cellular signaling. An elevated level of ROS has been reported to trigger the programmed cell death by apoptosis. When treated with DBZIM at the millimolar range, HLE cells generated significant amount of ROS and coincidentally underwent mass cell death (FIG. 27).

A sustained and elevated level of transcription factor activation protein 1 (AP-1) complex is known to participate in apoptosis. Western blotting (FIG. 28) of nuclear extracts from HLE cells showed that DBZIM significantly induced several key members of the AP-1 complex, including C-Jun, Jun B, Jun D, and Fra-1, but not Fra-2.

DBZIM Induced Apoptosis and Reduced pAKT in Several Other Tumor Cell Lines

To investigate whether the effect of DBZIM is liver cell specific, tumor cells of lung, breast and gastric cancer cells were treated with DBZIM, and it was found that the same agent caused significant cell death in all the tumor cell lines tested. The IC50 value (determined at day 3) was 50 µM for H1299 (lung cancer); 50 µM for MCF-7 (breast cancer), and 40 µM for AGS gastric cancer at day 3 (Table 3). Interestingly, DBZIM showed much less cytotoxicity on the normal (non-cancerous) lung cells (IMR90). Further, treatment of AGS and H1299 with DBZIM resulted in morphological (apoptotic look) changes and significant reduction in the number of cells (FIGS. 29A and 29B). It was also found that DBZIM significantly reduced the growth of two glioma cell lines, U87MG (human) and C6 (rat) (FIGS. 30A and 30C), with IC50 (determined at day 2) for U87 MG and C6 being 2.1 mM and 1.0 mM, respectively.

Figure 30:
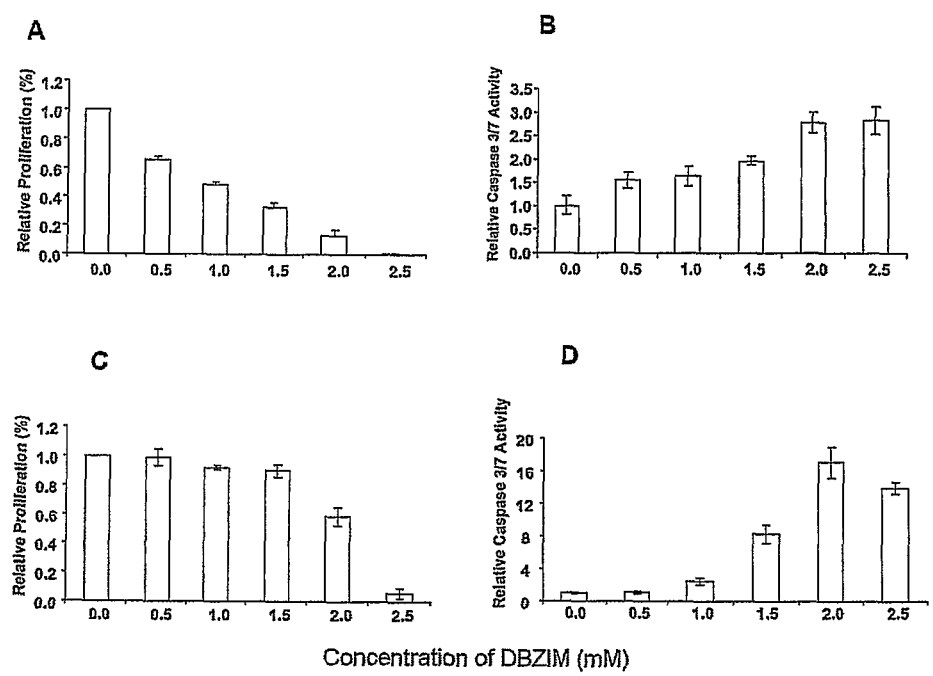
FIG. 30. DBZIM inhibited cell proliferation in glioma cell line C6 (A) and U87 MG (C) and induced caspase 3/7 activity in C6 (B) and U87 MG (D). C6 or U87 cells were incubated with DBZIM of various concentrations for 48 hr for proliferation assay and 6 hr for caspase 3/7 activation assay. Proliferation was measured using MTS kit from Promega and expressed as relative cell proliferation with control group was normalized to 1. Caspase 3/7 activity was quantified using a kit from Promega and also expressed as relative caspase 3/7 activity of treated groups over control group.

To determine whether cells undergo apoptosis, Western blotting was first performed for a caspase-3/9 and PARP activation with proteins from MCF-7 and AGS treated with DBZIM. Results showed that DBZIM time-dependently increased caspase-3/9 and PARP activity, suggesting that the DBZIM-treated cells undergo apoptosis in breast cancer cell line MCF-7 (FIG. 31A) and in wild-type p53 gastric cancer cell AGS (FIG. 31B). Similarly we observed a DBZIM-induced elevation of caspase 3/7 in C6 (by 3 folds at 2.0 mM) and in U87 MG (by 17 folds at 2 mM) (FIGS. 30B and 30D).

Figure 32:
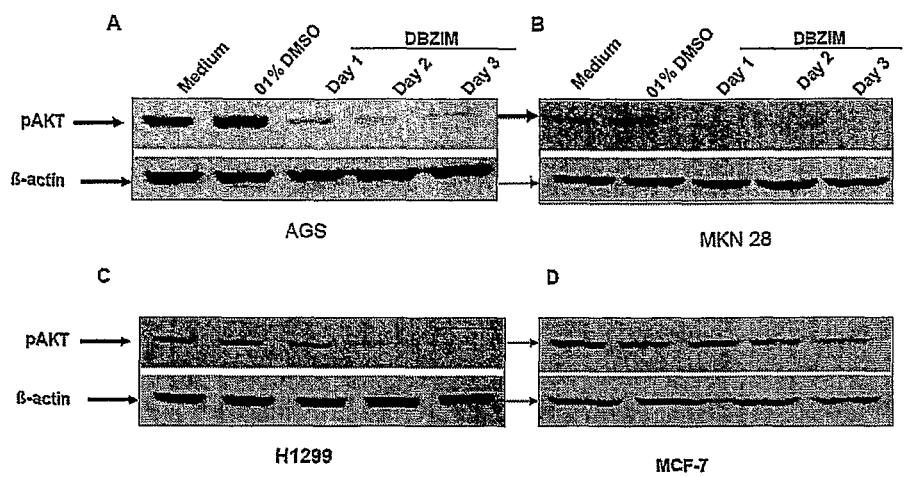
FIG. 32. DBZIM inhibits phosphorylation of Akt. When AGS, MKN28, H1299 and MCF-7 cells were treated with DBZIM at their corresponding IC50 concentration, phosphorylation at serine 473 of Akt was downregulated in p53 wild type cancer cell line AGS (A), in p53 mutant gastric cancer cell MKN 28 (B), in p53 null Lung cancer cell H1299 (C), and in p53 wild type breast cancer cell MCF-7 (D). Time course inhibition of phosphorylated-AKT was shown by Western blot. β-actin was used as an internal loading control.

The Akt (also known as protein kinase B) kinase signaling pathway is activated in a variety of carcinomas of lung, breast, colon, and pancreatic and other tumor types through overexpressing the Akt protein itself and/or increasing phosphorylation of Akt. This study provided evidence that DBZIM is particularly efficacious in inducing apoptosis in AGS, H1299 and MCF-7 cells through a mechanism involving the reduction in the levels of the, phospho-AKT. Next it was investigated whether DBZIM modulated the Akt pathway in H1299, MCF-7, AGS and NKN28, DBZIM treatment resulted in an appreciable down-regulation of the active form of Akt (phospho-Ser473-Akt) from 24 h to 72 h, without any changes in β-actin in all four cancer cell lines tested (FIG. 32). Taken together, these data suggest that DBZIM is a potent suppressor of AKT-mediated signaling and is independent of p53 status.

DBZIM Reduced Tumor Growth in a Xenograft HCC Mouse Model

Figure 33:
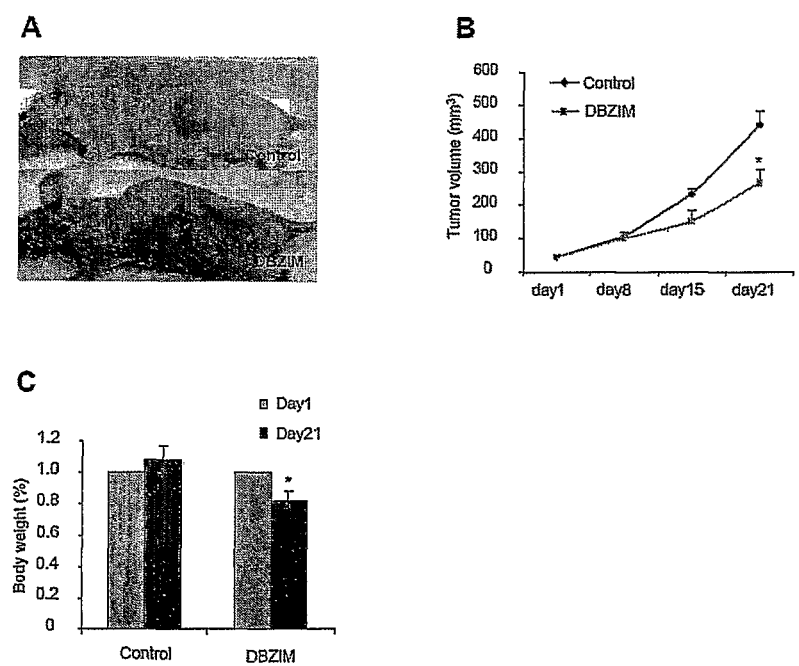
FIG. 33. DBZIM reduced HCC tumor in vivo. Tumors in the HCC-xenografted mice in the control group and in the treatment group, 3 weeks post inoculation, are shown in (A). The tumor growth curve and body weight chart are depicted in (B) and (C), respectively. *P<0.01.

Several HCC cell lines (HepG2, Hep3B, Huh7, PLC, and HLE) were tested for their ability to efficiently induce HCC in nude mice, and it was found that Huh7 line was among the most efficient. Therefore a murine HCC model was established using the Huh7 cells for testing the anti-tumor efficacy of DBZIM in vivo. Three weeks into the treatment, difference in tumor size was apparent between mice in the control and the treatment group (FIG. 33A). Measurement showed that the tumor volume in the DBZIM-treated mice was significantly reduced by 40% (P<0.01) when compared to the control mice (FIG. 33B). It was noted that the body weight (including a reduction in the tumor weight) of the DBZIM-treated mice decreased by 17% (P<0.01) after three weeks of treatment (FIG. 33C).

Anticancer Activities of Additional IMSs

Determination of IC50 for 46 IMS in HLE Cells

A total of 46 IMSs were cultured in the HLE cell line for 48 h to determine rough IC50 values for individual compounds. (Table 2) After the initial screening, seven of the IMSs, compound C, compound 9, IBN-15, IBN-19, IBN-24, IBN-25 and IBN-32, were used for subsequent experiments.

Endogenous Expression of p53

Figure 34:
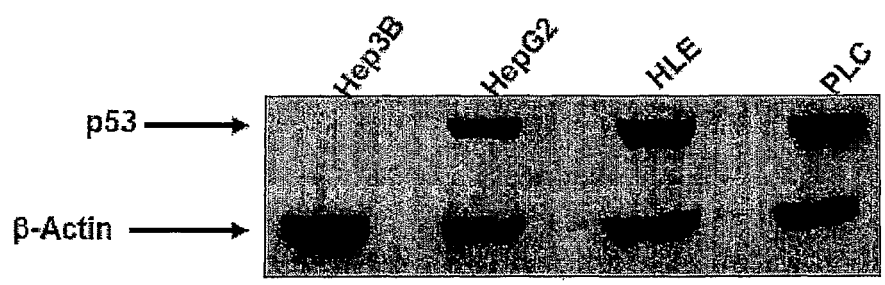
FIG. 34. Endogenous expression of p53. Cell lysates from Hep3B (p53 null), Hep G2 (wild type), Hle and Plc (p53 mutant) were subjected to Western blotting using p53 (DO-1) and actin antibodies.

The expression level of p53 in Hep 3B (p53null), HepG2 (p53 wild type), and HLE and PLC (p53 Mutant) hepatocarcinoma cells was determined by Western Blot. (FIG. 34). The expression of p53 was high in cells bearing mutant p53, as compared to cells with the wild type p53.

IMSs Inhibited Proliferation of HLE Cells

Figure 35:
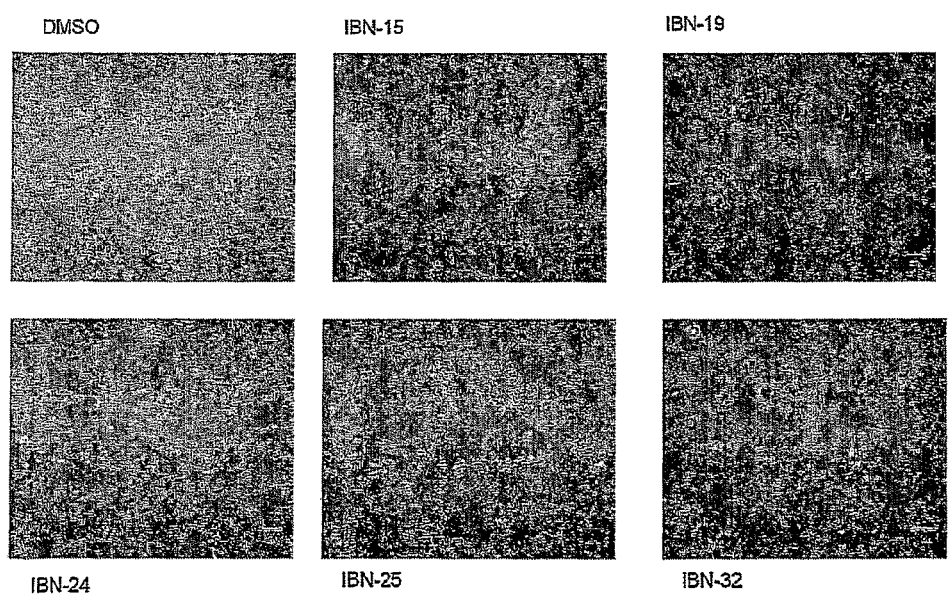
FIG. 35. Phase-contrast microscopy of cells exposed to IMSs. Pictures from phase-contrast microscopy show cell cultures after exposure to IMSs (IBN 15, IBn 19, IBN 24, IBN 25 and IBN 32) for 72 h, respectively. Extending the length of exposure caused increased loss of confluency in cell cultures.

The effect of IMSs (IBN-15, IBN-19, IBN-24, IBN-25 and IBN-32) on the proliferative properties of p53 mutant cell line HLE was examined. The cytotoxicity activity and proliferation inhibition of IMSs in tumor cells were measured by MTT. The treatment of HLE liver cancer cells with IMSs resulted in a dose dependent inhibition of cell proliferation. The control experiments with DMSO alone (0.05% v/v) had no effect on cell proliferation. The $IC_{50}$ value for IBN-15, IBN-19, IBN-24, IBN-25, and IBN-32 in HLE cells was estimated to be 60 μm, 90 μm, 90 μm, 30 μm, and 20 μm at 72 h. While the $IC_{50}$ value for IBN-15, IBN-19, IBN-24, IBN-25 and IBN-32 in HLE cells at 120 h was found to be 20 μm, 28 μm, 30 μm, 35 μm, and 20 μm. (Table 4) Microscopic observation on the cell cultures visually confirmed the inhibition on cell proliferation by IMSs. (FIG. 35)

IMSs Induced Apoptosis

Figure 36:
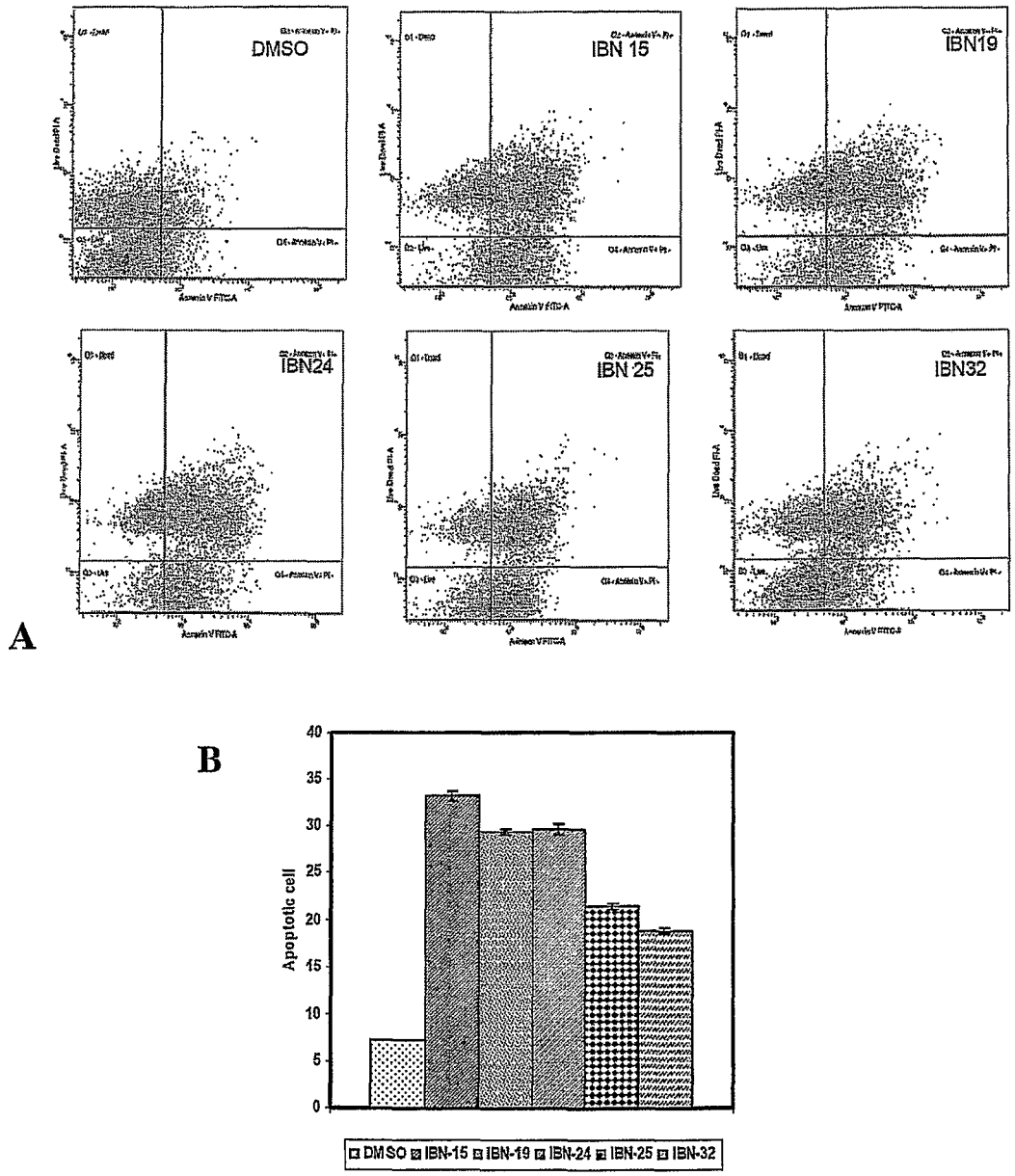
FIG. 36. IMSs induce apoptosis in Hepatocarcinoma cells. A) Cells were treated with vehicle and IBN 15, IBN 19, IBM 24, IBN 25 and IBN 32 for 72 h, and apoptosis was quantified using Annexin V-FITC/PI staining followed by flow cytometric analysis. 10,000 cells were detected for every sample. Living cells are in the bottom left quadrants (FITC– and PI–), early apoptotic cells in the bottom right quadrants (FITC+ and PI–), and late apoptotic cells in the upper right quadrants (apoptotic FITC+ and PI+). B) The percentage of apoptotic cells with respect to different IMSs.

As the data indicated that IMSs significantly inhibited cell growth in HLE cells, Annexin V-PI dual-staining assay was performed in the same cell type under the same conditions to investigate whether the growth inhibition resulted from cell apoptosis. Cells undergoing apoptosis would stain positive for Annexin and negative for PI (quadrant 4, Q4). Cells which stained positive for both Annexin V-FITC and PI (Q2) are either at the end stage of apoptosis or undergoing necrosis, and those which stained negative for both Annexin V-FITC and PI (Q3) were alive or undergoing undetectable apoptosis. In contrast, cell debris stained only for PI (Q1). As shown in FIGS. 36 A and B, IMSs IBN-15, IBN-19, IBN-24, IBN-25, and IBN-32 induced 33%, 29%, 29%, 21%, and 18% (Q2) cell apoptosis, respectively, whereas fewer apoptotic cells (7.2%) were observed for DMSO treated cells, confirming that the IMS-induced cell growth inhibition has a significant apoptotic component IMSs Changed Cell Cycle Distribution To analyze whether the IMSs-induced inhibition of cell growth in HLE cells was accompanied by alterations in cell cycle distribution, the percentage of cells in the different phases of cell cycle and apoptotic index were analysed by flow cytometry. When cells were treated with IBN-15, IBN-19, IBN-24, IBN-25, and IBN-32 at a concentration corresponding to their respective IC-50 value (i.e., 60 μm, 90 μm, 90 μm, 30 μm, and 20 μm) for 72 h, a significant accumulation of cells in the sub-G0 phase and a corresponding reduction in the number of cells in the G2/M phase was found. The representative results are shown in FIGS. 37A, 37B and 37C). Two percent of the cells in the control culture (with DMSO) were in sub-G0 phase, whereas the numbers dramatically climbed up to 20% in the IMS-treated cultures. Similarly in control culture, 50% cells were in the G1 phase, 24% were in the S phase, and 30% were in the G2/M phase at 72 h, whereas in the IMS-treated cultures (with IBN-15, IBN-19, IBN-24, IBN-25, and IBN-32), 42%, 29%, 28.6%, 34.5%, and 32.3% of the cells were in the G1 phase; and 19.7%, 19.8%, 11.34%, 14.3%, and 14.6% in the S phase; and 21%, 23.7%, 16.3%, 19.4%, and 18.9% in the G2/M phase, respectively.

IMSs Induced Apoptosis Via Caspase Activation

Figure 38:
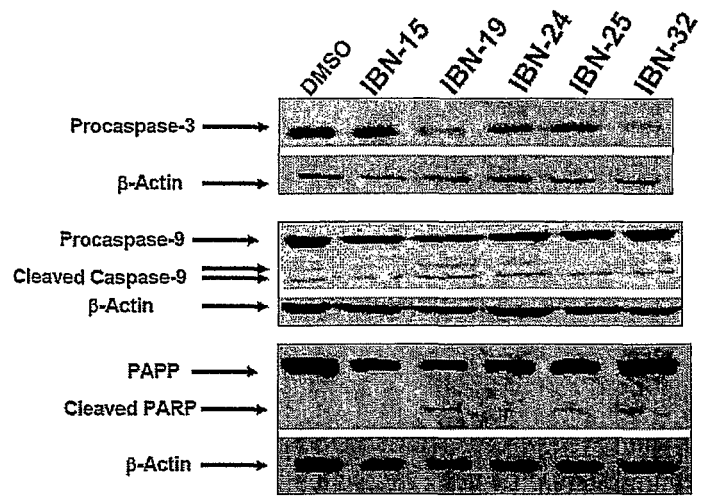
FIG. 38. IMSs, induce cleavage of caspase-3, caspase-9 and PARP. Western blot analysis for the effect of IBN 15, IBM 19, IBN 24, IBM 25, IBN 32 on the cleavage of caspase-3, Caspase-9 and PARP in HLE cells after 72 h exposure to indicated doses of IMSs.

To further determine whether the apoptotic activity of IMSs is due to caspase activation, Western blot analysis was performed with total protein lysates from HLE cells. It was observed that IBN 19, 24 and 25 induced significant activation and cleavage of caspase 3 and caspase 9 and PARP (FIG. 38), suggesting that the compounds induce cells to undergo apoptosis.

IMSs Increased the Expression of p53 and Phosphorylated p53 (Ser15, 20, 46 and Ser 392)

Figure 39:
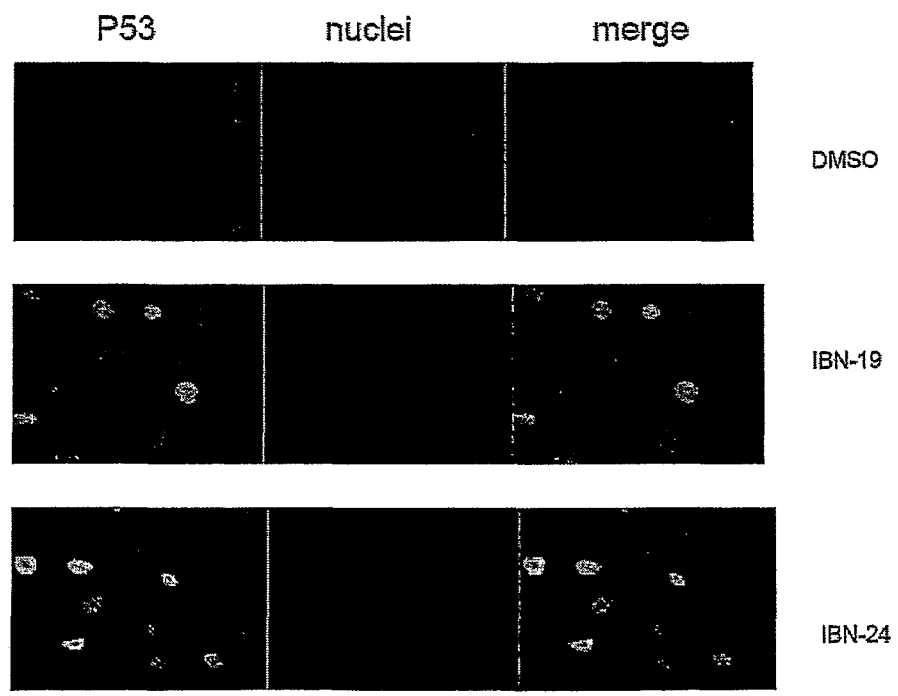
FIG. 39. IMSs-induced apoptosis was accompanied by accumulation of p53 in the nucleus. HLE cells were treated with the indicated dose of IBN 19 and IBN 24 for 48 h. The treated cells were fixed with 4% formaldehyde, immunostained with anti-p53 (green fluorescence) and DAPI (blue fluorescence), and analysed by confocal microscopy.

In order to determine whether the activation of the p53 pathway was involved in IMS-induced apoptosis, analyses of p53 and its down stream effectors were performed in HLE cells, which carry the mutant p53. Immunocytochemical analyses revealed that IMSs (IBN-19 and IBN-24) induced p53 expression and accumulation in the nucleus (FIG. 39).

Because phosphorylation at the Ser 15 site of p53 by ATM is often observed when cells receive DNA damage signals. It was speculated that ATM may also respond to IMSs in the HLE cells. Tt has been reported that chemical agents that damage DNA act through posttranslational modifications of p53 and activate its downstream targets in various human cancer cells (Banin et al. 1998; Canman et al. 1998). The present results also demonstrated that these IMSs induced p53 modifications, such as phosphorylation at Ser-15 (FIG. 40) due to up-regulation of ataxia telangiectasia-mutated (ATM) kinase gene. Furthermore, IMSs induced phosphorylation at position at Ser-20, -46 and -392. These posttranslational modifications of p53 appear to be responsible for the cell cycle arrest (FIG. 40).

IMSs Induced the Execution of Apoptosis Through Activation of the Mitochondrial Pathway To investigate the mitochondrial events involved in IMSs-induced apoptosis, the changes in the levels of pro-apoptotic protein Bax, and anti-apoptotic protein Bcl-2 were analyzed. Immunoblot analysis showed that treatment of HLE cells with various IMSs increased Bax protein level and simultaneously decreased Bcl-2 level (FIG. 41).

Real-Time RT-PCR Profiling of Gene Expression in IMS-Treated Cells

To obtain more information on how the IMSs influence other gene expression in the HLE cells, 84 genes related to p53 signal transduction were profiled by using the $RT^2$ Profiler array (Super Array Bioscience) (FIG. 42A, B, C, D, E). The array includes keys genes relevant to p53, apoptosis, cell cycle, cell growth, proliferation, differentiation, and DNA repair. It was found that ATM gene expression at 48 h after IBN-19, IBN24 and IBN-25 treatment was significantly increased by 36-, 4.6- and 9-folds respectively, when compared to that of the control (FIG. 42E). These data show that IMSs induce transcriptional up-regulation of ATM gene, which in term elicits a specific p53 phosphorylation at Ser-15 in the HLE cells.

Figure 42:
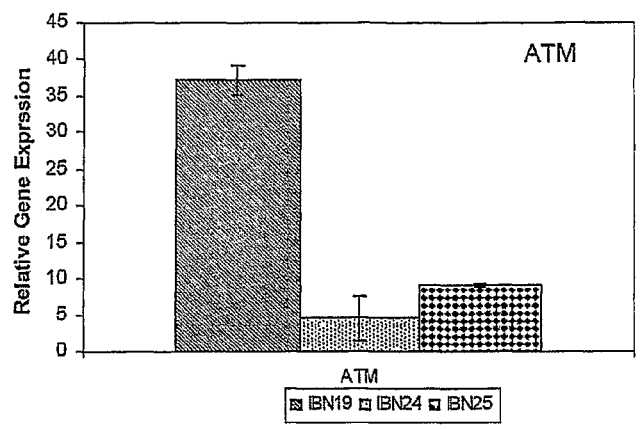
FIG. 42. Real-Time PCR array analysis of p53 signaling pathway-associated gene expression. (A) Anti-apoptotic genes. (B) Growth inhibition gene SESN2. (C) Cell cycle check point genes. (D) Cell proliferation genes. (E) DNA repair gene ATM. The relative level of gene expression was normalized with housekeeping gene GAPDH. Values are expressed as mean±standard deviation.

The results demonstrated that IBN-24 and IBN-25 significantly down regulated anti-apoptotic genes BCl-2 (FIG. 42A). The results from the quantitative RT-PCR analysis also indicated that SESN2 gene was markedly induced by IBN-19, as compared to untreated (FIG. 42B). Further, the results also demonstrated that cell proliferation genes Mcl1, Egr1, Foxo3, Jun, Mdm4, Nf1, Prm1D, Sesn1, E2f11, Prkca and, Brca1 were significantly down regulated in the IBN-24 and IBN-25 treated cells as compared to control cells. (FIG. 42 D) The important cell cycle regulatory genes cdk4, cdc25A, cdc2, e2f1, and Hk2 were significantly downregulated. (FIG. 42C)

Figure 43:
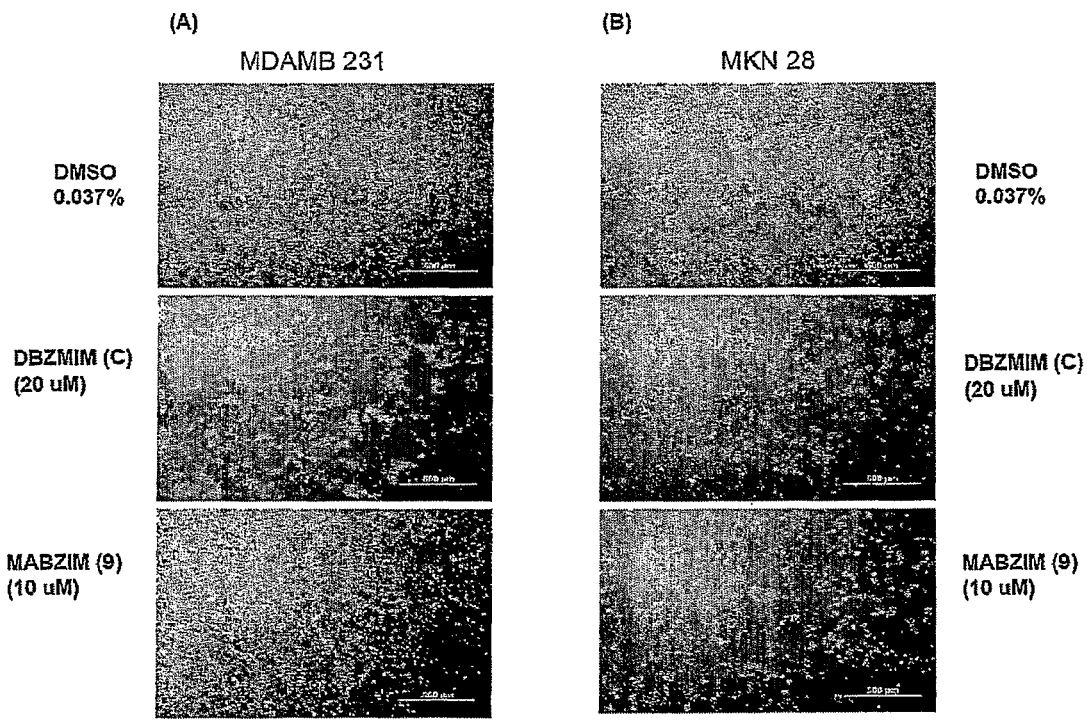
FIG. 43. Effect of Compound C (DBZMIM) and compound 9 (MABZMIM) on lung cancer and gastric cancer cells. Compound C (DBZMIM) and compound 9 (MABZMIM) induced morphological change and apoptosis in lung cancer cells MDAMB 231 (A) and in gastric cancer cells MKN 28 (B), 120 h after the treatment.

Compound C (DBZMIM) and Compound 9 (MABZIM) Inhibit Proliferation of Gastric and Breast Cancer Cells In this study, the anti-cancer effects of compound C and compound 9 on p53 mutant gastric cancer cell line MKN 28 and p53 mutant breast cancer cell line MDAMB231, as well as on wild type p53 breast epithelial cells (MCF-10A) was preliminarily explored. First, the cytotoxic effect of these drugs on these cells was investigated using the MTT assay. Cells were seeded into 96 well plates and treated with increasing concentrations of these synthetic organic molecules for 72 h, and then the cytotoxic effect was measured. In response to these synthetic organic molecules, the normal MCF-10A cells showed resistance to both organic molecules with no $IC_{50}$ (concentration of the drug that leads to 50% lethality) (Table 7). Both the cancer cell lines MKN 28 and MDAMB231 were the most sensitive towards compound 9, with IC-50 being 10 and 20 µM (Tables 5 and 6). On the other hand, compound C killed both MKN 28 and MDAMB231 with the same IC50 of 35 µM (Tables 5 and 6). These IC50 values were similar to those obtained with a commonly used cancer drug 5-Fluorouracil (5-FU). Morphology of the cells treated with compound C and compound 9 respectively was shown in FIGS. 43A and 43B.

Compound 9 Inhibited Proliferation of HCC Huh7 Cells in Mice

Figure 44:
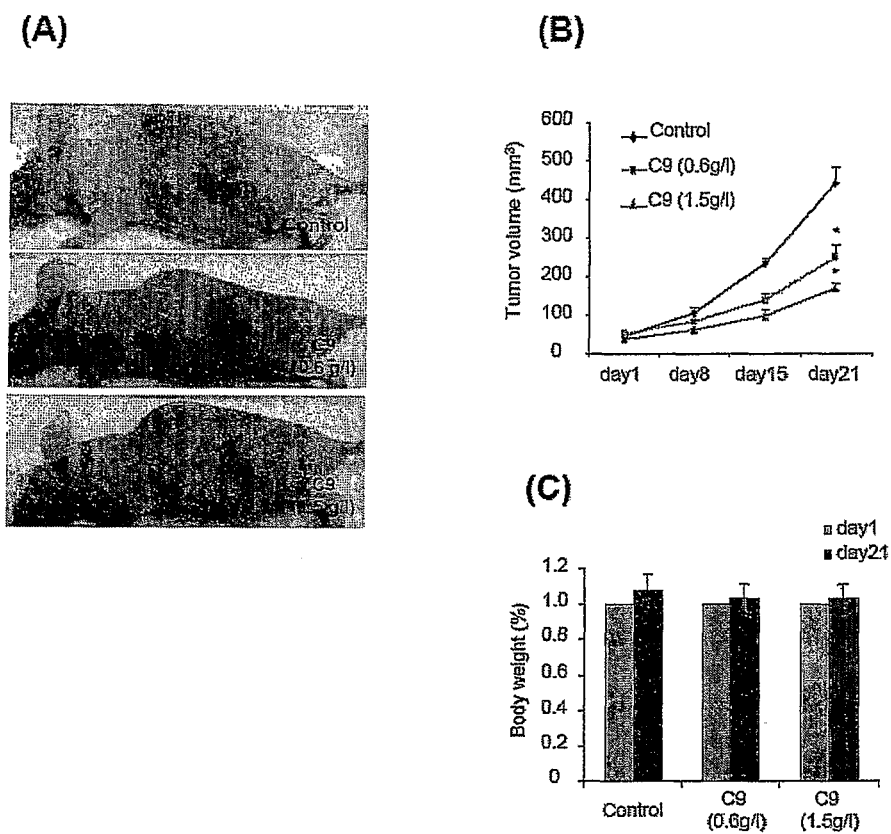
FIG. 44. Effect of compound 9 on HCC-xenografted mice. Tumors in the HCC-xenografted mice in the control group and in the treatment group, 3 weeks post inoculation, were shown in (A). The tumor growth curve and body weight chart was depicted in (B) and (C), respectively. *P<0.01.

Several HCC cell lines (HepG2, Hep3B, Huh7, PLC, and HLE) were tested for their ability to efficiently establish HCC in nude mice, and found that Huh7 line was among the most efficient. Therefore a murine HCC model was established using the Huh7 line and one of the IMSs (compound 9) was tested to assess its anti-tumor efficacy. Three weeks into the treatment, significant difference in tumor size was apparent between mice in the control and the treatment group (FIG. 44A). Measurement showed that the tumor volume in the C9-treated mice was significantly reduced by 43% and 62% ($P<0.01$) at 0.6 g/l and 1.5 g/l, respectively, when compared to the control mice (FIG. 44B). No change in body weight or gross pathology was noted for the C9-treated mice, when compared to the control mice (FIG. 44C), implying lack of significant general toxicity associated with the C9 under the current dosing scheme.

Discussion

Anti-Oxidative, Anti-Inflammatory and Anti-Fibrotic Properties of IMSs

Toxicity of IMSs

The IC50 of the most frequently tested compound in this study, DBZIM, was 1.7 mM, and the IC50 values for DPIM and DBIM with aliphatic substitutions were 2-4 mM. The in vivo toxicity for DPIM and DBIM was roughly one-tenth of that for DBZIM. In contrast, the IC50 values for natural antioxidants EGCG and genistein in HSCs were much lower (25-75 µM) (Kang et al. 2001, Chen et. al 2002, Chen et. al 2003, Higashi et al. 2005, Zhang et al. 2006). Intriguingly, preliminary in vitro and in vivo data seemed to suggest, in contrast to common belief, that the synthetic IMSs might have a better safety profile than the natural anti-oxidants. The mild toxicity of this class of compounds certainly helped to pat forth the prospect of using IMSs as the basic units to synthesize additional candidates with novel properties and functionalities tailored to various specific therapeutic needs.

IMSs Demonstrated Anti-Oxidative Property through Neutralization of ROS and Induction of Phase II Anti-Oxidative Enzyme Cells or tissues maintain a redox hemeostasis when the rate of ROS production and scavenging capacity are essentially in balance. Changes in oxidant/anti-oxidant balance will trigger responsive redox signaling. It has been reported that oxidative stimuli can induce expression of anti-oxidative defense enzymes such as SODs, CAT and GPx, etc., to restore the original redox homeostasis or to reach a new equilibrium (Droge 2002). Redox regulation is also partly mediated through the cellular GSH and the GSH/GSSG redox state. GSH plays a key role in cellular anti-oxidative processes by serving as an electron donor to GPx in the reduction of hydrogen peroxide to water, and as a nucleophilic co-substrate to GST in the detoxification of xenobiotics. Anti-oxidants exert their effect mainly through three different pathways: (1) neutralization of cellular ROS generated during metabolism and immune response, (2) induction of endogenous anti-oxidative enzymatic activity, and (3) chelation of iron or copper ions that catalyze the generation of hydroxyl radical. GPx, CAT and SOD, which constitute the first line of cellular anti-oxidative defense, are directly involved in the neutralization of ROS. GPx enzyme reduces $H_2O_2$ to $H_2O$, while GSH functions as a cofactor and is consequently oxidized to GSSG. CAT is a peroxisomal enzyme and converts $H_2O_2$ to $H_2O$. SOD catalyzes the dismutation of superoxide. There are three forms of SOD: extracellular and intracellular copper/zinc (Cu/Zn) SODs, and a mitochondrial manganese (Mn) SOD. GST is a phase II anti-oxidant enzyme. It has been reported that activation of HSCs is associated with the loss of GST activity in culture (Whalen et. al 1990).

In this study, IMSs effectively attenuated ROS (in particular $H_2O_2$ and lipid peroxides, which react to 2',7'-dichlorofluorescein diacetate (DCF-DA) probe (Halliwell et al. 2004) in a dosage-dependent manner. While the level of GSH remained relatively constant, the amount of GSSG was dramatically decreased, resulting in a significant increase in the GSH/GSSG ratio. Moreover, the enzymatic activities of GPx and CAT, which are responsible for reducing hydrogen peroxide to water, were slightly attenuated. Taking all the data together, it is proposed that IMSs might have mainly exerted their anti-oxidant effect through the direct neutralization of ROS, such as hydrogen peroxide. Therefore, the burden on cellular anti-oxidative defense was alleviated by the exogenous synthetic anti-oxidative IMSs, resulting in a decrease in the expression of first-tier anti-oxidative enzymes. In the meantime, the effect of IMSs on GSH synthesis and anti-oxidative enzymes showed a general pattern of attenuation at low dosages, less potent attenuation and even enhancement at high dosages. This suggested that DBZIM worked through different mechanisms at low and high dosages. At a low dosage, the anti-oxidative pathway predominated by direct reaction to remove $H_2O_2$ so that GPx and CAT activities were reduced. In contrast, there might be a synergistic effect between direct neutralization of $H_2O_2$ and induction of anti-oxidant enzymes at a high dosage. It was reported that a reduction in the battery of anti-oxidative enzymes GPx, CAT and SOD as observed in the experimental cholestasis can be reversed by the endogenous anti-oxidant melatonin (Padillo et al. 2004). Interferon-alpha has been shown to increase GPx activity in activated HSCs (Lu et al. 2002). On the other hand, it has been shown that oxidative stimuli could induce anti-oxidative enzymatic activities (Droge 2002). One recent paper also showed that a high dosage of NAC (30 mM) shifted cellular redox state towards oxidative stress, as indicated by enhanced reduced glutathione, oxidized glutathione, GPx activity and ROS production in endothelial cells. In this study, high-dosage IMSs showed a trend of enhanced GPx and CAT activities. This result, along with other findings that high-dosage IMSs imposed greater effect in attenuating ROS production (FIGS. 2a and 2b) and GSSG (FIGS. 3c and 3d), and inducing GSH/GSSG ratio (FIGS. 3e and 3f), suggested that IMSs at high dosage enhanced cellular defense activity against oxidative stress by synergizing neutralization of ROS and induction of endogenous anti-oxidant enzymes. In addition, IMSs had little effect on the total SOD (Gu/Zn-SOD and Mn-SOD) activity, suggesting that the compounds did not react with superoxide and have little influence on the cellular response to remove superoxide.

Meanwhile, phase II enzymes such as total GST were enhanced in activity under the treatment of IMSs. It was known that GSTs protect the cells against oxidative toxicants by conjugating the xenobiotics to GSH, thereby neutralizing their electrophilic sites and rendering the product water-soluble. The enhancement of GST activity indicated that the cells have better capability of getting rid of oxidants such as lipid peroxidation products, thereby minimizing the cellular oxidative injuries.

The anti-oxidative property of IMSs was also demonstrated in primary HSC cells. DMSO induced cellular oxidative stress, and imposed lethal effect on primary HSC cells. The presence of IMSs effectively protected the primary HSC cells from dying in the culture medium containing 0.2% (v/v) of DMSO. This finding implies a potential application of this group of compounds in cell-based drug screening assays and tissue engineering.

IMSs Showed Anti-Inflammatory Effect through Suppression of NF-κB and IL-6

Transcription factor NF-κB is found in the cytosol bound to inhibitory protein known as IκB. When the cells are under various stress conditions, such as infection, inflammation and tissue repair, NF-κB is activated and translocated into the nucleus where it binds to DNA and regulates the transcription of gene-encoding proteins involved in immune or inflammatory responses (Vasiliou et al. 2000, All et al. 2004). The activation of NF-κB is associated with phosphorylation and subsequent degradation of IκB. The NF-κB-responsive site has been identified and characterized in the promoters and enhancers of many genes, including IL-6 and ICAM-1 (Ali et al. 2004). NF-κB is also known to be sensitive to oxidative stress. Most agents activating NF-κB are either modulated by ROS or oxidant themselves. It has been reported that the treatment of anti-oxidant resveratrol (Chavez et al. 2007) or vitamin E (Liu et al. 1995) attenuated NF-κB elevation induced in carbon tetrachloride experimental fibrotic rodents.

To test whether IMSs are able to suppress NF-κB activation and in turn regulate immune and inflammatory responses, the protein expression of active NF-κB was assayed by Western blotting and NF-κB-responsive IL-6 gene transcription. Our data showed that IMSs could effectively interrupt the activation of NF-κB, and as a result, down-regulate the gene expression of IL-6 (FIGS. 10a-c and 11). These data indicated that IMSs have anti-inflammatory effect by down-regulating IL-6 transcription through NF-κB signaling.

IMSs Showed Anti-Fibrotic Properties through Suppression of HSC Activation

HSCs are well-recognized cellular regulators in the development of hepatic fibrosis. HSC activation, associated with enhanced secretion of pro-fibrogenic, pro-inflammatory cytokines (such as TGF-β1 and IL-6) is characterized by the over-expression of SMAA, and results in the over-deposition of ECM proteins including col1a1 and fibronectin. The anti-fibrotic effects of IMSs were evident by the suppression of HSC activation markers (GFAP and SMAA) and fibrotic endpoints (col1a1 and fibronectin) in a dosage- and time-dependent manner. A transiently induced SMAA expression was observed under the treatment of high-dosage TDBZIM (FIG. 7b). The underlying mechanism was not clear, but might be related to the radical-like nature of NHC with bulky N-substituents (Bourissou et al. 2000). SMAA might have a transient over-response to excess radicals. Nevertheless, IMSs of moderate concentrations were generally able to attenuate SMAA expression (FIGS. 6a, 6b and 14b). IMSs also consistently suppressed the mRNA and protein expression of col1a1 and fibronectin (FIGS. 6a-b, 7c-d, 13 and 14c-d), which as a net effect prevented or slowed down the progression of fibrosis.

Figure 13:
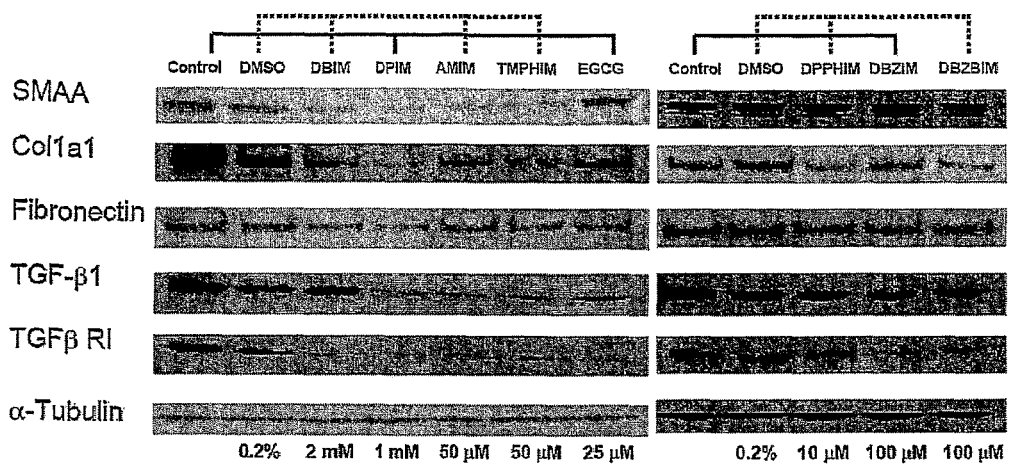
FIG. 13. Western blotting of SMAA, col1a1, fibronectin, TGF-β1, TGFβ RI protein expressions in HSC T6 cells treated with various IMSs for 48 h. (A) DBIM (1 mM), AMIM (50 μM), TMPHIM (50 μM), DPPHIM (10 μM) and DBZBIM (100 μM) were dissolved in DMSO with a final DMSO concentration of 0.2% (v/v). DPIM (2 mM), EGCG (25 μM) and DBZIM (100 μM) were dissolved in H$_2$O. Alpha-tubulin was used as the loading control. Densitometric measurement of protein band intensity was normalized against the respective vehicle control. (B) Relative densitometric quantification of protein band intensity. The vehicle treated sample was normalized to 1.

TGF-β1 is the most potent pro-fibrogenic cytokine, which is over-expressed in activated HSCs. TGF-β1 signaling is initiated by the binding of the active form of TGF-β1 to type II receptor, and subsequently leading to the phosphorylation of type I receptor (TGFβ RI). Activated TGFβ RI recruits Smads protein, and propagates the downstream signal to regulate the gene expression of matrix proteins (Fu et al. 2006). To understand IMSs' effect on treating liver fibrosis, TGF-β1 and TGFβ RI in T6 cells under IMS treatment were measured. The data showed that IMSs could effectively interfere with TGF-β1 signaling by suppressing the gene and protein expressions of total TGF-β1 and TGFβ RI (FIGS. 9a-c and FIG. 13). It was recently reported that EGCG could decrease the active form of TGF-β1 in primary HSC cells (Fu et al. 2006). In the present study it was also shown that EGCG could suppress the production of total TGF-β1 protein in T6 cells (FIG. 13). Some IMSs, particularly DPIM, showed greater suppression of TGF-β1 and TGFβ RI than EGCG under the test conditions. Resveratrol, another anti-oxidant from grape skin, has been reported to effectively attenuate TGF-β1 protein elevation induced in an experimental fibrotic rat model (Chavez et al. 2007).

Activation of HSC is also associated with elevated levels of NF-κB and NF-κB-responsive genes, including IL-6 (Mann et al. 2006). The role of NF-κB is to maintain HSCs in the activated state and promote a chronic wound healing response. In fact, NF-κB has been implicated in various aspects of liver disorders, including hepatic inflammation, fibrosis, and the development of hepatocellular carcinoma (Elsharkawy et al. 2007). In this study, IMSs greatly suppressed active NF-κB p65 protein (FIG. 11), while not affecting the cytosolic NF-κB P65 level (data not shown). AP-1 is a homodimer or heterodimer composed of at least one Jun family protein (c-Jun, JunB and limn) and another member from the Fos family (c-Fos, Fra1 and Fra2). It has been reported that JunD is functionally the most important AP-1 factor in activated HSCs required for the induction of IL-6 and the tissue inhibitor of metalloproteinase I (TIMP-1) gene transcription (Smart et al. 2001). It is known that HSC T6 cells express all members of Jun and Fos proteins (Zhang et al., 2006). Under the influence of IMSs, c-Fos, JunD and Fra-1 levels were attenuated (FIG. 11). In line with the down-regulation of JunD, IL-6 gene transcription was suppressed (FIGS. 10a-c). In short, IMSs might prevent hepatic fibrosis through the suppression of HSC activation, and by decreasing the deposition of ECM proteins (col1a1 and fibronectin) and the production of pro-fibrogenic cytokines (TGF-β1, TGFβ RI and IL-6) mediated through NF-κB and AP-1 signaling.

NHC Precursors could be Drug-Like Compounds

ROS has been implicated in many physiological conditions, including neurodegenerative diseases, cardiovascular diseases, stroke, heart attack, cancer, aging and fibrosis, etc. Therefore, anti-oxidation has been pursued as a therapeutic strategy for a number of diseases. Dietary anti-oxidants have been widely used to ameliorate excessive oxidative stress both in animal models and humans. For example, resveratrol has been shown to extend the lifespan of various species, and to be effective at improving the health and survival of mice on a high-calorie diet (Baur et al. 2006). Tea polyphenols (EGCG being the most abundant catechin) have been shown to inhibit carcinogen-induced DNA damage in animal models of skin, lung, colon, liver and pancreatic cancers (Frei et al. 2003). However, stringent scientific proof for the efficacy of natural anti-oxidants has not been established (Droge et al. 2001) due to various factors. Some of the notable limitations for using natural anti-oxidants as therapeutics include low potency and fast turnover during metabolism. By comparison, less effort has been devoted towards studying synthetic anti-oxidants due to safety concerns. Nevertheless, some progress has been made in this direction. For example, natural anti-oxidant has been modified to enhance its potency (Keum et al. 2007). Synthetic mimics of SOD and catalase have been shown to be effective in rodent models of ischemia and Parkinson's disease (Peng et al. 2005). Even more encouragingly, a class of nitron-free radical trap agents, alpha-phenyl-N-tert-butyl-nitron (PBN) and disodium 2,4-disulfophenyl-N-tert-butylnitrone (NXY-059), has been shown to be potent neuroprotective agent (Maples et al. 2004), and has demonstrated anti-cancer activity in hepatocellular carcinoma through its anti-inflammatory properties (Floyd 2006). These examples suggest that it is possible to develop therapeutic drug candidates based on synthetic anti-oxidants. It is believed that this report represents the first effort towards exploring the potential therapeutic effect of IMSs. IMSs are precursors of NHCs, in which the electronic structure and stability, and thus, therapeutic safety and efficacy can be tuned by varying the N-substituents. NHCs with bulky substituents favor a triplet ground state and exhibit radical-like reactivity, while those with smaller substituents adopt a singlet ground state and show both nucleophilic and electrophilic behavior (Bourissou et al. 2000).

In this study, IMSs demonstrated potent anti-oxidative, anti-inflammatory and anti-fibrotic properties in cultured HSCs. At the same time, IMSs showed relatively low and tunable toxicity with IC50 in the range of 35 μM to 3.1 mM. It is hypothesized that the anti-fibrogenic and anti-inflammatory effects of the IMS compounds are derived through the anti-oxidative property targeted at inhibiting HSC activation. The radical scavenging property of the IMSs is presumably originated from the product after a series of chemical reactions including: (1) the spontaneous conversion of IMSs to NHCs preferably under a basic condition, (2) the interaction of the NHCs at the carbon 2-position with free radicals such as ROS resulting in the formation of intermediate active radicals and the neutralization of the free radicals.

The findings of this study support this hypothesis. Although the underlying molecular mechanism is not yet well understood, the effects of IMSs are shown to be mediated through NF-κB and AP-1 transcription factors, and TGF-β1 and IL-6 signaling pathways. Large-scale screening of lead compounds for the treatment of liver fibrosis can be performed using the surrogate GFAP biomarker driving a fluorescent reporter. The radical scavenging and the anti-inflammatory properties are central to IMSs' therapeutic effect in treating liver fibrosis in this study. Further exploration may reveal therapeutic potential for this group of compounds in treating other degenerative and aging-related diseases.

Effect of DBZIM on Hepatocellular Carcinoma and Other Tumour Cells

Figure 22:
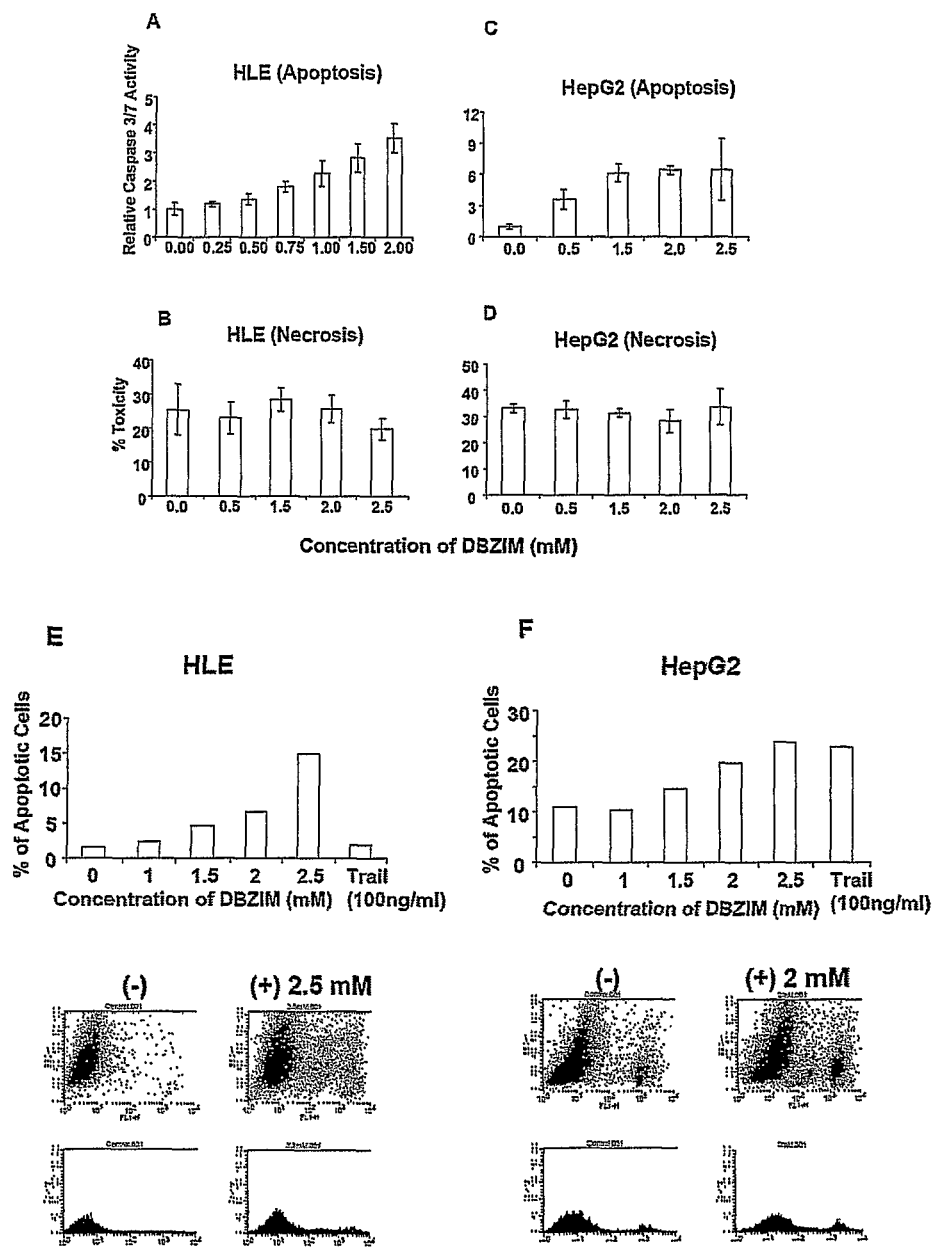
FIG. 22. DBZIM induced caspase 3/7 activity in HLE cells (A) and HepG2 (C) and did not cause LDH releasing in HLE (B) and HepG2 (D). HLE or HepG2 cells were incubated with DBZIM of various concentrations for 6 hr, and assayed for caspase 3/7 activity and LDH releasing (expressed as % toxicity). DBZIM induced apoptosis as characterized by annexin V staining using flow cytometer in HLE (E) and HepG2 (F). Scatter plot and histogram gave the representative information on the cell population distribution while bar graphs quantified the percentage of apoptotic cells from the histogram. HLE and HepG2 cells were treated by DBZIM of various concentrations for 24 hr before harvesting for annexin V staining and flow cytometric analysis.

Hepatocellular carcinoma (HCC) is known to develop over liver insults, which leads to hepatocyte inflammation and regeneration, matrix protein remodeling, fibrosis/cirrhosis and eventually HCC. HCC is inherently chemotherapy-resistant and is know to express the drug-resistant gene MDR-1. (Huang et al. 1999, Kato et al. 2001) Advanced HCC also shows poor prognosis even after a successful surgical resection (Ariizumi et al. 2004). The data showed that 1 IMS compound DBZIM can induce apoptosis an in both differentiated (HepG2) and undifferentiated (HLE) HCC cell line without significant cytotoxicity (FIG. 22). DBZIM can also inhibit the proliferation of HLE (FIG. 21A) via cell cycle arrest at G0/G1 phase (FIG. 21B).

Figure 23:
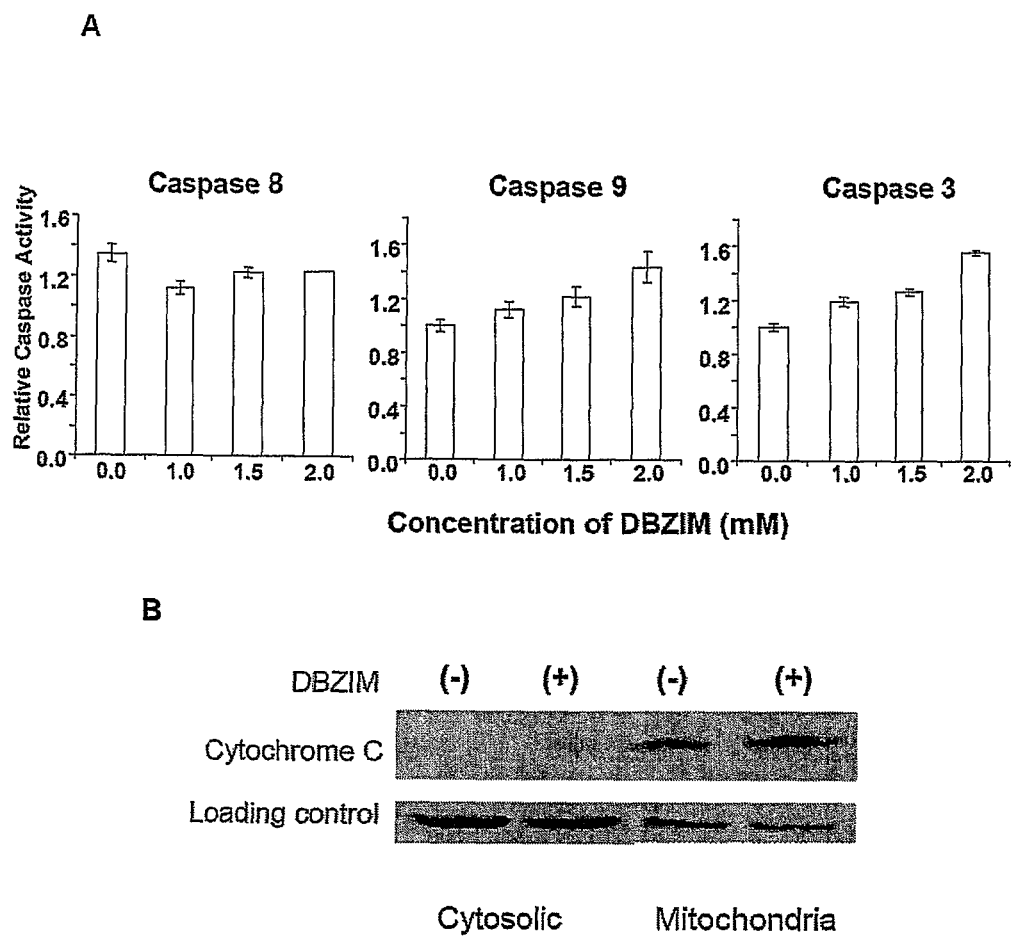
FIG. 23. (A). DBZIM did not change caspase 8 activity and induced caspase 9 and 3 activity in HLE cells. HLE cells were grown in a T75 flask and treated with DBZIM for 24 hr. The cells were then lysed and cytoplasmic protein was collected for assaying caspase 8, 9 and 3 using kits from Biovision. The data was normalized against the vehicle control. (B). DBZIM did not cause cytochrome c release from mitochondria to cytosol. HLE cells were treated by DBZIM of 1.5 mM for 24 hr. Cytosolic and mitochondria protein fractions were collected using a kit from Biovision. 15 µg of each protein was resolved in 4-12% gradient PAGE-SDS gel. The target proteins were recognized by antibody of cytochrome C, and visualized by the ECL method. The membrane was stripped and probed for the α-tubulin as the loading control for cytosolic fraction and Cox4 for mitochondria fraction.

Apoptosis can be triggered through either the extrinsic pathway or the intrinsic pathway. The extrinsic pathway is initiated through the simulation of transmembrane death receptors such as Fas receptors and activation of caspase 8 which leads to caspase 3/7 cleavage. The intrinsic pathway is initiated through the release of apoptosis activators from mitochondria and activation of caspase 9 is involved to cleave caspase 3/7 which leads to apoptosis. In this study, enzyme activity assays showed that DBZIM induced the activities of caspase 9 and 3 but not caspase 8 (FIG. 23). Further experiment by Western blotting showed that DBZIM also regulated the expression of Bcl-$X_L$ and Bak to induce the apoptosis (FIG. 24). This evidence suggests that DBZIM mainly caused the mitochondria-mediated apoptosis through the regulation of Bcl-2 favoring the occurrence of apoptosis. Meanwhile, it was found that AIF but not cytochrome C (FIG. 23d and FIG. 26) was released from mitochondria to activate caspases and/or cause chromatin condensation/DNA fragmentation. AIF has been generally implicated in the caspase-independent mode of cell apoptosis and been proposed as a new drug target. (Mignotte et al. 1998, Lorenzo et al. 2007). However it has also been shown to act in a caspase-dependant manner. (Amoult et al. 2003) DBZIM was also shown to down-regulate survivin (FIG. 24) and induce cytoplasm location of survivin (FIG. 25). Survivin is one member of IAPs protein family, expressed during human foetal development and in several neoplasms, but not in normal tissue except in thymus and placenta. It has been shown that nuclear translocation of surviving in HCC promotes the cancer cell growth. (Moon et al. 2003) Nuclear and cytoplasmic expression of survivin has also been related to prognosis of pancreatic cancer (Tonini et al. 2005). DBZIM perturbated the regulatory mechanism by translocation of survivin and suggesting a possible new angle for searching for HCC chemotherapy.

Figure 28:
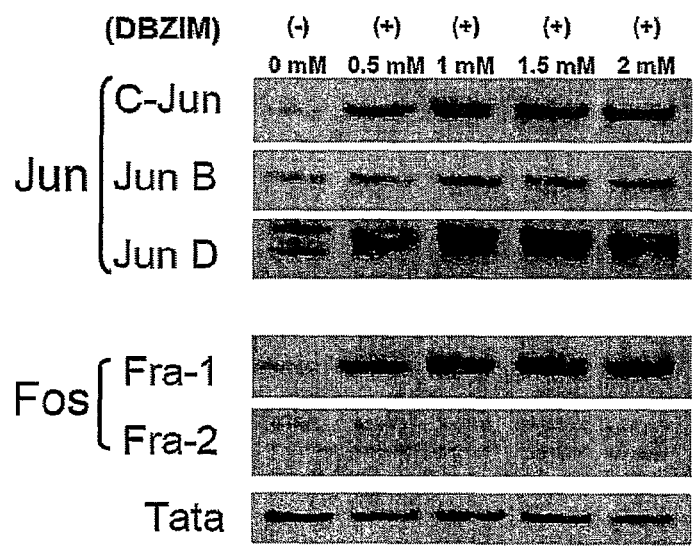
FIG. 28. DBZIM induced up-regulation of AP-1 expression in HepG2 cells. HepG2 cells were treated with DBZIM for 24 hr. Cytoplasmic and nuclear proteins were fractionated using a kit from Pierce. 15 µg of nuclear proteins were resolved in 4-12% gradient PAGE-SDS gel. The target proteins were recognized by their respective antibodies, and visualized by the ECL method. The membrane was stripped and re-probed for Tata binding protein TBP as loading control.

The alteration of mitochondria function is associated with the early phases of the cell death. Meanwhile, observed inhibition of the mitochondrial respiratory chain causes the over production of ROS, which mediates the death signaling pathway. (Mignotte et al. 1998) The mode of cell death, either by apoptosis or necrosis is largely dependant on the level of intracellular ROS. Also it is difficult to differentiate whether ROS is the result or the cause of the killing process or both. In this study, it was interesting that IMSs of different concentration had different physiological effect, in terms of ROS production. In HCC cells, when DBZIM was in the micromolar range, it attenuated the ROS level slightly, which agreed with the findings in HSC-T6 cells. When DBZIM was at much higher concentration in the milimolar range, it promoted the accumulation of ROS (FIG. 27). Meanwhile, accompanying the ROS production, some members of the transcription factor AP-1 complex was found to be up-regulated by DBZIM (FIG. 28). It was reported that the integration of oxidative stress and the up-regulation of INK/c-Jun/AP-1 cascade is necessary to promote the cell death (Singh et al. 2007). Taking these results together, it is suggested that the cell killing caused by DBZIM at high dose may be mostly due to apoptosis and ROS induction.

The observations that DBZIM not only inhibited cell proliferation in HCC lines, but also several other tumor cell lines commonly used in various cancer studies, through multiple mechanisms (cell cycle arrest, apoptosis, ROS, AP-1, inhibition of pAKT, etc.) provided further support for the speculation that DBZIM indeed exerts a number of beneficial anti-tumor properties in vitro. Its potential in vivo efficacy will need to be tested in various specific tumor models for confirmation.

In the initial in vivo trial, DBZIM was administered to a HCC xenograft mouse model (Huh7 cells in nude mice) via drinking water, after the tumor growth was evident and at the log phase about 8 weeks after cell inoculation. Several observations were made. First, 3 weeks of treatment with DBZIM resulted in 40% reduction in tumor volume, which is a preliminary and significant demonstration for using DBZIM as an effective anti-tumor agent. Second, the effective dose observed for in vivo study (2 g/l) is much lower that those for in vitro cell culture study (generally in 1-2 mM). This disparity could suggest that DBZIM may have a very different PK/PD profile in vivo than in vitro. Third, the effectiveness achieved by dosing the agent in drinking water (with weekly replacement) indicates that the DBZIM is rather, stable in water and can be absorbed through gastrointestinal (GI) tract effectively to enter the general circulation. Finally, we also noticed a significant loss in body weight (by 17%) in the 3-week treatment with DBZIM, which may suggest some type of general toxicity in the mice, though no gross pathological abnormality could be identified in all major organs. Perhaps an alternative dosing scheme using this agent can be further explored to achieve maximal therapeutic effect, yet with minimal side effect.

In conclusion, by using DBZIM as a model compound for research in IMSs, it has been demonstrated that this agent has anti-tumor activity in vitro and in vivo, which warrants further efforts in chemically synthesizing and biologically characterizing additional IMS compounds with different substituents on the imidazolium ring, in order to identify candidates with more potent efficacy with reduced side effect.

Anticancer Activities of Additional IMSs

The ability of "DBZIM-like" candidate compounds to induce cancer cell death was investigated and molecular mechanisms (apoptosis and cell cycle arrest) underlying this ability were dissected. It was discovered that the basic anti-tumor properties (apoptosis and cell cycle arrest) embedded in the model DBZIM were preserved in the some of additional IMSs with different subgroups, mainly including IBN-15, -19, -24, -25, -32, compound C (DBZMIM) and compound 9 (MABZIM).

It was found that IMSs effectively inhibit tumor cell growth concomitant with induction of cell cycle arrest and apoptosis. IMSs activate ATM system and subsequently the phosphorylation and stabilization of p53. A correlation was drawn between the level of p53, phospho-p53 (Ser-15) and ATM in HLE liver cancer cells. It is well known that ATM and ATR are activated by DNA damage. Activation of the ATM pathways has long been associated with the cell cycle checkpoint induced by several DNA damage/genotoxic stress. Once activated, ATM phosphorylates various downstream molecules such as p53, MDM2, Chk1, Chk2, resulting in cell cycle arrest or cell death. Tumor suppressor gene p53 is a key element in the induction of cell cycle arrest and apoptosis following DNA damage or cellular stress in human cells and cell cycle arrest. (Saito et al. 2002, Hofseth et al, 2003) In this study, it has been shown that treatment of HLE cells with IMSs resulted in the accumulation of p53 and phospho-p53 (Ser15). It has also been found that the induction of ATM gene expression causes DNA damage and p53 activity, suggesting that p53 induced by DNA damage play an important role in IMSs-mediated cell cycle arrest. Indeed, this result is consistent with the report of Canman et al., (1998) who showed that phosphorylation of p53 at serine 15 was in response to DNA damage. The in vitro studies also showed that phosphorylation of this specific site is critical for the p53 response and subsequent IMS-induced anticancer activity. It was also found that IMSs decrease the expression of a number of genes important for cell cycling, including Cdc25A, Cdc2, and SESN2.

Up-regulated p53 protein can activate the pro-apoptotic protein BAX and inhibits Bcl-2 to cause mitochondrial dysfunction and cytochrome c release, stimulating the mitochondrial apoptotic pathway (Melino et al., 2004). In this study, it was demonstrated that IMSs inhibited Bcl-2 and activated Bax in the HLE cancer cells. It was found that IMSs effectively inhibit tumor cell growth, concomitant with induction of cell cycle arrest and apoptosis. Furthermore, the fact that IMSs do not exhibit any significant toxicity in normal lung and breast cells suggests that IMSs possesses selectivity between normal and cancer cells. The data on caspase-3 activation strongly suggest that the mechanism of IMS induced apoptosis in these liver cancer-derived cell lines might be mediated by caspase-dependent signaling leading to caspase-3 activation. In the present study, it was shown that IMSs have cytotoxic activity toward cancer cells harboring mutant p53 and can activate mutant p53. In the present study, the inhibitory effects of IMSs to malignant tumor cell lines with mutant p53 status was investigated. The mitochondrial apoptotic pathway has been described as important in signalling apoptotic cell death for mammalian cells (Pilch et al 2003; Kluck et al., 1997). Following the treatment of HLE cells with IMSs, it was observed that IMSs treatment resulted in a significant increase of Bax expression, and a decrease of Bcl-2 suggesting that changes in the ratio of pro-apoptotic and anti-apoptotic Bcl-2 proteins might contribute to the apoptosis-promotion activity of IMSs. The activation of caspase-3 and caspase-9 was also observed after HLE cells were treated with IMSs. These results confirm that IMS-induced apoptosis is associated with regulation of BAX and Bcl-2 proteins.

Here it is demonstrated that, in addition to DBZIM, compound 9 or C9 displays a potent anti-tumor activity in the HCC xenograft model, and yet shows no apparent general toxicity. This preliminary evidence provides proof of the concept that chemical modification based on a core DBZIM structure can significantly improve the anti-tumor efficacy and reduce side effects. For example, C9 at concentration (1.5 g/l) can have much higher potency than DBZIM at a higher concentration (2 g/l), when administered via same route for the same period of time.

Thus the present study demonstrated that: (1) human liver cancer HLE cells are highly sensitive to growth inhibition by IMSs. (2) IMSs reduced survival of HLE cells via cell cycle arrest and apoptosis induction in a p53-dependent manner, and by decreasing the expression of Cdc2, Cdc25A. (3) IMSs inhibited cell growth in the HLE cells via activation of ATM, which stabilizes p53 by phosphorylation of p53 at Ser15 and decreasing the interaction of p53 and MDM2. (4) IMSs triggered mitochondrial apoptotic pathway by regulation of Bcl-2 and BAX proteins expression. These findings suggest that IMSs are a promising class of low toxic chemopreventive agents against human liver cancer cells, and other tumor cell types.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Concentrations given in this specification, when given in terms of percentages, include weight/weight (w/w), weight/volume (w/v) and volume/volume (v/v) percentages.

As used in this specification and the appended claims, the singular forms "a", "an" and "the" include plural reference unless the context clearly dictates otherwise. As used in this specification and the appended claims, the terms "comprise", "comprising", "comprises" and other forms of these terms are intended in the non-limiting inclusive sense, that is, to include particular recited elements or components without excluding any other element or component. Unless defined otherwise all technical and scientific terms used herein have the same meaning as commonly understood to one of ordinary skill in the art to which this invention belongs.

REFERENCES

Ali S, Mann D A. Signal transduction via the NF-κB pathway: A targeted treatment modality for infection, inflammation and repair. Cell Biochem Funct 2004; 22:67-79.

Agarwal M. L., Taylor W. R., Chernov M. V., Chernova O. B. and Stark, G. R. The p53 network, J. Biol. Chem. 273 (1998), pp. 1-4.

Amoult D, Gaume B, Karbowski M, Sharpe J C, Cecconi F, Youle R J. Mitochondrial release of AIF and EndoG requires caspase activation downstream of Bax/Bak-mediated permeabilization. EMBO J. 2003; 22(17):4385-4399.

Anderson C. W., and Appella E. Signaling to the p53 tumor suppressor through pathways activated by genotoxic and non-genotoxic stresses in: R A Bradshaw, E. A. Dennis (Eds.), Handbook of cell signaling, vol. 3 Academic Press, New York, 2003.

Apella E., and Anderson C. W. Post-translational modifications and activation of p53 by genotoxic stresses, Eur. J. Biochem. 268 (2001) 2764-2772.

Ariizumi S, Takasaki K, Yamamoto M, Ohtsubo T, Katsuragawa H, Katagiri S. Histopathologic differentiation of the main nodule determines outcome after hepatic resection for synchronous multi-centric hepatocellular carcinomas. Hepatogastroenterology. 2004; 51:500-504.

Avila M A, Berasain C, Sangro B, Prieto J. New therapies for hepatocellular carcinoma. Oncogene 2006; 25:3866-3884.

Bachem M G, Meyer D, Melchior R, et al. Activation of rat liver perisinusoidal lipocytes by transforming growth factors derived from myofibroblastlike cells. A potential mechanism of self-perpetuation in liver fibrogenesis. J Clin Invest 1992; 89:19-27.

Baker M V, Barnard P J, Berners-Price S J, Brayshaw S K, Hickey J L, Skelton B W, White A H. Cationic, linear Au(I) N-heterocyclic carbene complexes: Synthesis, structure and anti-mitochondrial activity. Dalton Trans 2006; 3708-3715.

Banin S., Moyal L., Sheih S., Taya Y., Anderson C. W., Chessa L., Smorodinsky N. I., Prives C., Reiss Y., Shiloh Y, and Ziv Y., Enhanced phosphorylation of p53 by ATN in response to DNA damage, Science 281 (1998) 1674-1677.

Barnard P J, Baker M V, Berners-Price S J, Day D A. Mitochondrial permeability transition induced by dinuclear gold(I)-carbene complexes: Potential new antimitochondrial antitumour agents. J Inorg Biochem 2004; 98:1642-1647.

Bataller R, Brenner D A (2005) Liver fibrosis. J Clin Invest 115(2): 209-218.

Baur J A, Pearson K J, Price N L, Jamieson H A, Lerin C, Kalra A, et al. Resveratrol improves health and survival of mice on a high-calorie diet. Nature 2006; 444: 337-342.

Bergamo A, Sava G. Ruthenium complexes can target determinants of tumour malignancy. Dalton Trans. 2007; 1267-1272.

Bourissou D, Guerret O, Gabbai F P, Bertrand G. Stable carbenes. Chem. Rev. 2000; 100:39-91.

Boydston A. J., Williams K. A., Bielawski C. W., J. Am. Chem. Soc., 2005, 127, 12496.

Britton R S, Bacon B R. Role of free radicals in liver diseases and hepatic fibrosis. Hepatogastroenterol 1994; 41:343-348.

Bykov, V J; Issaeva, N; Shilov, A; Hultcrantz, M; Pugacheva, E; Chumakov, P; Bergman, J; Wiman, K G; Selivanova, G. Restoration of the tumor suppressor function to mutant p53 by a low-molecular-weight compound. Nat. Med. 2002; 8:282-8.

Canman C. E., Lim D. S, Cimprich K. A., Taya Y., Tamai K., Sakaguchi K. A, Appella E., Kastan M. B., Siliciano J. D, Activation of the ATM kinase by ionizing radiation and phosphorylation of p53 Science 281 (1998) 1677-1679

Cao X G, Li X X, Bao Y Z, Zing N Z, Chen Y. Responses of human lens epithelial cells to quercetin and DMSO. Invest Ophthalmol Vis Sci. 2007; 48(8):3714-3718.

Caron de Fromentel, C; Gruel, N; Venot, C; Debussche, L; Conseiller, E; Dureuil, C; Teillaud, J L; Tocque, B; Bracco, L. Restoration of transcriptional activity of p53 mutants in human tumor cells by intracellular expression of anti-p53 single chain Fv fragments. Oncogene. 1999; 18:551-7.

Casanovas A, Olmos G, Ribera J, Boronat M A, Esquerda J E, Garcia-Sevilla J A. Induction of reactive astrocytosis and prevention of motoneuron cell death by the I2-imidazoline receptor ligand LSL 60101. Br J Pharmacol 2000; 130: 1767-1776.

Casini A, Ceni E, Salzano R, Biondi P, Parola M, Galli A, Foschi M, et al. Neutrophil-derived superoxide anion induces lip peroxidation and stimulates collagen synthesis in human hepatic stellate cells: Role of nitric oxide. Hepatology 1997; 25:361-367.

Chan D. W., S. C. Son, W. Block, R. Ye, K. K. Khanna, M. S. Wold, P. Douglas, A. A. Goodazri, J. Pelley, Y. Taya, M. F. Lavin, S. P. Lees-Miller, Purification and characterization of human placenta: a manganese-dependent, wortmannin-sensitive serine/threonine protein kinase, J. Biol Chem. 275 (2000) 7803-7810.

Chavez E, Reyes-Gordillo K, Segovia J, Shibayama M, Tsutsumi V, Vergara P, Moreno M G, Muriel P. Resveratrol prevents fibrosis, NF-κB activation and TGF-β increases induced by chronic $CCl_4$ treatment in rats. J. Appl. Toxicol. 2007; in press.

Chen A, Zhang L, Xu J, Tang J. The antioxidant (−)-epigallocatechin-3-gallate inhibits activated hepatic stellate cell growth and suppresses acetaldehyde-induced gene expression. Biolchem J 2002; 368(Pt 3):695-704.

Chianese R. A. and Cratree R. H. Organometallics, 2005, 24, 4432.

Das A, Banik N L, Ray S K. Garlic compounds generate reactive oxygen species leading to activation of stress kinases and cysteine proteases for apoptosis in human glioblastoma T98G and U87MG cells. Cancer. 2007; 10(5) 1083-1095.

De Bleser P J, Xu G, Rombouts K, Rogiers V, Geerts A. Glutathione levels discriminate between oxidative stress and transforming growth factor-β signaling in activated rat hepatic stellate cells. J Biol Chem. 1999:274(8)3381-3387.

Deuffic S, Poynard T, Buffat L, Valleron A J. Trends in primary liver cancer. Lancet 1998; 351:214-215.

Dominianni S J, Yen T Y. Oral Hypoglycemic Agents. Discovery and Structure-Activity Relationships of Phenacylimidazolium Halides. J. Med. Chem. 1989; 32:2301-2306.

Droge W. Free radicals in the physiological control of cell function. Physiol Rev 2002; 82:47-95.

El-Serag H B, Davila J A, Petersern N J, McGlynn K A. The continuing increase in the incidence of hepatocellular carcinoma in the United States: an update. Ann Intern Med 2003; 139:817-823.

El-Serag H B, Mason A C. Rising incidence of hepatocellular carcinoma in the United States. N Engl J Med 1999; 340: 745-750.

Elsharkawy A M, Mann D A. Nuclear factor-kappaB and the hepatic inflammation-fibrosis-cancer axis. Hepatology 2007; 46(2):590-597.

Fei P, and El-Diery, W. S. P53 and radiation responses, Oncogene 22 (2003)5774-5783.

Floyd R A. Nitrones as therapeutics in age-related diseases. Aging cell 2006; 5(1):51-57.

Frei B, Higdon J V. Antioxidant activity of tea polyphenols in vivo: Evidence from animal studies. J Nutr 2003; 133: 3275S-3284S.

Friedler, A; Hansson, L O; Veprintsev, D B; Freund, S M; Rippin, T M; Nikolova, P V; Proctor, M R; Rudiger, S; Fersht, A R. A peptide that binds and stabilizes p53 core domain: Chaperone strategy for rescue of oncogenic mutants. Proc Natl Acad Sci USA. 2002; 99:937-942.

Friedman S L (2008) Hepatic stellate cells: protean, multi-functional, and enigmatic cells of the liver. Physiol Rev 88(1): 125-172.

Friedman S L (2008b) Mechanisms of hepatic fibrogenesis. Gastroenterology 134(6): 1655-1669.

Friedman S L. Liver fibrosis—from bench to bedside. J Hepatol 2003; 38(Suppl 1):S38-53.

Fu Y, Zhou Y, Zheng S, Chen A. The antifibrogenic effect of (−)-epigallocatechin gallate results from the induction of de novo synthesis of glutathione in passaged rat hepatic stellate cells. Lab Invest 2006; 86:697-709.

Galli A, Svegliati-Baroni G, Ceni E, Milani S, Ridolfi F, Salzano R, Tarocchi M, Grappone C, Pellegrini G, Benedetti A, Surrenti G, Casini A, Oxidative stress stimulates proliferation and invasiveness of hepatic stellate cells via a MMP2-mediated mechanism. Hepatology 2005; 41(5): 1074-1084.

Giaccia A. J. and Kastan M. B., The complexity of p53 modulation: emerging patterns from divergent signals, Genes Dev. 12 (1998), pp. 2973-2983.

Harrison S A, Torgerson S, Hayashi P, Ward J, Schenker S. Vitamin E and vitamin C treatment improves fibrosis in patients with non-alcoholic steatohepatitis. Am J Gastroenterol 2003; 98:2485-2490.

Halliwell B, Whiteman M. Measuring reactive species and oxidative damage in vivo and in cell culture: How should you do it and what do the results mean? Br J Pharmacol 2004; 142:231-255.

Harlow K J, Hill A F, Welton T, Convenient and general synthesis of symmetric N,N'-disubstituted imidazolium halides, Synthesis, 1996; 6:697-698.

Hofseth L. J., S. Saito, S. P. Hussain, M. G. Espey, K. M. Miranda, Y. Araki, C. Jhappan, Y. Higashimotto, P. He. S. P. Linke, M. M. Quezado, I. Zurer, V. Rater, D. A. Wink, E. Appella, C. C. Harris, Nitric oxide-induces cellular stress and p53 activation in chronic inflammation Proc. Natl. Acad. Sci. USA 100 (2003) 143-148.

Hollstein, M; Sidransky, D; Vogelstein, B; Harris, CC. p53 mutations in human cancers. Science. 1991; 253:49-53.

Hou Z, Sang S, You H, Lee M J, Hong J, Chin K V, Yang C S. Mechanism of action of (−)-epigallocatechin-3-gallate: Auto-oxidation-dependent inactivation of epidermal growth factor receptor and direct effects on growth inhibition in human esophageal cancer KYSE 150 cells. Cancer Res 2005; 65(17):8049-8056.

Huang A, Liu G. The study of innate drug resistance of human hepatocellular carcinoma Bel7402 cell line. Cancer lett. 1999; 135:97-105.

Hupp, T R; Sparks, A; Lane, D P. Small peptides activate the latent sequence-specific DNA binding function of p53. Cell. 1995; 83:237-45. doi: 10.1016/0092-8674(95) 90165-5.

Hussain, S P; Hofseth, L J; Harris, C C. Radical causes of cancer. Nat Rev Cancer. 2003; 3:276-285.

Iredale J P (2007) Models of liver fibrosis: exploring the dynamic nature of inflammation and repair in a solid organ. J Clin Invest 117(3): 539-548.

Iredale J P (2003) Cirrhosis: new research provides a basis for rational and targeted treatments. Bmj 327(7407): 143-147.

Jakubikova J, Sedlak J. Garlic-derived organosufides induce cytotocity, apoptosis, cell cycle arrest and oxidative stress in human colon carcinoma cell line. Neoplasma. 2006; 53(3): 191-199.

Kato A, Miyazaki M, Ambiru S, Yoshitomi H, Ito H, Nakagawa K, Shimizu H, Yokosuka O, Nakajima N. Multidrug resistance gene (MDR-1) expression as a useful prognostic factor in patients with human hepatocellular carcinoma after surgical resection. J Surg Oncol. 2001; 78(2):110-115.

Katzenellenbogen M, Nizrahi L, Pappo R, Klopstock N, Olam D, Barash H, Domany E, Galun E, Glodenberg D. Molecular mechanisms of the chemopreventive effect on hepatocellular carcinoma development in Mdr2 knockout mice. Mol Cancer Ther. 2007; 6(4): 1283-1291.

Kawada N, Seki S, Inoue M, Kuroki T. Effect of antioxidants, resveratrol, wuercetin, and N-acetylcysteine, on the functions of cultured rat hepatic stellate cells and Kupffer cells. Hepatology 1998; 27:1265-1274.

Keum Y S, Chang P P J, Kwon J H, Yuan X L, Li W, Hu L, Kong A N T. 3-Morpholinoproply isothiocyanate (3MP-ITC) is a novel synthetic isothiocyanate that strongly induces the antioxidant response element (ARE)-dependent Nrf2-mediated detoxifying/antioxidant enzymes in vitro and in vivo. Carcinogenesis 2007; in press.

Kluck R M, Bossy-Wetzel E, Green D R, Newmeyer D D The release of cytochrome c from mitochondria: A primary site for Bcl-2 regulation of apoptosis. Science 275 (1997): 1132-1136.

Ko, L J; Prives, C. p53: puzzle and paradigm. Genes & Dev. 1996; 10:1054-72.

Lin L C, Hung L C, Tsai T H. Determination of (−)-epigallocatechin gallate in rat blood by microdialysis coupled with liquid chromatography. J Chromatogr 2004; 1032(1-2):125-128.

Liu S L, Degli Esposti S, Yao T, Diehl A M, Zern M A. Vitamin E therapy of acute $CCl_4$-induced hepatic injury in mice is associated with inhibition of nuclear factor-kappaB binding. Hepatology 1995; 22:1474-1481.

Llovet J M, Burroughs A, Bruix J. Hepatocellular carcinoma. Lancet. 2003; 362:1907-17.

Lorenzo H K, Susin S A. Therapeutic potential of AIF-mediated caspase-independent programmed cell dealth. Drug Resist Updat. 2007; 10(6):235-255

Lu G, Shimizu I, Cui X, Itonaga M, Tamaki K, Fukuno H, Inoue H, Honda H, Ito S. Interferon-alpha enhances biological defense activities against oxidative stress in cultured rat hepatocytes and hepatic stellate cells. J Med Invest 2002; 49(3-4):172-181.

Maples K R, Green A R, Floyd R A. Nitrone-related therapeutics: Potential of NXY-059 for the treatment of acute ischaemic stroke. CNS Drugs 2004; 18(15):1071-1084.

Maubach G, Lim M C C, Zhang C Y, Zhuo L. GFAP promoter directs lacZ expression specifically in a rat hepatic stellate cell line. World J of Gastroentero 2006; 12:723-730.

Meurer S K, Lahme B, Tihaa L, Weiskirchen R, Gressner A M. N-acetyl-L-cysteine suppresses TGF-β signaling at distinct molecular steps: The biochemical and biological efficacy of a multifunctional, antifibrotic drug. Biochem Pharmaco 2005; 70:1026-1034.

Mignotte B, Vayssiere J-L. Mitochondria and apoptosis. Eur. J. Biochem. 1998; 252:1-15.

Moon W Sung, Tarnawski A. Nuclear Translocation of survivin in hepatocellular carcinoma: a key to cancer cell growth. Hum Pathol. 2003; 34(11):1119-1126.

Nakanuta M, Higashi N, Kohjima M, Fukushima M, Ohta S, Kotoh K, Kobayashi N, Enjoji M. Epigallocatechin-3-gallate, a polyphenol component of green tea, suppresses both collagen production and collagenase activity in hepatic stellate cells. Int J Mol Med 2005; 16:677-681.

Naugler W E, Sakurai T, Kim S, Maeda S, Kin K H, Elsharkawy A M, Karin M. Differences in MyD88-dependent IL-6 Production. Science 2007; 317:121-124.

Nishikawa T, Nakajima T, Moriguchi M, Jo M, Sekoguchi S, Ishii M, Takashima H, Katagishi T, Kimura H, Minami M, Itoh Y, Kagawa K, Okanoue T. A green tea polyphenol, epigalocatechin-3-gallate, induces apoptosis of human hepatocellular carcinoma, possible through inhibition of Bcl-2 family protein. J. Hepatol. 2006; 44:1074-1082.

Olmos G, DeGregorio-Rocasolano N, Regalado M P, Gasull T, Boronat M A, Trullas R, Villarroel A, Lerma J, Garcia-Sevilla J A. Protection by imidazol(ine) drugs and agmatine of glutamate-induced neurotoxicity in cultured cerebellar granule cells through blockade of NMDA receptor. Br J Pharmacol 1999; 127:1317-1326.

Orr J G, Leel V, Cameron G A, Marek G J, Haughton E L, Elrick L J, Trim J E, Hawksworth G M, Halestrap A P, Wright M C. Mechanism of action of the antifibrogenic compound gliotoxin in rat liver cells. Hepatology 2004; 40(1):232-242.

Oster, B A; Coffey, H A; Morin, M J; Rastinejad, F. Pharmacological rescue of mutant p53 conformation and function. Science. 1999; 286:2507-10.

Padillo F J, Cruz A, Navarrete C, Bujalance I, Briceño J, Gallardo J I, Marchal T, Caballero R, Túnez I, Muntané J, Montilla P, Pera-Madrazo C. Melatonin prevents oxidative stress and hepatocyte cell death induced by experimental cholestasis. Free Radic Res 2004; 38(7):697-704.

Parkin D M, Bray F, Ferlay J, Pisani P. Estimating the world cancer burden: Globocan 2000. Int J Cancer 2001; 94:153-156.

Parola M, Pinzani M, Casini A, Leonarduzzi G, Marra F, Caligiuri A, Ceni E, et al. Induction of procollagen type I gene expression and synthesis in human hepatic stellate cells by 4-hydroxy-2,3-nonenal and other 4-hydroxy-2,3-alkenals is related to their molecular structure. Biochem Biophys Res Commun 1996; 222:261-264.

Peng J, Stevenson F F, Doctrow S R, Andersen J K. Superoxide dismutase/catalase mimetics are neuroprotective against selective paraquat-mediated dopaminergic neuron death in the substantial nigra: Implications for Parkinson disease. J Biol Chem. 2005; 280:29194-29198.

Pilch D. R., O. A. Sedelnikova, C. Redon, A. Celeste, A. Nussenzweig, W. M. Bonner, charecteristics of gamma-H2AX foci at DNA double stranded breaks sites, Biochem. Cell. Biol. 81 (2003) 123-129.

Rakoff-Nahoum S, Why Canacer and Inflammation, Yale Journal of Biology and Medicine (2006); 79; 123-130.

Saito S., H. Yamaguchi, Y, Higashimoto, C. Chao, Y. Xu, A. J. Forance Jr. E. Apella, C. W. Anderson, phosphorylation site interdependence of human p53 post-translational modifications in response to stress, J. Biol. Chem. 278 (2003) 37536-37544)

Saito S., A. A. Goodazri, Y. Higashimoto, Y. Noda, S.p. Leesmiller, E. Appella, C. W. Anderson, ATM mediates phosphorylation at multiple p53 sites, including ser(46), in response to ionizing radiation, J. Biol. Chem. 277 (2002) 12491-12494.

Selivanova, G; Iotsova, V; Okan, I; Fritsche, M; Strom, M; Groner, B; Grafstrom, R C; Wiman, K G. Restoration of the growth suppression function of mutant p53 by a synthetic peptide derived from the p53 C-terminal domain. Nat Med. 1997; 3:632-8. doi: 10.1038/nm0697-632.

Shieh S. Y., Ikeda M., Taya Y. and Prives C., DNA damage-induced phosphorylation of p53 alleviates inhibition by MDM2, Cell 91 (1997), pp. 325-334.

Siliciano J. D., C. E. Canman, Y. Taya, K. A Sakaguchi, E. Appella, M. B. Kastan, DNA damage induces phosphorylation of aminoterminus of p53, Genes Dev. 11 (1997) 3471-3481.

Smart D E, Vincent K J, Arthur M J P, et al. Control of the tissue inhibitor of metalloproteinases-1 and interleukin-6 genes in activated hepatic stellate cells. J Biol Chem. 2001; 276:24414-24421.

Smith G. C., R. B. Cary, N. D. Lakin, B. C. Hann, S. H. Teo, D. J. Chen, S. P. Jackson, Purification of DNA binding properties of ataxia-telangiectasia gene product ATM, Proc. Natl. Acad, Sci. USA 96 (1999) 11134-11139.

Taylor-Robinson S D, Foster G R, Arora S, Hargreaves S, Thomas H C. Increase in primary liver cancer in the UK, 1979-1994. Lancet 1997; 350:1142-1143.

Thomas M B. Hepatocellular Carcinoma; The Need for Progress. J. Clin. Oncol. 2005; 23(13): 2892-2899

Thorgeirsson S S, Grisham J W. Molecular phthogenesis of human heptocellular carcinoma. Nature Genetics. 2002; 31: 339-346

Tonini G, Vinvenzi B, Santini D, Scarpa S, Vasaturo T, Malacrino C, Coppola R, magistrelli P, Borzomati D, Baldi A, Antinori A, Caricato M, Nuzzo G, Picciocchi A. Nuclear and cytoplasmic expression of suvivin in 67 sugically resected pancreatic cancer patients. Br J Cancer. 2005; 92:2225-2232.

Tsukamoto H, Rippe R, Niemela O, Lin M. Roles of oxidative stress in activation of Kupffer and Ito cells. J Gastroenterol Hepatol 1995; 10:s50-s53.

Tsukamoto H. Cytokine regulation of hepatic stellate cell in liver fibrosis. Alcohol Clin Exp Res 1999; 23:911-916.

Vali L, Hahn O, Kupcsulik P, Drahos A, Sarvary E, Szentmihalyi K, Pallai Z, Kurucz T, Sipos P, Blazovics A. Oxidative stress with altered element content and decreased ATP level of erythrocytes in hepatocellular carcinoma and colorectal liver metastases. Eur J Gastroenterol Hepatol. 2008; 20(5); 393-398.

Valko M, Izakovic M, Mazur M, Rhodes C, Tesler J Role of oxygen radical in DNA damage and cancer incidence. Mol. Cell. Biochem. 2004; 266; 37-56.

Vasiliou V, Lee J, Pappa A, Petersen D R. Involvement of p65 in the regulation of NF-kB in rat hepatic stellate cells during cirrhosis. Biochem Biophys Res Commun 2000; 273:546-550.

Vogelstein, B; Lane, D; Levine, A J. Surfing the p53 network [news] [In Process Citation]. Nature. 2000; 408:307-10. doi: 10.1038/35042675.

Wagle D R, Vasan S, Gall M. Method of treating fibrotic diseases or other indications with imidazolium agents. Patent Application US 2007/0043016 A1. 2007.

Wahl G. M. and A. M. Carr, The evolution of diverse biological responses, to DNA damage: insights from yeast and p53, Nat. Cell Biol. 3 (2001) E277-286.

Wei Michael C., Wei-Xing Zong, Emily H.-Y. Cheng, Tullia Lindsten, Vily Panoutsakopoulou, Andrea J. Ross, Kevin A. Roth, Grant R. MacGregor, Craig B. Thompson, Stanley J. Korsmeyer. Proapoptotic BAX and BAK: A requisite gateway to mitochondrial dysfunction and death. Science 292 (2001):727-730.

Weiskirchen R, Gressner A. M. Isolation and culture of hepatic stellate cells. Methods Mol Med 2005; 117:99-113.

Whalen R, Rockey D C, Friedman S L, Boyer T D. Activation of rat hepatic stellate cells leads to loss of glutathione S-transferases and their enzymatic activity against products of oxidative stress. Hepatology 1999; 30(4):927-933.

Zhang Y, Ngeow K. C. and Ying J. Y. Organic Letters, 9 [18] (2007) 3495-3498.

Zhang C Y, Zhuo L. Epigallocatechin gallate and genistein attenuate glial fibrillary acidic protein elevation induced by fibrogenic cytokines in hepatic stellate cells. Int J Mol Med 2006; 18:1141-1151.

Zhao L, Zhang C, Zhuo L, Zhang Y, Ying, Y Y J. Imidazolium Salts: A Mild Reducing and Anti-oxidative Reagent. JACS. 2008; 130(38):12586-7.

What is claimed is:

1. A method for treating cancer selected from the group consisting of brain cancer, bone cancer, skin cancer, gallbladder cancer, laryngeal cancer, oral cancer, pleural mesothelioma, testicular cancer, uterine cancer, thyroid cancer, hepatocellular carcinoma and glioma in a subject in need of such cancer treatment, the method comprising administering an effective amount of an anti-cancer agent to the subject, the anti-cancer agent being:

(a) an oligomer or polymer comprising three or more compounds of general formula I connected together, general formula I being defined as:

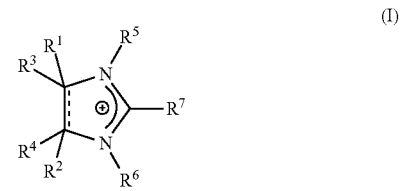

wherein:

the dashed line is absent or is present as a bond to form a second bond between the carbon to which $R^1$ and $R^3$ are attached and the carbon to which $R^2$ and $R^4$ are attached;

$R^1$:
(i) is H, straight or branched $C_1$-$C_6$ alkyl, straight or branched $C_2$-$C_6$ alkenyl, straight or branched $C_2$-$C_6$ alkynyl, $C_6$-$C_{10}$ aryl;
(ii) together with $R^2$ and their ring atoms form a 6- to 10-membered fused saturated, unsaturated or aromatic ring system;
(iii) together with $R^5$ and their ring atoms form a 5- to 10-membered fused saturated, unsaturated or aromatic ring system when $R^2$ is as defined above in (i); or
(iv) together with $R^5$ and their ring atoms form a 5- to 10-membered fused saturated, unsaturated or aromatic ring system, when $R^2$ and $R^6$ together with their ring atoms also form a 5- to 10-membered fused saturated, unsaturated or aromatic ring system;

$R^2$:
(i) is H, straight or branched $C_1$-$C_6$ alkyl, straight or branched $C_2$-$C_6$ alkenyl, straight or branched $C_2$-$C_6$ alkynyl, $C_6$-$C_{10}$ aryl;
(ii) together with $R^1$ and their ring atoms form a 6- to 10-membered fused saturated, unsaturated or aromatic ring system;
(iii) together with $R^6$ and their ring atoms form a 5- to 10-membered fused saturated, unsaturated or aromatic ring system when $R^1$ is as defined above in (i); or
(iv) together with $R^6$ and their ring atoms form a 5- to 10-membered fused saturated, unsaturated or aromatic ring system, when $R^1$ and $R^5$ together with their ring atoms also form a 5- to 10-membered fused saturated, unsaturated or aromatic ring system;

$R^3$ is H, or, when $R^1$ and $R^2$ together with their ring atoms form a 6- to 10-membered fused aromatic ring system or when the dashed line is present as a bond, $R^3$ is absent;

$R^4$ is H, or, when $R^1$ and $R^2$ together with their ring atoms form a 6- to 10-membered fused aromatic ring system or when the dashed line is present as a bond, $R^4$ is absent;

$R^5$ is:
  (i) as defined above for $R^1$; or
  (ii) straight or branched $C_1$-$C_6$ alkyl, straight or branched $C_2$-$C_6$ alkenyl, straight or branched $C_2$-$C_6$ alkynyl, $C_3$-$C_{18}$ cycloalkyl including fused cycloalkyl ring systems, $C_6$-$C_{10}$ aryl, $C_6$-$C_{10}$ aryl-$C_1$-$C_6$ alkyl, $C_6$-$C_{10}$ aryl-$C_2$-$C_6$ alkenyl, or $C_6$-$C_{10}$ aryl-$C_2$-$C_6$ alkynyl, $C_1$-$C_6$ alkyl-$C_6$-$C_{10}$ aryl, $C_2$-$C_6$ alkenyl-$C_6$-$C_{10}$ aryl, or $C_2$-$C_6$ alkynyl-$C_6$-$C_{10}$ aryl;

$R^6$ is:
  (i) as defined above for $R^2$; or
  (ii) straight or branched $C_1$-$C_6$ alkyl, straight or branched $C_2$-$C_6$ alkenyl, straight or branched $C_2$-$C_6$ alkynyl, $C_3$-$C_{18}$ cycloalkyl including fused cycloalkyl ring systems, $C_6$-$C_{10}$ aryl, $C_6$-$C_{10}$ aryl-$C_1$-$C_6$ alkyl, $C_6$-$C_{10}$ aryl-$C_2$-$C_6$ alkenyl, or $C_6$-$C_{10}$ aryl-$C_2$-$C_6$ alkynyl, $C_1$-$C_6$ alkyl-$C_6$-$C_{10}$ aryl, $C_2$-$C_6$ alkenyl-$C_6$-$C_{10}$ aryl, or $C_2$-$C_6$ alkynyl-$C_6$-$C_{10}$ aryl;

$R^7$ is H, $C_1$-$C_6$ alkyl, phenyl, substituted $C_1$-$C_6$ alkyl or halo;

in which any of $R^1$ to $R^7$, where applicable, optionally has one or more carbon atoms replaced with a heteroatom selected from N, O, S and P and is optionally substituted with one or more of straight or branched $C_1$-$C_6$ alkyl, straight or branched $C_2$-$C_6$ alkenyl, straight or branched $C_2$-$C_6$ alkynyl, $C_3$-$C_{18}$ cycloalkyl including fused cycloalkyl ring systems, $C_6$-$C_{10}$ aryl, fluoro, tri-fluoromethyl, cyanato, isocyanato, carboxyl, $C_1$-$C_6$ acyloxy, $C_1$-$C_6$ acyl, carbonyl, amino, acetyl, acetoxy, oxo, nitro, hydroxyl, $C_1$-$C_6$ alkylcarboxy, $C_1$-$C_6$ alkoxy, $C_2$-$C_6$ alkenoxy, $C_2$-$C_6$ alkynoxy; and in which one of the ring carbon atom to which $R^1$ and $R^3$ are attached and the ring carbon to which $R^2$ and $R^4$ are attached is optionally replaced with a nitrogen atom;

or any pharmaceutically acceptable salt of the oligomer or polymer of the compound; or b) 1,3-di-tert-butylimidazolinium, 1,3-bis(1-adamantyl)imidazolium, 1,3-bis(2,4,6-trimethylphenyl)-imidazolinium, 1,3-bis(2,6-diisopropyl-phenyl)-imidazolinium, 1-(1-adamantyl)-3-(2,4,6-trimethylphenyl)-4,5-dihydroimidazolinium, 2-benzylimidazo[1,5-a]quinolinium, 1,3-bis(1-adamantyl)-benzimidazolium, 1,3-diisopropylimidazolinium, diisopropylphenyl)-5-methylimidazo[1,5-a]pyridinium, 1-(2,6-diisopropylphenyl)-3-(2,4,6-trimethylphenyl)-imidazolinium, 2-mesityl-5-methylimidazo[1,5-a]pyridinium, 2-mesityl-2,5,6,7-tetrahydropyrrolo[2,1-c][1,2,4]triazol-4-ium, 1,3-bis(1-adamantyl)imidazolinium, 6,7-dihydro-2-pentafluorophenyl-5H-pyrrolo[2,1-c]-1,2,4-trizolium, 1-methyl-3-(2-hydroxyethyl)-imidazolium, 1-methyl-3-(4-isocynatobenzyl)-imidazolium, 1-methyl-3-(4-acetate-benzyl)-imidazolium, 1-methyl-3-(2,2-dimethoxyethyl)-imidazolium, 1-(2,4,6-trimethylphenyl)-3-(4-acetate-benzyl)-imidazolium, 1-benzyl-3-(4-acetate-benzyl)-2-methyl-imidazolium, 1-benzyl-3-(2,2-dimethoxyethyl)-2-methyl-imidazolium, 1-benzyl-3-(4-acetatebenzyl)-5-phenyl-imidazolium, 1-benzyl-3-(4-methylbenzyl)-5-phenylimidazolium, 1-benzyl-3-(3-hydroxyl-propyl)-imidazolium, 1-benzyl-3-(4-acetatebenzyl)-imidazolium, 1-(4-cyanatobenzyl)-3-methyl-imidazolium, 1-(4-carboxybenzyl)-3-methyl-imidazolium, 1,3-Bis(2,6-diisopropylphenyl) imidazolium or 1,3-Di-tert-butylimidazolium, or any dimer thereof; or any pharmaceutically acceptable salt thereof; or c) 2,6-di-(3-benzyl-imidazolium)-pyridine, 2,2'-di-(3-benzyl-imidazolium)-1,1'-binaphthalene, (1,2-4,5-diimidazolium)-N,N',N'',N'''-tetrabenzyl-benzene, 1,3,5-tris-(4-methyl-imiazolium)-linked cyclophane or 1,3-dibenzyl-2-(1,3-dibenzyl-1H-imidazol-2(3H)-ylidene)-2,3-dihydro-1H-imidazole; or any pharmaceutically acceptable salt thereof.

2. The method of claim 1 wherein the compound of general formula I is an imidazolium or an imidazolium salt.

3. The method of claim 1 wherein $R^5$ is the same as $R^6$.

4. The method of claim 1 wherein $R^5$ and $R^6$ are hydrocarbons.

5. The method of claim 1 in wherein the pharmaceutically acceptable salt is a chloride, bromide, tetrafluoroborate or hexafluorophosphate salt.

6. The method of claim 1 wherein the anti-cancer agent is an oligomer or polymer of 1-ethyl-3-methylimidazolium, 1,3-bisbenzylimidazolium, 1,3-diisopropylimidazolium, 1,3-di-tert-butylimidazolinium, 1,3-bis(1-adamantyl)imidazolium, 1,3-bis(2,4,6-trimethylphenyl)-imidazolinium, 1,3-bis(2,6-diisopropyl-phenyl)-imidazolinium, 1,3-diallylimidazolium, 1-benzyl-3-methylimidazolium, 1-butyl-3-methylimidazolium, 1-(1-adamantyl)-3-(2,4,6-trimethylphenyl)-4,5-dihydroimidazolium, 2-benzylimidazo[1,5-a]quinolinium, 1,3-bis(1-adamantyl)-benzimidazolium, 1,3-dicyclohexylbenzimidazolium, 1,3-diisopropylimidazolinium, 1,3-diisopropylimidazolium, 2-(2,6-diisopropylphenyl)-5-methylimidazo[1,5-a]pyridinium, 1-(2,6-diisopropylphenyl)-3-(2,4,6-trimethylphenyl)-imidazolinium, 2-mesityl-5-methylimidazo[1,5-a]pyridinium, 2-mesityl-2,5,6,7-tetrahydropyrrolo[2,1-c][1,2,4]triazol-4-ium, 1,3-bis(1-adamantyl)imidazolinium, 1-butyl-3-(2-pyridinylmethyl)-1H-imidazolium, 6,7-dihydro-2-pentafluorophenyl-5H-pyrrolo[2,1-c]-1,2,4-trizolium, 1-methyl-3-(2-hydroxylethyl)-imidazolium, 1-methyl-3-(4-isocynatobenzyl)-imidazolium, 1-methyl-3-(4-carboxylbenzyl)-imidazolium, 1-methyl-3-(4-acetatebenzyl)-imidazolium, 1-methyl-3-(2,2-dimethoxyethyl)-imidazolium, 1-(2,4,6-trimethylphenyl)-3-(4-acetatebenzyl)-imidazolium, 1,3-Dibenzyl-5-phenylimidazolium, 1-benzyl-3-(4-carboxylbenzyl)-2-methylimidazolium, 1-benzyl-3-(3,4,5-trimethoxylbenzyl)-2-methylimidazolium, 1-benzyl-3-(4-acetate-benzyl)-2-methyl-imidazolium, 1-benzyl-3-(4-methylcarboxylatebenzyl)-2-methyl-imidazolium, 1-benzyl-3-(2,2-dimethoxyethyl)-2-methyl-imidazolium, 2,6-di-(3-benzyl-imidazolium)-pyridine, 2,2'-di-(3-benzyl-imidazolium)-1,1'-binaphthalene, 1-benzyl-3-(4-methylbenzyl)-imidazolium, 1-benzyl-3-(2-trifluoromethylbenzyl)-2-methylimidazolium, 1-benzyl-3-(4-methylcarboxylatebenzyl)-5-phenyl-imidazolium, 1-benzyl-3-(4-acetatebenzyl)-5-phenyl-imidazolium, 1-benzyl-3-(4-methylbenzyl)-5-phenylimidazolium, (1,2-4,5-diimidazolium)-N,N',N'',N'''-tetrabenzyl-benzene, 1-benzyl-3-(2-propyn-1-yl)-imidazolium, 1-benzyl-3-(3-hydroxylpropyl)-imidazolium, 1,3-di(2-phenylethyl)-imidazolium, 1-benzyl-3-(4-acetatebenzyl)-imidazolium, 1-benzyl-3-(pyridin-2-yl)-imidazolium, 1,3,5-tris-(4-methyl-imiazolium)-linked cyclophane, 1,3-dibenzyl-2-(1,3-dibenzyl-1H-imidazol-2(3H)-ylidene)-2,3-dihydro-1H-imidazole, 1-benzyl-3-methyl-imidazolium, 1-(4-cyanatobenzyl)-3-methylimidazolium, 1-(4-carboxybenzyl)-3-methyl-imidazolium, 1,3-dibenzylbenzimidazolium, 1,3-dibenzyl-2-methylimidazolium, 1,3-Bis(2,6-diisopropylphenyl)imidazolium or 1,3-Di-tert-butylimidazolium, or any pharmaceutically acceptable salt thereof.

7. The method of claim 1 wherein the anti-cancer agent is a trimer of a compound having a structure of general formula I or any pharmaceutically acceptable salt thereof.

8. The method of claim 1 wherein the cancer is hepatocellular carcinoma or glioma.

9. The method of claim 8 wherein the anti-cancer agent is 1-(2,4,6-trimethylphenyl)-3-(4-acetate-benzyl)-imidazolium or 1-benzyl-3-(4-acetate-benzyl)-2-methyl-imidazolium, or an oligomer or polymer of 1,3-Bisbenzylimidazolium, 1, 3,-Dibenzyl-2-methylimidazolium, 1,3-Dibenzyl-5-phenylimidazolium, 1-benzyl-3-(4-methylbenzyl)-imidazolium, 1-benzyl-3-(2-trifluoromethylbenzyl)-2-methylimidazolium or 1,3-di(2-phenylethyl)-imidazolium, or any pharmaceutically acceptable salt thereof.

10. The method of claim 1 wherein the cancer is brain cancer, bone cancer, skin cancer, gallbladder cancer, laryngeal cancer, oral cancer, pleural mesothelioma, testicular cancer, uterine cancer or thyroid cancer.

* * * * *

UNITED STATES PATENT AND TRADEMARK OFFICE
CERTIFICATE OF CORRECTION

| | | |
|---|---|---|
| PATENT NO. | : 9,072,729 B2 | Page 1 of 1 |
| APPLICATION NO. | : 12/865668 | |
| DATED | : July 7, 2015 | |
| INVENTOR(S) | : Zhuo et al. | |

Figure 12:
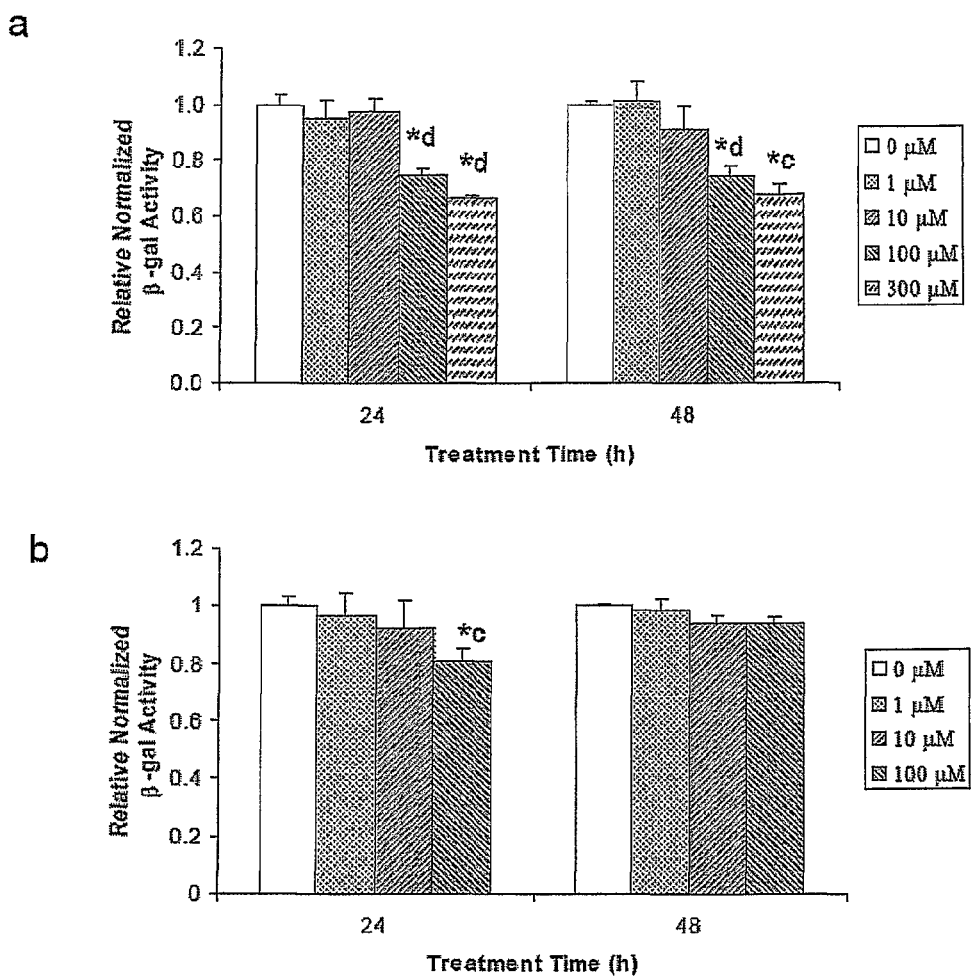
FIG. 12. (a) DBZIM and (b) TDBZIM attenuated GFAP-LacZ transgene as reported by β-galactosidase activity. Stable transfected T6 GFAP-LacZ cells were treated with compounds of 1-300 μM concentrations, and assayed after 24 h and 48 h. The β-galactosidase activity was normalized to the total protein, and presented as relative value after comparing to the vehicle control. The data were presented as mean and SEM, N=6, *$^c$P<0.005, and *$^d$P<0.0005, when compared to the vehicle control.

It is certified that error appears in the above-identified patent and that said Letters Patent is hereby corrected as shown below:

In the Specification:

Column 9, line 50, "FIG. 12. (a) DBZIM and (b) TDBZIM attenuated" should read -- FIG. 12. DBZIM (top panel) and TDBZIM (bottom panel) attenuated --

Column 13, line 52, "Table 1. Names" should read -- FIG. 45 (Table 1). Names --

Column 13, line 53, "Table 2. IC50" should read -- FIG. 46 (Table 2). IC50 --

Column 13, line 54, "Table 3. IC50" should read -- FIG. 47 (Table 3). IC50 --

Column 13, line 55, "Table 4. IC50" should read -- FIG. 48 (Table 4). IC50 --

Column 13, line 57, "Table 5. IC50" should read -- FIG. 49 (Table 5). IC50 --

Column 13, line 59, "Table 6. IC50" should read -- FIG. 50 (Table 6). IC50 --

Column 13, line 61, "Table 7. IC50" should read -- FIG. 51 (Table 7). IC50 --

Column 37, line 39, "(FIG. 12a). For" should read -- (FIG. 12 (top panel)). For --

Column 37, line 40, "24 h (FIG. 12b)." should read -- 24 h (FIG. 12 (bottom panel)). --

Signed and Sealed this
Second Day of August, 2016

Michelle K. Lee
*Director of the United States Patent and Trademark Office*